(12) United States Patent
Yavuz et al.

(10) Patent No.: US 6,522,712 B1
(45) Date of Patent: Feb. 18, 2003

(54) RECONSTRUCTION OF COMPUTED TOMOGRAPHIC IMAGES USING INTERPOLATION BETWEEN PROJECTION VIEWS

(75) Inventors: Mehmet Yavuz, Irving, TX (US); Erdogan Cesmeli, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 251 days.

(21) Appl. No.: 09/656,977

(22) Filed: Sep. 7, 2000

Related U.S. Application Data

(60) Provisional application No. 60/197,208, filed on Apr. 14, 2000, and provisional application No. 60/166,499, filed on Nov. 19, 1999.

(51) Int. Cl.[7] ................................................ A61B 6/03
(52) U.S. Cl. ................................................ 378/4; 378/8
(58) Field of Search ........................... 378/4, 8, 15, 901

(56) References Cited

U.S. PATENT DOCUMENTS

| | | |
|---|---|---|
| 5,046,003 A | 9/1991 | Crawford |
| 5,208,746 A | 5/1993 | King et al. |
| 5,243,284 A | 9/1993 | Noll ............................ 324/309 |
| 5,291,402 A | 3/1994 | Pfoh |
| 5,627,868 A | 5/1997 | Nobuta et al. ................. 378/19 |
| 5,663,995 A | 9/1997 | Hu ............................... 378/15 |
| 5,838,756 A | 11/1998 | Taguchi et al. ................. 378/4 |
| 5,889,833 A | 3/1999 | Silver ........................... 378/15 |
| 5,997,883 A | 12/1999 | Epstein et al. |
| 6,353,653 B1 * | 5/2002 | Edic ............................. 378/4 |

FOREIGN PATENT DOCUMENTS

EP 430549 A2 11/1990

OTHER PUBLICATIONS

Internation Search Report.
"Principles of Computerized Tomographic Imaging", Avinash C. Kak & Malcolm Slaney, 126–132 & 234–247 (1988).

* cited by examiner

*Primary Examiner*—David V. Bruce
(74) *Attorney, Agent, or Firm*—Donald S. Ingraham; Christian G. Cabou

(57) ABSTRACT

An approach to image reconstruction provides enhanced image quality from limited projection data, particularly when the imaging object (or a portion of interest) is in motion during the tomographic projection data collection process. An interpolated projection view is generated from existing projection views between which an additional relationship exists by virtue of being respectively based on data collected in different data acquisition cycles. The present invention provides a technique for combining the existing projection views into an interpolated projection view by interpolation in time. A further aspect of the invention provides an approach for selecting a reconstruction range for projection data representing the imaged object and covering a plurality of projection ranges.

71 Claims, 39 Drawing Sheets

RECONSTRUCTION OF COMPUTED TOMOGRAPHIC IMAGES USING INTERPOLATION BETWEEN PROJECTION VIEWS

CROSS REFERENCE TO RELATED APPLICATIONS

This application is related to Provisional Application U.S. Ser. No. 60/166,499, filed Nov. 19, 1999 and Provisional Application U.S. Ser. No. 60/197,208, filed Apr. 19, 2000 in the U.S. Patent and Trademark Office, the contents of which are incorporated herein by reference, and the benefit of priority to which is claimed under 35 U.S.C. §119(e).

BACKGROUND OF THE INVENTION

This invention relates to generation of computed tomographic images. More particularly, the invention relates to reconstruction of such images through use of interpolated projection views generated by interpolating between existing projection views.

Computed tomography (CT) is an imaging technology in which an array of detectors generates data from energetic rays transmitted through or emitted from an imaged subject. For example, a transmission-type medical CT imaging system uses an array of x-ray detectors to detect an x-ray beam that has passed through the body of a human or animal subject. The attenuation of the beam by the subject causes the collected data, including the effects of the attenuation, to contain information about the interior structure of the subject. The detector data are processed by a computer system to generate image data representing a recognizable view of that interior structure.

CT techniques are valuable in a wide range of application areas where noninvasive and nondestructive examination of internal structures is needed. Medical applications include imaging of emissions from radioactive substances introduced into the subject (single photon emission CT, positron emission CT, etc.), as well as x-ray transmission CT. Non-medical applications include, for example, non-destructive testing and inspection, mineral deposit mapping (microseismic CT imaging), and three-dimensional image generation in electron microscopy.

A CT system generates a display image from data representing measurements of energetic signals transmitted through or emitted from a subject in a range of directions. This process is "tomographic" in that structural details of a subject are represented as a cross-sectional view along a given plane through the subject. The process is "computerized" because the raw detector data indirectly represent a view of the subject. Intensive data processing is required to convert the raw data into a recognizable view of the internal features of the subject.

Computer processing of the collected data is performed because the data correspond to mere projections of the subject structure along various different paths. The term "projection data" will be used herein for such CT data, irrespective of the application area in which the CT imaging procedure is used. The differences between the projection data for different paths through the imaged subject, in relation to the spatial separation of the paths, indirectly contain information about the interior structure of the object.

A CT reconstruction algorithm is applied to the projection data to generate image data that specify the image to be displayed. The image data are generated from the structure information indirectly represented by the projections. This is possible in view of the Fourier Slice Theorem, which states generally that a projection view of an imaged subject is related by Fourier transformation to the spatial structure of the subject. More specifically, and with reference to the canonical form of the Fourier Slice Theorem for parallel beam projection data, the Fourier transform of a parallel projection at a given view angle $\theta$ is equivalent to a one-dimensional "slice" of the two-dimensional Fourier transform of the imaged subject, taken at the same angle $\theta$ in the frequency domain.

The Fourier Slice Theorem allows the image to be reconstructed by Fourier transforming the projection views, assembling the transforms into a two-dimensional Fourier transform, and applying inverse Fourier transformation to the result. Of course, in practical applications this process may be implemented by some form of filtered back-projection or (for diffracting sources) filtered back-propagation. The salient point is that the reconstruction process relies upon the projection views that are available. It is a commonplace fact that the resolution of the generated image will depend on the spacing of the projection views in $\theta$. the more projection views that are taken, the greater the resolution of the resulting image.

This dependence in CT imaging on data resolution in $\theta$ (angular direction) is the source of a persistent problem that will be termed here the "missing projection views" problem. An insufficient number of projection views for a desired level of image resolution can arise in many situations. For example, the data for some projection views may be corrupted, or the level of desired resolution may exceed the maximum resolution possible with the given discretization in $\theta$.

A typical solution for data corruption is to repeat the entire data acquisition process, i.e., to throw out the entire set of projection data. Further, where $\theta$ discretization has been too coarse, the simplest solution has been to collect more projection views. More data, to provide a finer level of resolution in $\theta$, requires more intensive computation and also entails longer data acquisition cycles. In some situations, constraints imposed by the subject to be imaged, the imaging environment, or the computational resources of the reconstruction engine make denser data collection in $\theta$ (i.e., finer resolution in $\theta$) an unattractive solution at best and frequently one that is unfeasible in practice.

The problem of missing projection views is particularly acute when the subject being imaged, or a relevant part thereof, is in motion. For example, CT x-ray imaging is currently being used for cardiac imaging to detect arterial calcification, which can be an indicator for coronary artery disease. X-ray CT is one alternative among various non-invasive techniques for generating images of a patient's beating heart. Other modalities include Doppler ultrasound, fluoroscopy, magnetic resonance imaging (MRI), and electron beam tomography (EBT). Each modality has its own advantages and disadvantages for a given application context.

For cardiac imaging, x-ray CT has the potential to provide finer spatial resolution in three dimensions, as compared with MRI (especially with multi-row spiral CT). However, current third and fourth generation CT scanners suffer from coarse temporal resolution because of limited gantry speed. This limitation on temporal resolution directly affects the available spatial resolution of the resulting images of the heart. More specifically, in a data acquisition session of practicable length, each phase or distinct configuration of the beating heart will correspond to a few projection views.

For any given phase, therefore, the θ discretization will be unduly coarse and will limit the resolution of the resulting image to an unacceptably coarse level.

Recent developments in image reconstruction algorithms have improved this situation somewhat by enabling CT techniques to achieve much better time resolution than with the standard operation mode. The basic approach of these improved techniques has been to use consistent projection data, collected from multiple heart cycles, and to perform retrospective data rebinning. Such data rebinning methods have been shown to improve significantly the time resolution of the collected data. In practice, however, existing rebinning methods have been found to introduce some image artifacts due to inconsistencies in the data.

It is therefore apparent that the problem of missing projection views, in cardiac imaging and in other applications of CT imaging techniques, has remained as a persistent obstacle to wider use of CT imaging. In the particular context of cardiac imaging, physicians desire a "freeze frame" capability for medical imaging systems. Such a capability would permit an image to be accurately reconstructed to represent the patient's heart at a selected part of the cardiac pumping cycle.

More generally, what has been needed is a method and system for processing CT projection data to overcome or minimize the effects of missing projection views. Such a method desirably would provide acceptable spatial resolution in the resulting images, without requiring extensive additional data acquisition. In imaging contexts where the imaged object is in motion, such as in cardiac imaging, the method would desirably overcome the artifact problems that have existed with current data rebinning methods. Preferably, the technique would be flexibly applicable in a broad range of CT imaging contexts.

BRIEF SUMMARY OF THE INVENTION

The present invention provides methods, apparatus, software, and systems for generating additional projection views based on existing projection data and indirect relationships between the existing data. For example, such indirect relationships may exist in timing relationships between an imaged subject in a desired state and projection data representing the imaged subject in nearby states.

In a first particular aspect, the present invention provides a tomographic image generation method, and a corresponding apparatus, system and software. An exemplary implementation of this aspect of the invention is a method comprising determining a plurality of working projection views of an object at a selected view angle based on initial projection data collected in respective different data acquisition cycles. The exemplary method further comprises interpolating between the working projection views to generate an interpolated projection view of the object at the selected view angle.

In a second aspect, the present invention may be directed toward methods, apparatus, systems, and software for generating a tomographic image of an object in cyclical motion. An exemplary method of this second aspect comprises determining a plurality of working projection views of an object in cyclical motion based on initial projection data collected from the object. The working projection views are based on selected initial projection data collected in respective different data acquisition cycles. The exemplary method further comprises interpolating between the working projection views to generate an interpolated projection view representing the object at the selected view angle and at a specified phase of the cyclical motion.

In a third aspect, the present invention provides a method, apparatus, and software for tomographic image generation. An exemplary method of this third aspect of the invention may comprise determining separation measures for projection data covering corresponding reconstruction ranges and representing an imaged object over plural data acquisition cycles. Such an exemplary method further comprises reconstructing a tomographic image of the object based on a portion of the projection data covering a reconstruction range selected responsive to a determination that the corresponding separation measure satisfies a predetermined selection criterion.

BRIEF DESCRIPTION OF THE DRAWINGS

These and other aspects and advantages of the invention will become apparent and more readily appreciated from the following detailed description of the preferred embodiments, taken in conjunction with the accompanying drawings of which.

DETAILED DESCRIPTION OF THE INVENTION

The present invention implements a different perspective on CT projection data, whereby a broader range of information contained in the data is recognized and used. Previous approaches to processing projection data, such as the aforementioned data rebinning techniques, have used data substitution to overcome partially the problems caused by missing projection views. In other contexts, interpolation methods have been applied to projection data to accommodate changes in the sampling grid.

However, previous methods for processing projection data have failed to recognize that distinct projection views from the same data acquisition session may contain additional information that can enhance image resolution. Such additional information may be contained in the differences between the corresponding projection data values of the respective projection views. The present invention embodies the realization that selective combination of different projection views can extract this additional information for use in improving the resolution of the generated images.

In a preferred embodiment, the present invention provides an improved processing method that achieves the objectives of previous data rebinning approaches for CT projection data collected from multiple cardiac cycles, while avoiding many of the image artifacts that have accompanied such previous approaches. The result of the invention is improved image quality and reduced artifacts for reconstructed images at arbitrary heart phases.

Figure 1:
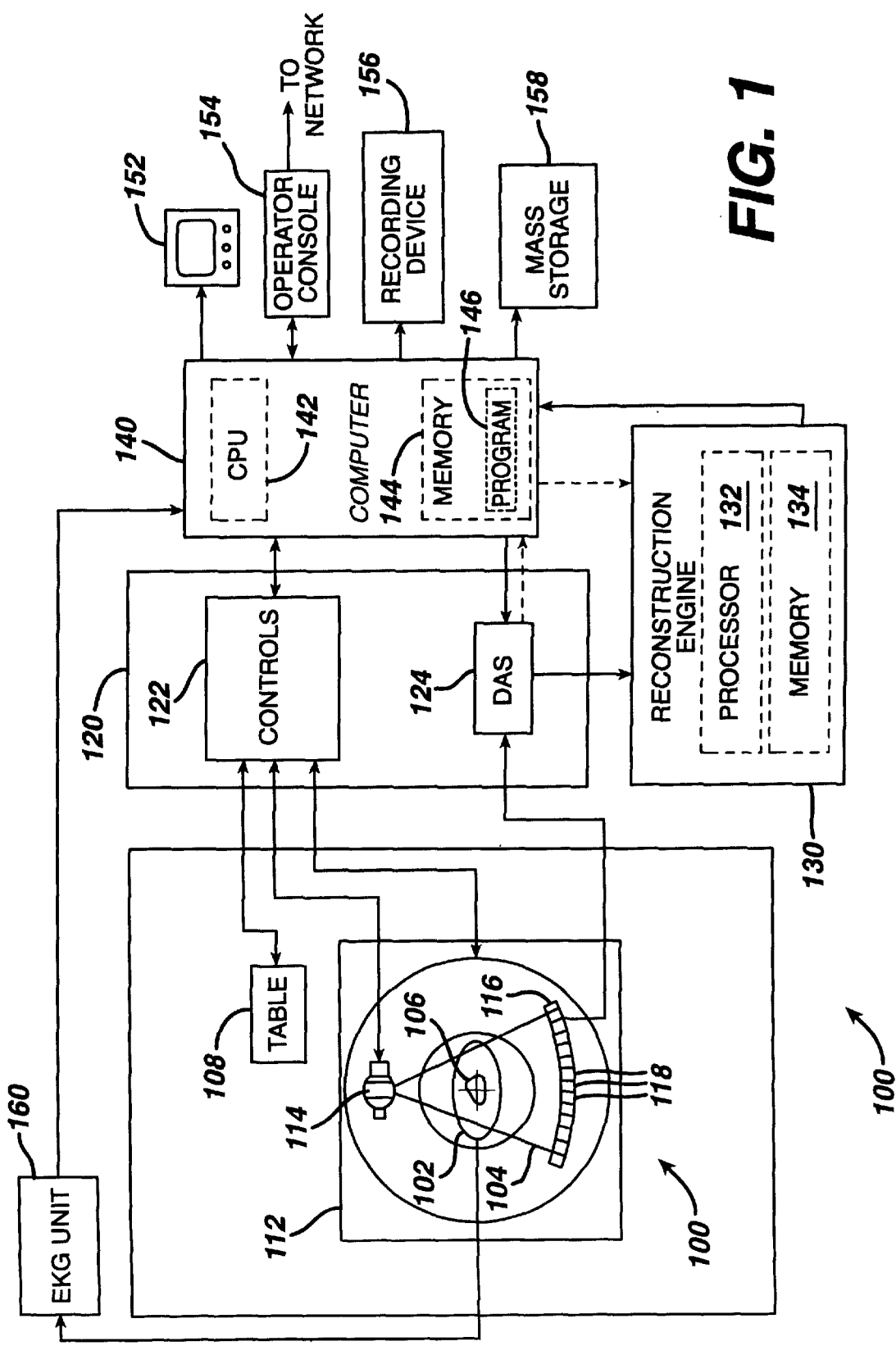
FIG. 1 is a block diagram of a general x-ray CT scanning system in which the present invention may be implemented.

FIG. 1 is a schematic illustration showing the major components of an x-ray CT imaging system 100 in which the present invention may be embodied or incorporated. A subject 102 for imaging is typically a human patient who may be undergoing diagnostic assessment for coronary artery disease or other disease processes. Alternatively, the subject 102 may be a veterinary patient (i.e., a non-human animal) or even a non-animal subject such as an inanimate object (machine part, material sample, etc.) undergoing nondestructive testing or evaluation.

As is well known, x-ray tomographic imaging with such an imaging system 100 is typically carried out by illuminating the subject 102 with an x-ray beam 104 substantially transverse to an axis (shown by cross-hairs) through the subject 102. Typically the axis is centered on an object 106 of interest, such as an organ or other tissue structure. The subject 102 may be disposed on a table 108 that translates along the direction of the axis, thereby enabling illumination of a volumetric portion of the subject 102 by the x-ray beam 104. In the typical case the illuminated volumetric portion comprises all or a relevant portion of the object 106 of interest within the subject 102.

The CT system 100 desirably comprises a source-detector assembly 110, which in an exemplary embodiment may comprise a gantry 112 rotatable about the axis. An X-ray source 114, such as a typical X-ray tube, may be mounted on the gantry 112 and may rotate with rotation of the gantry 112. Source 114, which may comprise a collimating element (not shown), projects the beam 104 of x-rays toward a detector array 116 disposed opposite the source 114 relative to the gantry 112.

The detector array 116 is typically comprised of numerous individual detector elements 118. An alternative term in the art for an array such as detector array 118 is "a multi-channel detector." It will be understood that either term is intended to mean a multiple-channel detection device usable in a computed tomography system.

Detector elements 118 together provide information regarding the internal structures of the subject 102, such as the object 106. As noted above, the subject 102 may be a human patient or an animal patient. In either of these cases, the object 106 may be an organ or body part of the subject 102 and thus is the "object" for purposes of the tomographic image. In a still further alternative application, the subject 102 may itself be the object 106 being subjected to, for example, nondestructive testing or examination.

In the typical case, each detector element 118 generates an electrical signal indicating the intensity of a portion of the x-ray beam 104 impinging thereupon. Various alternatives for the specific arrangement of the source-detector assembly 110 will be described with reference to FIGS. 2–3 and 21.

The signals from detector elements 118 may indicate a degree of attenuation of the beam 104 as the x-rays traverse the material or substance of the subject 102. Typically the source 114 is rotated around the subject 102 to execute a so-called "scan" operation whereby the system 100 acquires x-ray data. The gantry 112, with source 114 attached to a side portion thereof, typically rotates about the axis of the subject 102 to acquire x-ray data from numerous different illumination angles or "view angles."

The rotation operation for the source 114 is controlled by a control/interface system 120. A controls section 122 of the control/interface system 120 provides control for positioning of the gantry 112 relative to the subject 102, such as controlling speed of rotation about the axis and control of relative positions of the table 108 and the gantry 112. The controls section 122 also typically provides control over x-ray generation (power and timing) of the source 114. The control/interface system 120 also includes a data acquisition system (DAS) 124 that samples the detector signals generated from the detector elements 120 and converts the sampled signals into digital data for further processing.

A reconstruction engine 130 receives the sampled and digitized data (now termed "projection data") from the DAS 1124 and performs high-speed image reconstruction. The reconstruction engine 130 may comprise a separate processor 132 and memory 134. Various algorithms are known in the art for reconstructing a slice image from projection data comprising a plurality of projection views.

The reconstruction engine 130 sends the reconstructed image to, for example, a system management computer 140 for storage, display, or further processing. The computer 140 typically comprises a CPU (a processor) 142 and a memory 144. The memory 144 may store a program 146 comprising instructions for executing a process of the present invention. Alternatively, such a program 146 may be executed (in whole or in part) by the reconstruction engine 130 or by another computer system (not shown) comprised in or coupled to the imaging system 100.

The computer 140 may display the reconstructed image on a display 152 in response to instructions from an operator console 154. Computer 140 may also convey commands and scanning parameters from the operator console 154 to the control/interface section 120. Alternatively, the image may be output to a recording device 156, such as a film recorder, or stored in a mass storage device 158. Alternatively, the image may be transmitted as image data over a network (not shown) for disposition at another location. If the computer 140 stores the image in the storage 158, the image data may be stored as a data array, a linked list, or any other known data storage configurations as are well known in the art.

An aspect of the present invention provides a tomographic imaging system with the capability to generate accurate tomographic images of an object in motion. Such an imaging system may therefore comprise a system or apparatus for acquiring timing data by which the projection data collected by the system may be correlated in time with the motion of the imaged object. For example, the system 100 may be used to generate tomographic images of a patient's heart while the heart is beating. A timing data acquisition system for the imaging system 100 may therefore comprise an electrocardiogram such as an EKG unit 160 shown in FIG. 1. The EKG unit 160 detects electrical activity of the patient's heart and provides to the computer 140 timing information based on the detected electrical activity. For example, the timing information may be digital electrocardiographic data. The construction and use of electrocardiograms is well known to those of skill in the art and will not be presented in detail here.

The different functions of control/interface system 120, reconstruction engine 130, and computer 140 are desirably implemented on dedicated modular platforms, as described. However, the division of functions described herein is for purposes of example and is not intended to be limiting. Such functions may alternatively be implemented in software, on a single computational platform, or in a different arrangement on multiple hardware platforms.

Figure 2:
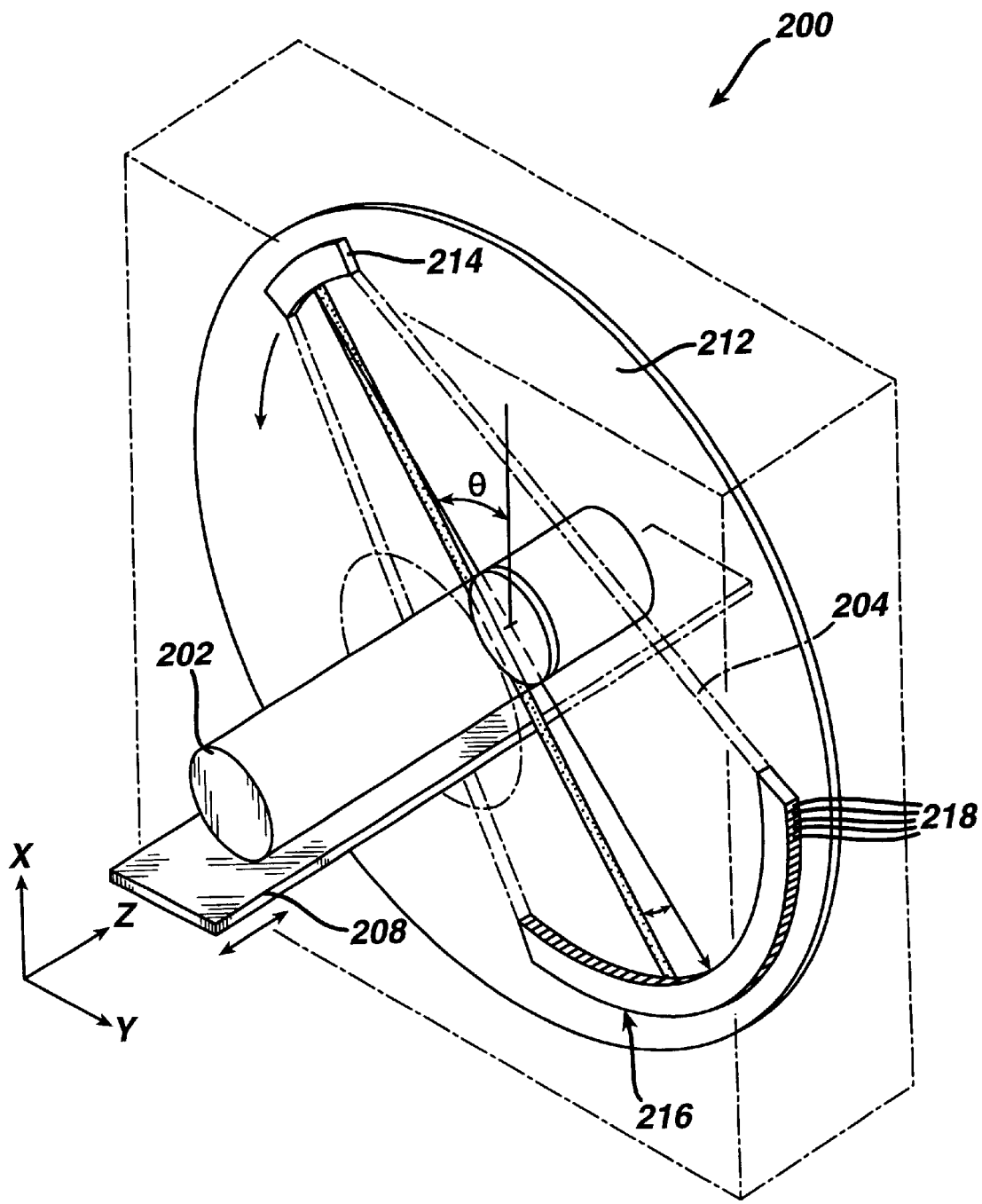
FIG. 2 is a diagram of a third generation source detector assembly for a CT scanning system as shown in FIG. 1.

FIG. 2 illustrates a source-detector assembly 200 as a specific embodiment of the source-detector assembly 110 shown schematically in FIG. 1. An imaging subject 202 corresponds to the subject 102 in FIG. 1. Assembly 200 illustrates the particular case of a so-called third generation "fan beam" CT system in which the subject 202 is illuminated by a beam 204 while positioned on a motorized table 208. The beam 204 may be a "fan beam," as described below.

A gantry assembly 212 corresponds to the gantry 112 of FIG. 1. An x-ray source 214 generates the fan beam 204 of x-rays directed toward a detector array 216, which is also affixed to the gantry assembly 212. Array 216 comprises individual detector elements 218 that detect x-rays emitted by source 214. The array 216, source 214, gantry 212, and table 208 of the fan beam assembly 200 are respective instances of the array 116, source 114, gantry 114, and table 108 as shown in FIG. 1.

In operation, assembly 212 rotates around the axis Z, which typically passes through subject 202 and is perpendicular to the plane XY. Source 214 can thereby be transported completely around subject 202 along a circular path. Detector array 216, being fixed with respect to source 214, is also transported around subject 202 and thus remains opposite source 214.

Rotation of the gantry assembly 212 around the subject 202 results in x-ray data being generated by detector elements 218 for a range of view angles θ. A typical detector array 212 may comprise several hundred, such as 888, individual detector elements 218. The array 216 may be positioned on the gantry 212 at a distance of, for example, 0.949 meter (m) from the source 214. The circular path of source 214 has a radius of, for example, 0.541 m. Particular values of these parameters are not critical to the present invention and may be varied according to well-known principles of CT system design.

One complete gantry rotation for the gantry 212 may comprise, for example, 984 increments. Source 214 is thereby positioned to illuminate the subject 202 successively from 984 different directions θ. Detector array 216 generates x-ray data at each incremental position θ, from which projection data for 984 projection views may be generated.

Figure 3:
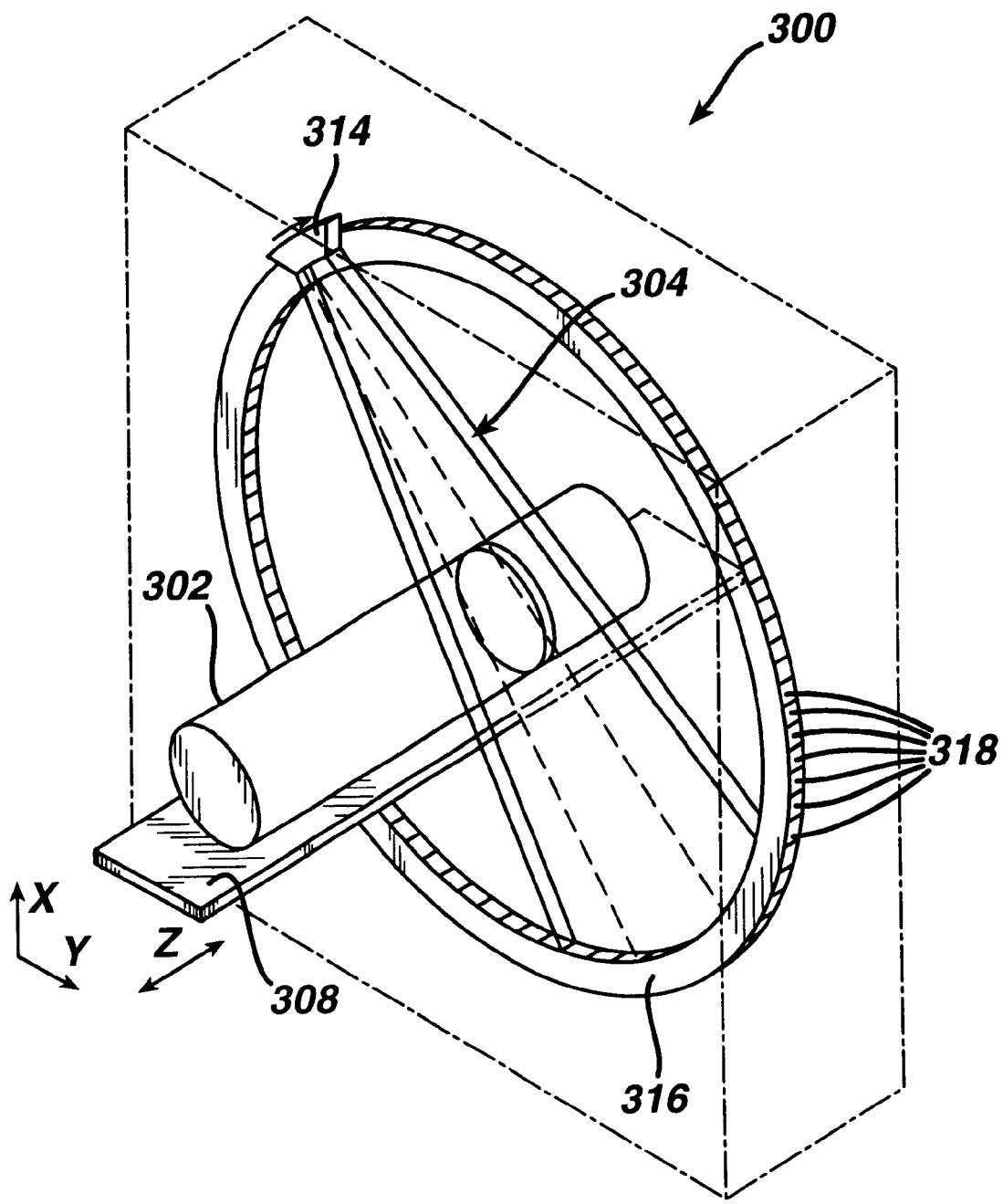
FIG. 3 is a diagram of a fourth generation source detector assembly for such a CT scanning system.

FIG. 3 illustrates a source-detector assembly 300 for a so-called fourth generation CT system. A subject 308 is again illuminated by a fan beam 304 while positioned on a motorized table 308. An x-ray source 314, like source 214 and as a further example of source 114, generates the fan beam 304 of x-rays directed toward a detector array 316. The array 316 comprises detector elements 318 that generate x-ray data indicating internal structural information about the subject 302.

The fourth generation case of FIG. 3 differs from the third generation case, in that the detector array 316 is fixed with respect to rotation. The source 314 is supported by a suitable guide mechanism (not shown) and typically traverses a circular path around the subject 302. The detector array 316 may translate axially (in the Z direction) to provide x-ray data for a particular axial position. Alternatively, the array 316 may be fixed axially as well as rotationally, and positioning of the subject 302 with respect to the detector array 316 and source 314 may be achieved entirely by axial translation of the table 308.

As FIG. 2 shows, a typical third generation CT scanning system performs an axial CT scan by rotation of the gantry around the subject to be imaged. The detector data are collected as the gantry rotates the source and the detector array together. The projection data are thereby generated for different angular positions (i.e., view angles) of the gantry. A fourth generation system comprising an arrangement such as the assembly 300, shown in FIG. 3, differs in that the detector array is usually stationary (at least rotationally) with respect to the subject. The source then traverses a path around the subject and thereby projects imaging rays at different angles for detection by different portions of the fixed array.

On the other hand, both the assembly 300 and the assembly 200 may use a fan beam (204 or 304). A "fan beam" is a fan shaped beam of radiation, i.e., a beam subtending a finite angular sector in a given plane. Usually the fan is thin, where "thin" refers to the direction transverse to the fan plane, e.g., a direction generally parallel to the axis Z. X-rays in the angular sector actually subtended by the fan beam may not all be used for generation of detector data. Thus, an effective portion of the fan beam may subtend a smaller angular sector whose angular extent is called the "fan angle" of the fan beam. In the arrangements of FIGS. 2 and 3, the plane of the fan beam is transverse (typically perpendicular) to the axis Z at a fixed axial position.

A rotational scanning operation performed at a fixed axial position is sometimes called an "axial scan." The axial scan is carried out with rotation of the source (or the source and detector together) about the subject at a fixed axial position z0. Therefore, the projection data from an axial scan all represent the imaged subject at the same axial position $z_0$.

The present invention provides an approach for enhancing resolution and image quality of a CT image without requiring additional detectors or additional data acquisition and generally may be applied to axial CT systems (e.g., third generation and fourth generation systems). The invention may also be used with less advanced (e.g., first or second generation) source-detector arrangements. Moreover, as will be explained below, the invention may be embodied in or implemented with spiral (i.e., helical) CT imaging systems. The basic features of the invention will be explained first in the axial CT context and then extended, with appropriate enhancements, to the helical case.

It is noted that similar operations of rotation apply in both third generation and fourth generation systems for the acquisition of detector data during a complete cycle of the source-detector assembly. In the axial scanning case, the data acquisition cycle is called an axial scan. More generally, the principle of a rotational cycle of data acquisition is generally applicable in all such x-ray CT scanning systems. The term "scanning rotation" will therefore be used here to mean the rotational operation for positioning the x-ray source (e.g., source 214 or source 314) at each angular position θ around an axis of rotation and collecting corresponding data. "Scanning rotation set" will mean the set of projection data generated from a scanning rotation. Where no confusion will arise, the term "scanning rotation" will be used variously to mean either the data acquisition operation or the projection data set generated as a result of the data acquisition operation.

Typical x-ray CT systems (e.g., third generation systems and fourth generation systems) are an exemplary class of tomographic imaging systems. For example, magnetic resonance imaging (MRI) systems also are used to generate tomographic images by a data collection and image reconstruction process that may be termed (in a generalized sense) computed tomography.

Cardiac imaging can be performed with some MRI systems by processing a series of magnetic echo data sequences with various types of gating techniques. In prospective spin echo gating, for example, the system acquires imaging data over a series of cardiac cycles. An additional sequence of spin echo data is acquired at each cycle. Each spin echo data sequence represents the heart at different spatial locations but is acquired during the same cardiac cycle and with the same k-space encoding value. Thus, the data collection operation for acquiring such a spin echo data sequence is analogous to the scanning rotation operation in x-ray tomographic imaging. In each case, the operation is a data sampling cycle for acquiring a consecutive sequence of data samples over a cycle interval.

Also, retrospective gating of gradient echo pulse sequences is used in MR systems to acquire "cine" images at multiple time frames of the cardiac cycle. Data acquisition again occurs over several cardiac cycles, and in each acquisition cycle the data samples have the same phase (i.e., k-space) encoding value. The phase encoding value is thus stepped to a next value at each successive R-wave trigger. The excitation pulses run asynchronously with the cardiac cycle, so that the echo pulse data acquired in each sampling cycle is resorted and interpolated into evenly distributed time frames within the cardiac cycle. Nevertheless, like rotational scanning in x-ray systems, the sample data are again acquired in a series of sequences of data samples acquired consecutively over a sampling cycle interval.

These examples illustrate a general principle of data acquisition in tomographic imaging systems: the imaging data are acquired in one or more sequences of data samples. Here, the term "data acquisition cycle" will mean a data acquisition operation for obtaining such a sequence of data samples at a sequence of consecutive sampling times. Thus, in existing approaches to x-ray tomography the data acquisition cycle is the scanning rotation (which may be carried out by gantry rotation or source rotation, for example). For MRI systems, the data acquisition cycle may be the sequence of measurement operations in which the magnetic field gradients are varied according to the particular localization method being used. As will be explained in detail, the present invention adopts a different perspective on combining data from different data acquisition cycles.

Data from an axial scan may be stored in a two dimensional array called a "sinogram." One dimension of the sinogram corresponds to angular position of the fan beam (e.g., scanning rotation angle or "view angle" θ), relative to the initial rotational orientation of the beam at the start of the data acquisition cycle. The other dimension corresponds to positions of the detector elements (218 or 318) of the detector array. The detector array in a fan beam CT system (such as array 216 or array 316) typically comprises a single row of detector elements. In such a case, therefore, each row of the sinogram will correspond to a discrete view angle θ and a single axial position z0.

In the fan beam case, the sinogram may be considered as a collection of projection views of the subject at the position $z_0$. Here the term "projection view" means such a row of projection data corresponding to a given view angle θ and representing the imaged subject at a single axial position $z_0$. Well known reconstruction procedures utilize as their principal inputs a complete set of such projection views (discretized in θ, but all consisting of data values for the same axial position $z_0$). The projection views are processed to generate a slice image depicting the internal features of the subject at the position $z_0$. Usually the complete set of projection views comprises projection views at view angles covering at least π radians (i.e., 180 degrees) plus the fan angle.

Figure 4:
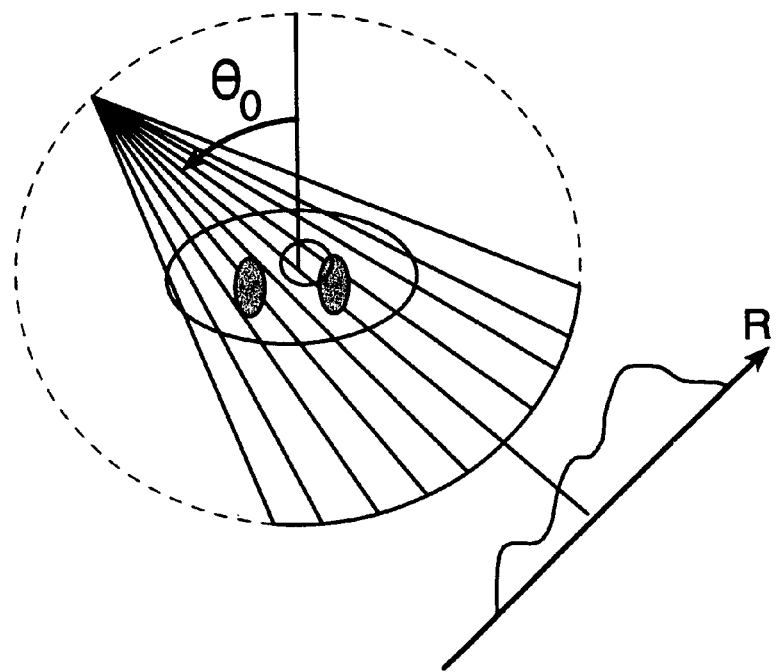
FIG. 4 is a diagram illustrating the correspondence between a particular view angle and generation of a row of projection data.

FIG. 4 illustrates the correspondence between a particular view angle $\theta_0$, for the source and the generation of a well-defined row R of projection data. In the fan beam case, as noted above, the detector data from the detect or array may convert directly into a single row of projection data for a projection view at view angle $\theta_0$. This correspondence results because the detector array provides a single row of detector data representing intensities of the x-rays impinging upon the detector elements. These intensity values indicate attenuation information for the subject at the axial position $z_0$.

Figure 5:
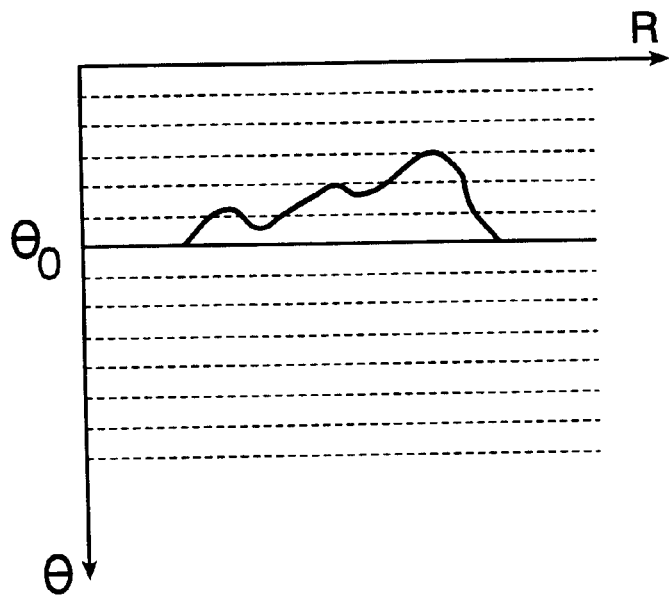
FIG. 5 is an illustration of a sinogram of projection data including the row of projection data of FIG. 4.

FIG. 5 shows how the projection data for the particular view angle $\theta_0$ is stored in a corresponding row of the sinogram. Each row of the sinogram thus constitutes a projection view that indicates attenuation information for a distinct view angle $\theta$, but the same axial position $z_0$. Once the sinogram is filled with projection views (rows) for all the discrete view angles $\theta$ around the subject, then a suitable CT image reconstruction algorithm is applied to reconstruct a cross-sectional image of the subject.

Figure 6:
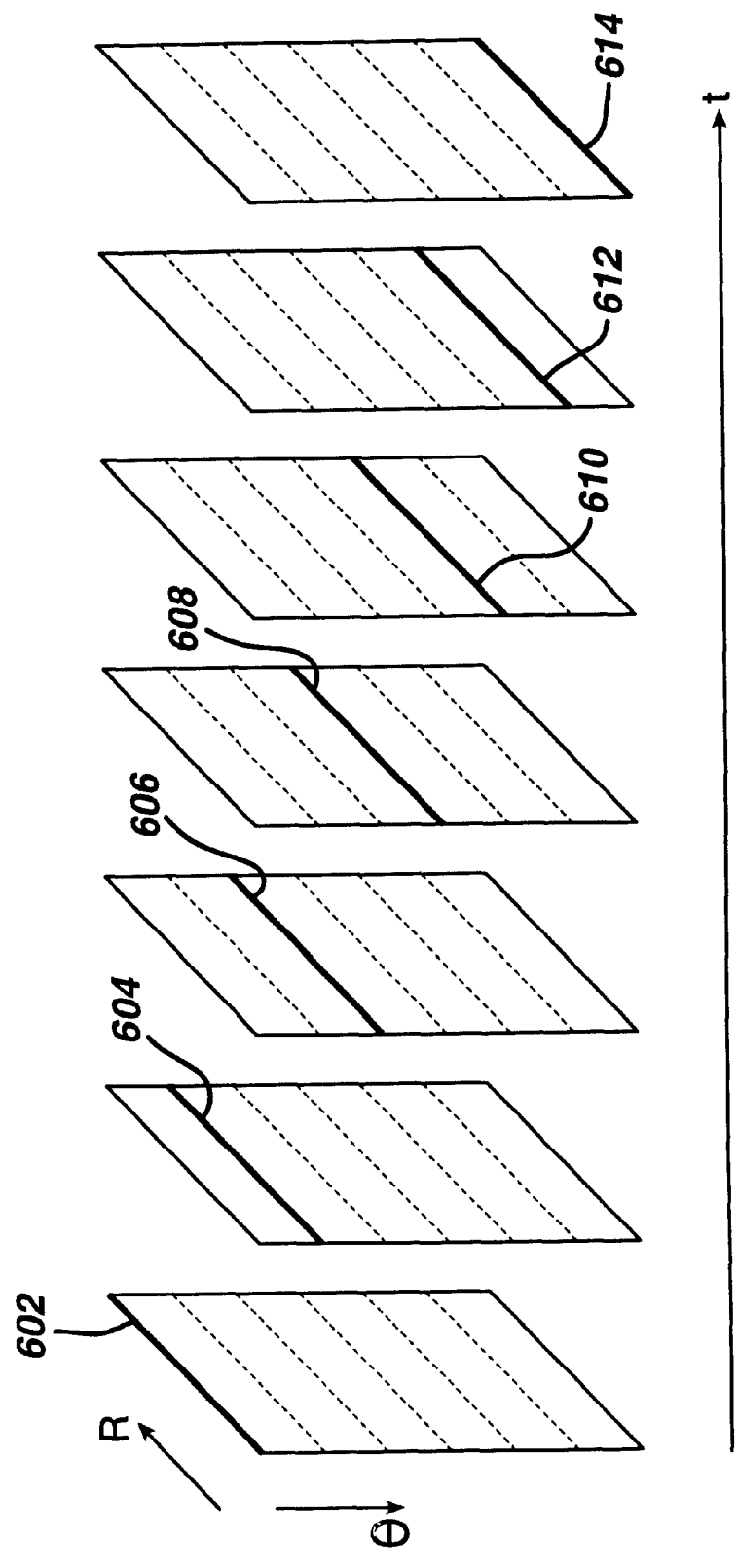
FIG. 6 is a diagram illustrating a time dependent feature of sinogram data.

FIG. 6 illustrates a time dependent feature of the projection data stored in the sinogram. The view angle $\theta$ of the source relative to a fixed direction can be written as $$\theta(t)=\omega t,$$

where $\omega$ represents the angular speed of the gantry in radians per second and t denotes time. Each row R of the sinogram therefore represents information about the subject (at the axial position $z_0$) at a different time t.

Usually the fact that the rows of the sinogram are time dependent is inconsequential, because the subject is immobile during the scanning process. The assumption of stasis may be reasonable even for a living patient, because the patient can be well constrained during the time it takes to collect all the projection views (0.5–0.8 seconds). For example, when the area of interest is the patient's head, abdomen, etc., the body part of interest can be assumed to be stationary during the scan.

However, in cardiac imaging the assumption of stasis clearly does not apply, at least for a living subject. The beating of the patient's heart persists and cannot be suspended. Moreover, a heart rate of 72 beats per minute (bpm), for example, corresponds to 0.83 seconds (s) per beat. The heart thus completes a full cardiac cycle in a time span comparable to the time required for collecting projection views at all the view angles $\theta$. The beating heart thus undergoes a substantial portion of a complete cardiac cycle while the projection data for a slice image are being obtained.

The particular motion that affects cardiac CT imaging is largely the cyclical change in the shape of the heart throughout the cardiac cycle. However, the same imaging problem appears in various situations where the object of interest is in motion during the CT scan process (the data acquisition cycle). The scanner is unable to generate a clear image of the object being imaged at a particular position (e.g., a particular phase of the cardiac cycle) because the object moves too rapidly for a complete set of projection data to be collected while the subject is in the desired position or configuration.

The problem may be analogized to the problem in conventional photography of freezing a subject in motion. If the camera shutter speed is too slow, the subject will undergo a significant amount of motion while the shutter is open (i.e., collecting image data). The resulting image of the subject is blurred. In a like manner, the CT scanning system may be unable to generate a clear slice image, if the subject is in motion while the scan data are being collected. In effect, the CT scanner has a slow shutter speed relative to most rates of motion of the subject.

FIG. 6 thus emphasizes that the collection of projection data proceeds as a function of time while the gantry or source is rotating. A projection data set should be complete (covering as much as 360°, but at least 180° plus the fan angle) to provide a useable tomographic image upon reconstruction. However, if the projection data set consists of projection views from a single scanning rotation, the projection views will respectively represent the heart at many different phases of the cardiac cycle. Each projection view corresponds to a particular row in the sinogram, but is collected at a different moment in time. Strictly speaking, reconstruction of an image at any particular phase of the heart requires collecting all the projection views (all rows of the sinogram) at that particular instant in time. This would require a very fast data acquisition cycle (i.e., a very fast shutter speed for the CT scanning system).

A feasible solution to this problem can be achieved by making use of the cyclical nature of the cardiac cycle (more generally, any repeating feature of the motion of the object of interest). As the cycle repeats, the beating heart moves through the same cycle of shapes and assumes successive shapes in an ordered sequence in time. Multiple scanning rotations, together with data gating, can be used to collect several projection views corresponding to the same phase from multiple heart cycles. The CT scanning system can thereby generate the projection views to be used in reconstructing an image of the beating heart at a particular heart phase.

Unfortunately, obtaining all the desired projection data directly through respective data acquisition cycles would entail an inordinately large number of scanning rotations for the corresponding projection views. The "shutter speed" problem arises here in a different form: although the heart regularly repeats the cardiac cycle, the subject being imaged otherwise desirably remains stationary throughout the data collection process. A reasonable number of scanning rotations, during which the subject can be expected to remain generally stationary, will provide just a few projection views of the heart at a given phase.

Figure 7:
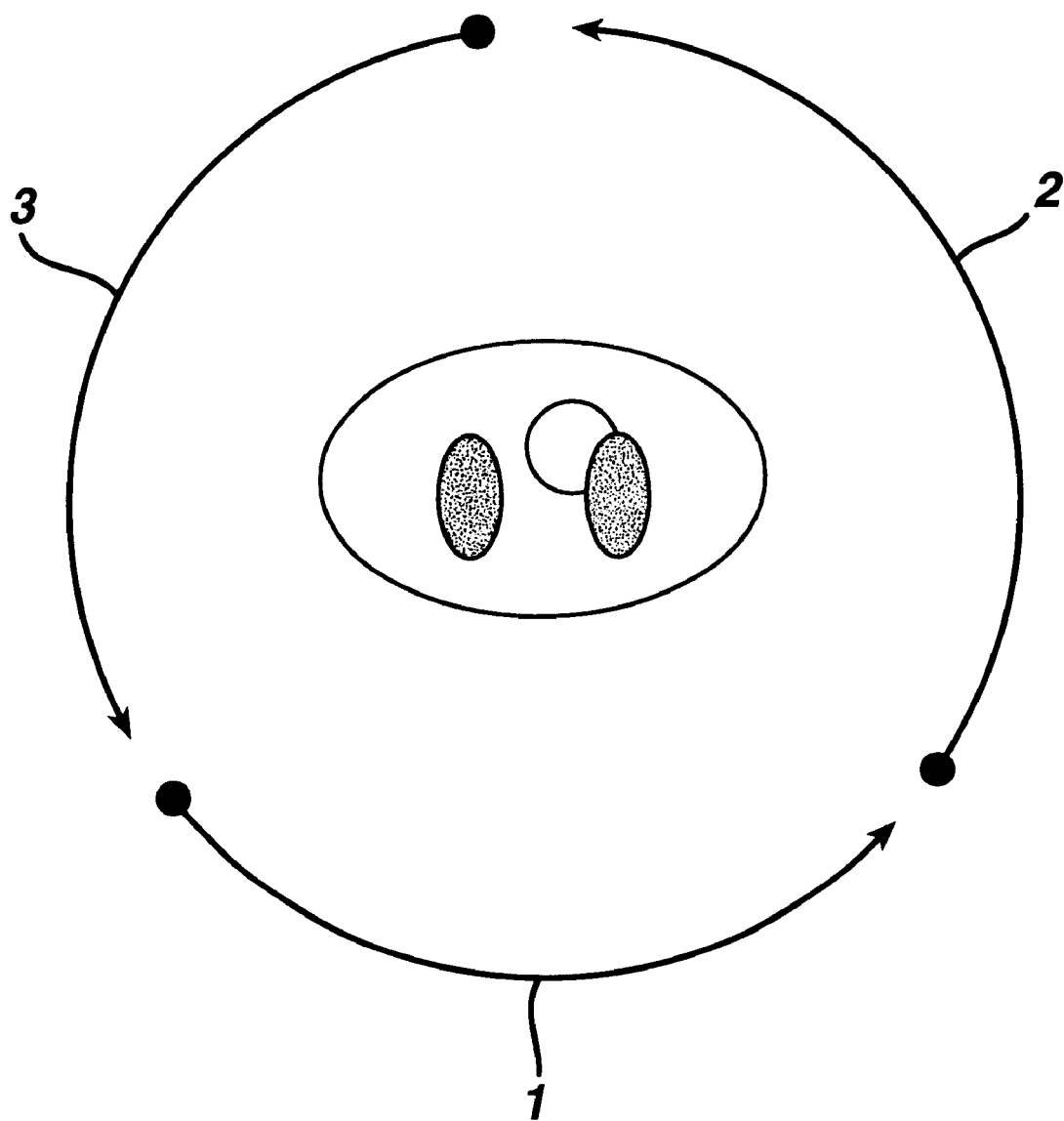
FIG. 7 is a schematic diagram illustrating a sector approach for rebinning data in cardiac imaging applications.

FIG. 7 illustrates this problem through a simplified example in which three projection views are collected at the desired heart phase, $t=\phi_0$. It is noted that phase $\phi$ is measured in units equivalent to time t. Here a distinct symbol ($\phi$) is used for phase to emphasize the periodicity of the heart motion, because periodicity is a dynamical feature not present in dynamic phenomena generally. The three views correspond sequentially to heart cycles 3, 1, and 2 as shown and may be collected in, for example, three scanning rotations. At 0.5 s per scanning rotation, even this level of data collection requires the patient (the imaged subject) to remain stationary for at least 1.5 s.

The following scheme has been partially successful in overcoming the persistent problem of missing projection views in the context of cardiac imaging. An assumption is made that, at least for some phases to of the cardiac cycle, the heart motion may be relatively slight in the neighborhood of $t=\phi_0$. As FIG. 7 shows, the heart cycle is divided into a few phase sectors, in each (or at least some) of which the heart is assumed to be close to stationary.

For each scanning rotation of the CT system, the phase sectors of the cardiac cycle can be associated with angular sectors of the rotation. Data for projection views at many different view angles are collected in each scanning rotation. If the foregoing assumptions are valid, then from all the scanning rotations the data corresponding to the phase sector of the desired phase can be used for reconstruction of an image of the heart at the desired to phase.

The approach described above has been termed data "sectoring" or "data segmentation" and has been implemented successfully in various contexts. For example, U.S. Pat. No. 5,997,883, issued Dec. 7, 1999, to Epstein et al. and assigned to the assignee of the present application, discloses a cardiac imaging technique using segmented MRI cardiac data. Data segmentation has been shown to yield x-ray CT images with image quality satisfactory for many purposes. On the other hand, such CT images suffer from certain noticeable artifacts, such as streaks. The artifacts in these images are believed to be due to inconsistency of the projection data, particularly in the regions of transition between the different sectors, because the different projection views actually represent the heart at somewhat different cardiac phases.

Figure 8:
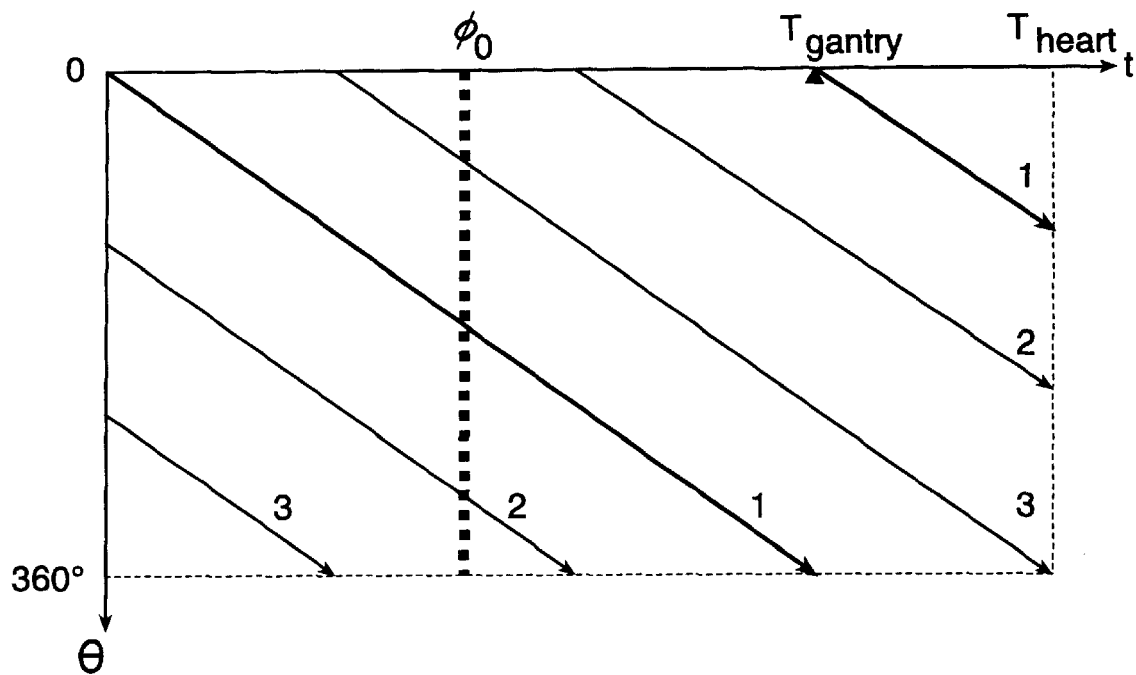
FIG. 8 is a diagram depicting a different perspective of the time dependent characteristics of sinogram data as provided by the invention.
Figure 9:
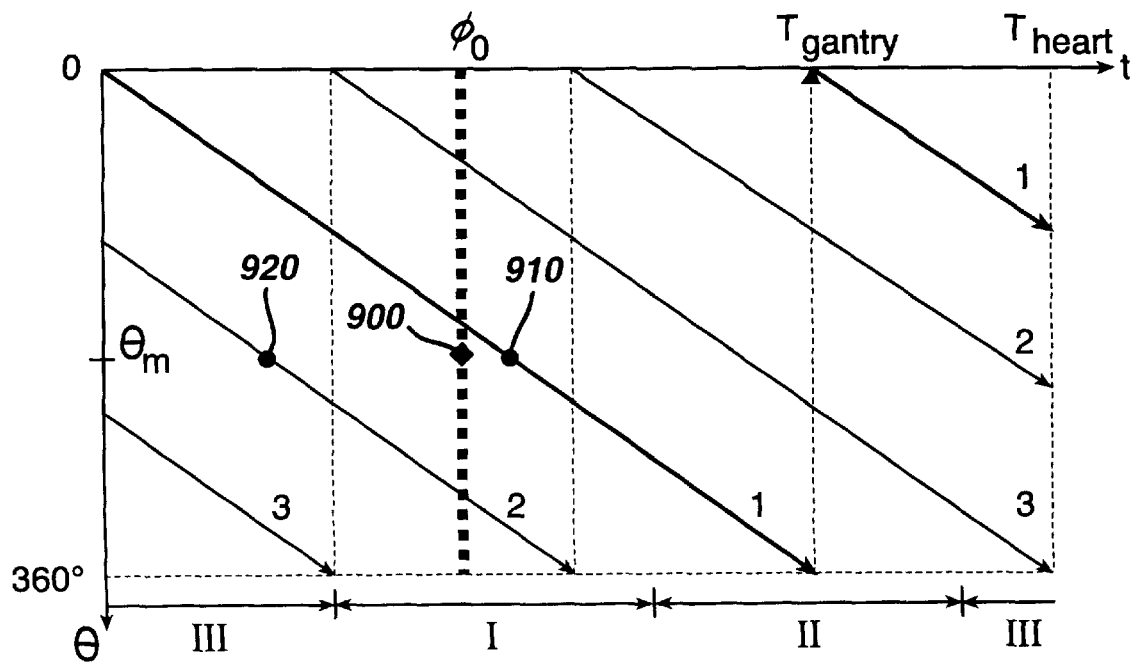
FIG. 9 illustrates contrasting features of the sector approach of FIG. 7 and the perspective provided by FIG. 8.

FIGS. 8–9 illustrate analysis of sinogram data through a different perspective that constitutes an aspect of the present invention. The diagonal trajectories 1, 2, and 3 in FIG. 8 illustrate the time dependence of the sinogram data, as shown previously in FIG. 6. Thus, each trajectory (1, 2, or 3) represents a sequence of sinogram rows as $\theta$ evolves in time. FIGS. 8–9 depict the trajectories as continuous diagonal lines, for purposes of illustration. However, like the sinograms they represent, these trajectories actually represent the sinogram data as comprising projection views corresponding to a discrete sequence of view angles $\theta$.

If the period of the cardiac cycle and the period of the data acquisition cycle are different, projection views can be collected corresponding to different phases of the heart during each rotation. Here $T_{gantry}$ and $T_{heart}$ correspond to scanning rotation period and cardiac cycle period, respectively. For description purposes, the particular example of FIG. 8 illustrates the case where $T_{gantry}$ is less than $T_{heart}$. However, and the present invention readily applies also to the case $T_{gantry}$ greater than $T_{heart}$.

The data trajectories are indicated in FIG. 8 by diagonal lines with arrows and represent the projection data in the $\theta$-t domain. It is noted that $\theta=0°$ and $\theta=360°$ actually represent the same angular position. Hence each trajectory in FIG. 8 wraps around to 0° whenever $\theta$ reaches 360°. Further, because $T_{gantry}<T_{heart}$ in the case illustrated, the ordinal extent of the domain is [0, $T_{heart}$), and each trajectory wraps back to t=0 whenever the trajectory reaches t=$T_{heart}$. Each recurrence of t=0 corresponds to a next cardiac cycle, which is represented in FIG. 8 by another trajectory.

The scheme described above assigns projection data for a given view angle $\theta$ from the trajectory nearest to the vertical line at t=$\phi_0$. As noted above, this approach is commonly known as data sectoring or data segmentation. However, in view of the perspective provided by FIG. 8, a more descriptive term may be "nearest neighborhood substitution." The idea is to substitute data from the desired view, but from a nearby phase, in place of the missing projection view for the desired phase.

FIG. 9 illustrates the relationship between the data sectoring approach and the perspective illustrated in FIG. 8. The range of cardiac phases is "segmented," or divided into segments (or "sectors") denoted I, II, and III. The sectors correspond to predetermined portions of the cardiac cycle. In each of the trajectories 1, 2, and 3, the phase sectors correspond to respective angular regions in $\theta$. Hence each of the trajectories 1, 2, and 3 is divided into angular segments corresponding to the phase sectors I, II, and III. FIG. 9 also shows that the phase sector (sector I) of the phase to coincides with different angular segments for the different trajectories. As noted above, the sectoring approach assigns substitute projection data for missing projection views according to the phase sector of the phase to at the desired view angle $\theta_m$.

For example, the view angle $\theta_m$ in FIG. 9 corresponds to a missing projection view 900 for the phase $\phi_0$, because none of the trajectories 1, 2, and 3 pass through the point (in $\theta$ and t) at which the view 900 is desired. The sector approach determines the trajectories within the phase sector of the target phase at the desired view angle and identifies an available projection view at that view angle and on the trajectory nearest in time to the phase to.

In FIG. 9, the projection view 910 is the projection view nearest to the desired phase. The projection data for this nearest neighbor projection view are then substituted for the missing projection view. It is noted that the information associated with other projection views, such as the next nearest projection view 920 in FIG. 9, is completely ignored in the sector approach.

The present invention uses a different perspective of the projection data and of the problem of missing projection views. For a scan where the gantry is continuously rotated, the trajectories in FIG. 8 represent the data collected in the two dimensional domain of view angle versus time ($\theta$ vs. t). This perspective enables the invention to take a different approach for processing the projection data. Instead of block assignment of the data to different phase sectors, the present invention makes use of additional information revealed by representing the projection data as trajectories. In fact, the trajectories allow quantitative relationships between the available data and the desired data to be discovered and utilized.

The perspective adopted by the invention enables the additional information contained in an additional projection view, such as the second projection view 920 in FIG. 9, to be incorporated into projection data for the missing projection view. This incorporation of multiple working projection views into projection data for a missing projection view is achieved through interpolation in the sinogram phase domain, i.e., along the t axis. For a set of (two or more) existing projection views at a given view angle, corresponding data values of the projection views are interpolated to generate a corresponding data value for an interpolated projection view at the given view angle and the desired phase. Here, therefore, interpolation between projection views means to carry out the same relative combination of data values for all the row positions of the set of projection views being interpolated.

Figure 10:
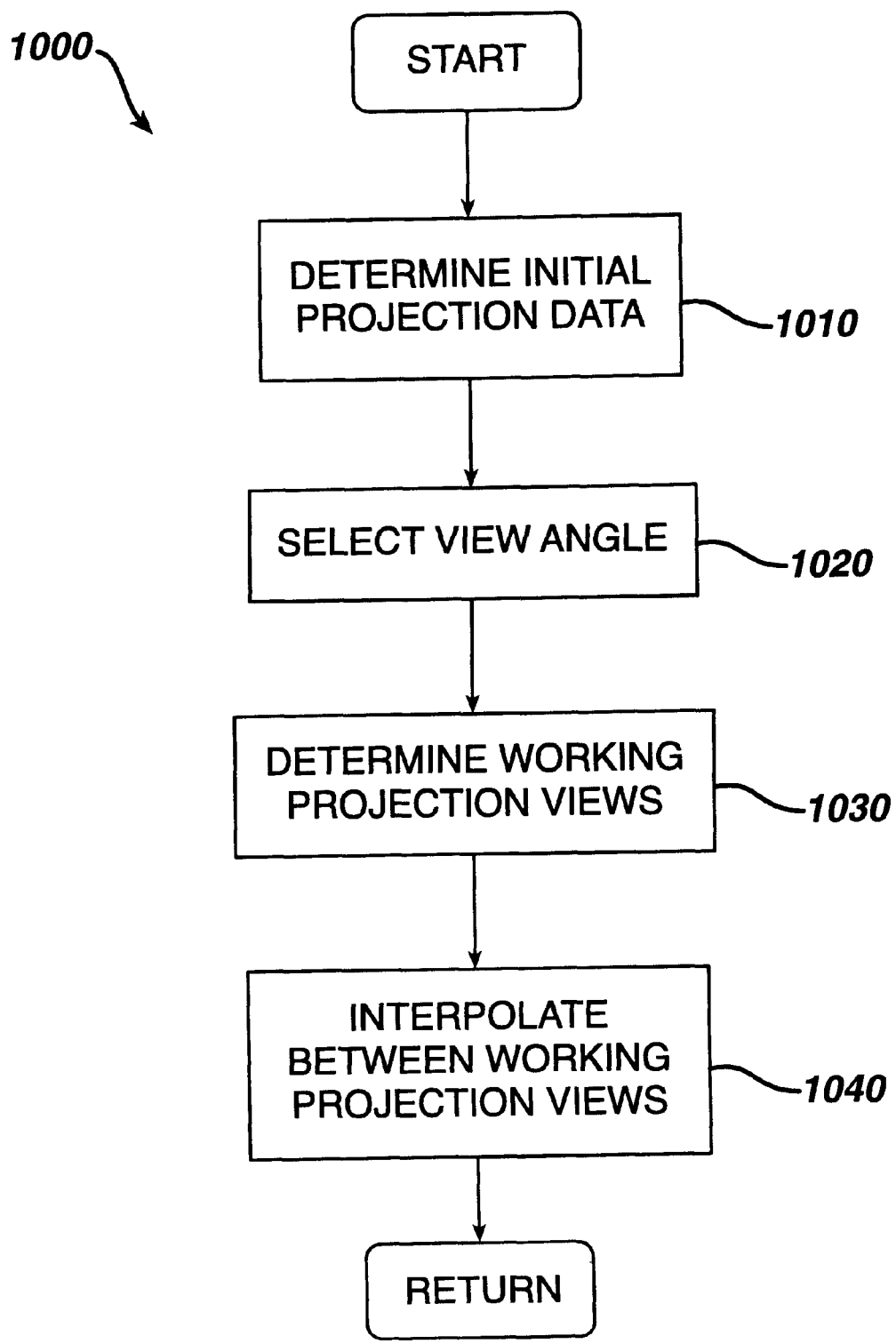
FIG. 10 is a flow diagram illustrating a procedure of the invention.

FIG. 10 shows a flow diagram illustrating an interpolation procedure 1000 of the invention. An operation 1010 determines the initial projection data available. This initial data may comprise, for example, sinograms of projection data providing plural trajectories of projection views accumulated over time, as illustrated in FIG. 8. Such initial projection data may be generated directly by a DAS such as DAS 124 in FIG. 1. Alternatively, as explained below, the initial projection data may be determined from the digitized detector data by rebinning or other preprocessing operations, as are well known in the art.

An operation 1020 selects a view angle for which a projection view is to be synthesized through interpolation. From existing projection views of the initial projection data at the selected view angle, working projection views are determined in an operation 1030. The working projection views will represent the imaged object at the selected view angle, but in different data acquisition cycles. For example, in a particular embodiment of the invention, the interpolation may be performed between two projection views such as views 910 and 920 shown in FIG. 9. In such a particular instance, then, the working projection views are determined as the two projection views that are nearest in time to the desired phase $\phi_0$, among projection views at the desired view angle in the initial projection data.

Interpolation is performed between the corresponding data values of the working projection views in an operation 1040. Any of various different interpolation techniques may be employed for this purpose, as are well known to those of skill in the art. For example, weighted linear interpolation between neighboring data trajectories is a particular interpolation method that has been used effectively. The weights may be computed based on respective timing differences between timings of the selected working projection views and a corresponding timing of the desired projection view. For example, in an implementation of the invention for cardiac imaging, the timings of the working projection views and the desired projection views may be embodied in corresponding phases of the cardiac cycle.

Where the initial projection data comprise data sinograms for cardiac imaging, the sinograms are preferably correlated with simultaneously collected timing data such as electrocardiogram (EKG) data generated by the EKG unit 160 of FIG. 1. The correlation provides a time stamp for each row of detector data. The time stamp of a row of projection data provides an explicit cross reference between the row of data and the shape configuration of the heart (as determined by the EKG data) at the time the row of data was collected.

Figure 11:
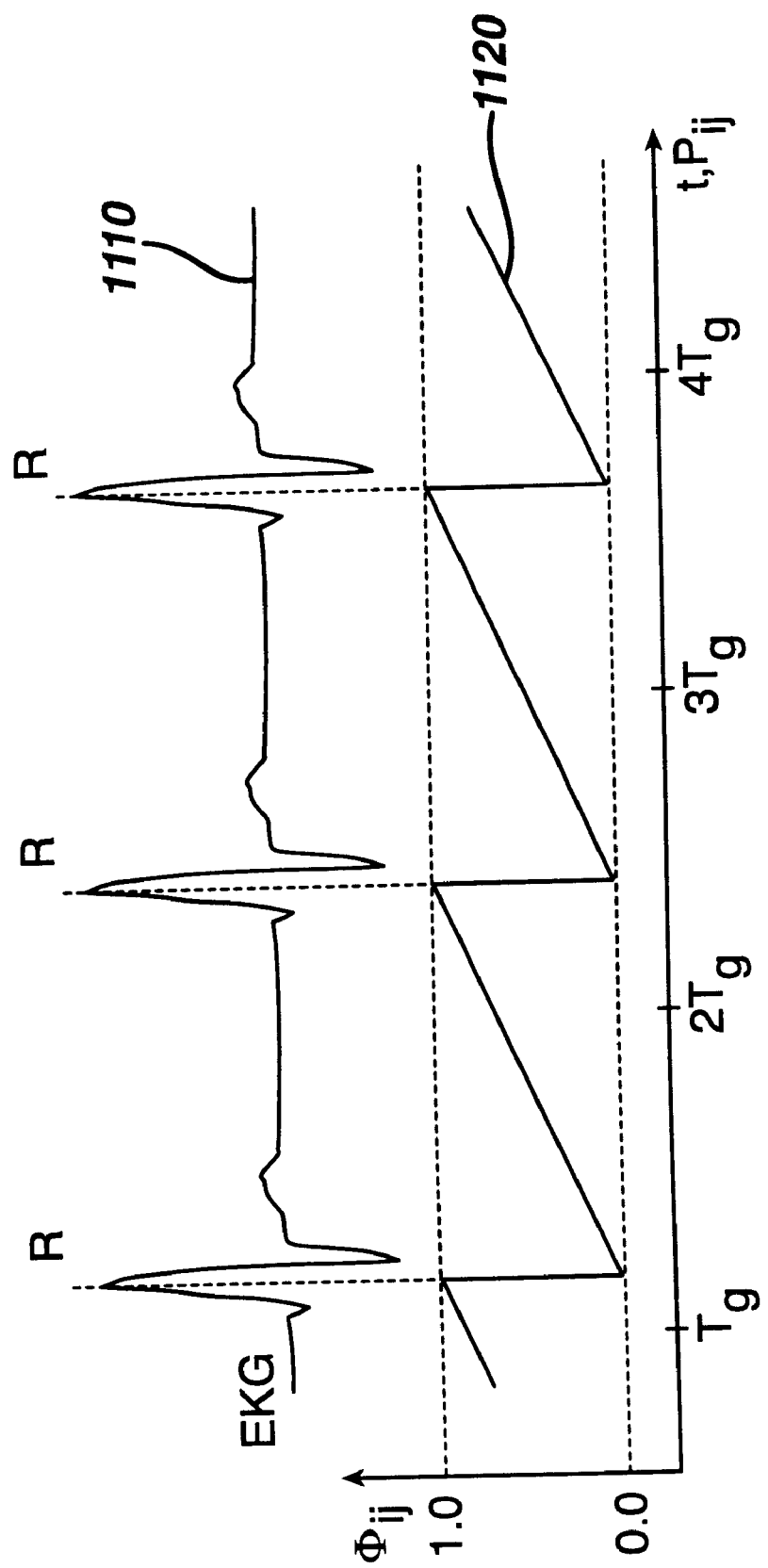
FIG. 11 is a timing diagram illustrating a tagging function for correlation of projection data with corresponding phases of an imaged subject's cardiac cycle.

FIG. 11 illustrates an approach for using such time stamps to correlate the projection data with contemporaneous electrocardiographic data. The EKG data represent an electrocardiograph 1110 of the patient's heart during the tomographic scanning procedure. The projection data represent the heart at various phases of the cardiac cycle and are collected at a known sampling frequency (e.g., 984 projection views in each period of the gantry rotation) that allows the projection views to be time stamped with respective temporal locations.

On the other hand, the projection data do not contain explicit phase information. The contemporaneously collected EKG waveform 1110 can be used to determine such phase information, provided the collection of the EKG data is synchronized with collection of the projection data. The projection data also do not explicitly comprise axial position (Z-location) information, but such position data may be recorded sequentially as each axial scan is performed.

In a particular implementation, for example, the EKG data for the waveform 1110 may be collected during the scanning procedure by the EKG unit 160 and may be digitized at a specified sampling frequency (e.g., 240 samples per second). The particular sampling frequency is not critical to the present invention. The criteria for selecting a suitable sampling frequency are well known to those of skill in the art, and such criteria will not be described here.

The temporal locations of the R-wave peaks of the waveform 1110 may be identified u sing any of various well-known wave for analysis techniques. Using the identified peak locations, a linear phase function 1120 may be defined to increase from 0.0 to 1.0 between each consecutive pair of R-wave peaks.

The function 1120 may be used to map (i.e., to correlate) the phases of the cardiac cycle to the time-stamped temporal locations of the projection views. Each projection view is thereby assigned a cardiac phase $\Phi_{ij}(\theta)$, where the indexes i and j respectively identify the cardiac cycle and gantry rotation of the scanning procedure. It is noted that the cardiac phase assignment $\Phi_{ij}$ may further be associated with specific axial positions, as will be explained below with reference to FIG. 24. The phase function 1120 (defined between all consecutive R-wave peaks of the waveform 1110) thereby allows all the projection views of the projection data to be correlated (tagged) with an associated cardiac phase $\Phi_{ij}$.

In the simplest case, it may be assumed that the heart rate is constant while the scan data are collected. The desired phase (in the case of cardiac imaging, corresponding to a shape configuration of the patient's heart) then occurs in each cardiac cycle at a fixed fraction of the heart period $T_h$ following the preceding R-wave. This assumption of regular heartbeat simplifies the process of cross-referencing the projection data and the EKG data. In particular, for each R-R heart cycle the desired phase of the heart occurs on the vertical line $\phi_0$ in FIG. 8.

An advantage of the foregoing implementation is that a phase function, such as the linear phase function 1120, allows correlation between heart phases and row data to be carried out even when the subject's heart rate is irregular. In either case, the time correlation between the EKG data and the collected scan data may be performed off-line, i.e., after the projection data is initially collected, binned, and time stamped.

The linear phase function 1120 shown in FIG. 11 is only one example of a feasible phase mapping function for EKG data. Other, possibly non-linear phase mapping functions are also feasible for use with the present invention. Such alternative mappings may permit the electrocardiographic behavior of the R-R cycle to be modeled more accurately and in more detail. In turn, more accurate and detailed modeling of the electrical cycle of the heart may permit more accurate time correlation of the heart phases.

Adaptive Projection Data Processing

In a particular embodiment of the procedure illustrated in FIG. 10, the initial projection data may represent a patient's beating heart, and the two nearest projection views may be identified based on the time correlation between the collected projection data and the EKG data. The time stamps of the projection data allow the working projection views to be determined in operation 1030 based on the correlation between the gantry rotation and cardiac cycle. For example, the projection view 910 on trajectory 1 in FIG. 9 may be identified from the timing at which the gantry rotation coincides with the missing view angle $\theta_m$ and the assigned phases $\Phi_{ij}$. The phases $\Phi_{ij}$ of the projection views may be used with the EKG data to determine the phase differences, as will now be explained.

Figure 12:
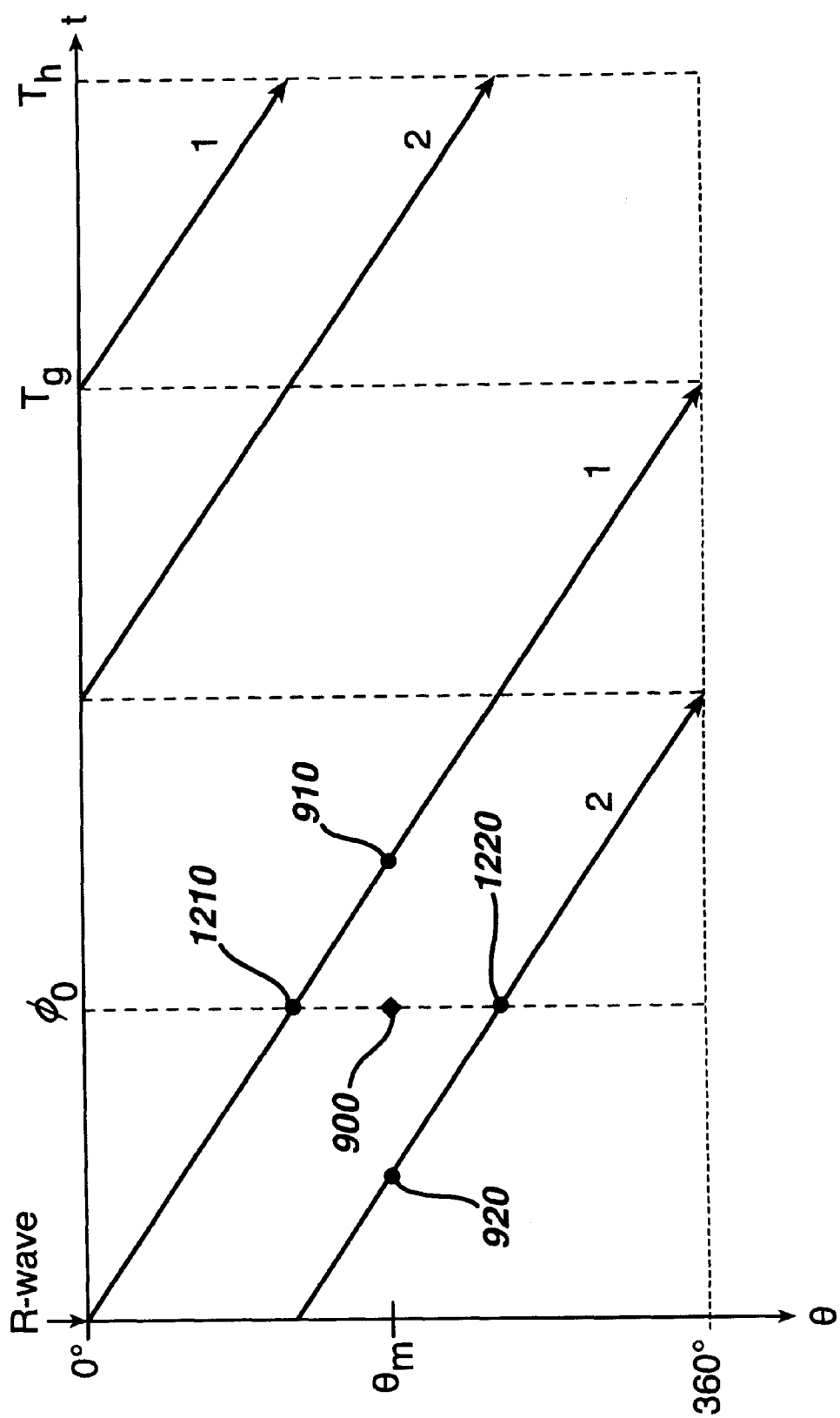
FIGS. 12–13 are diagrams illustrating an application of the present invention in cardiac imaging.
Figure 13:
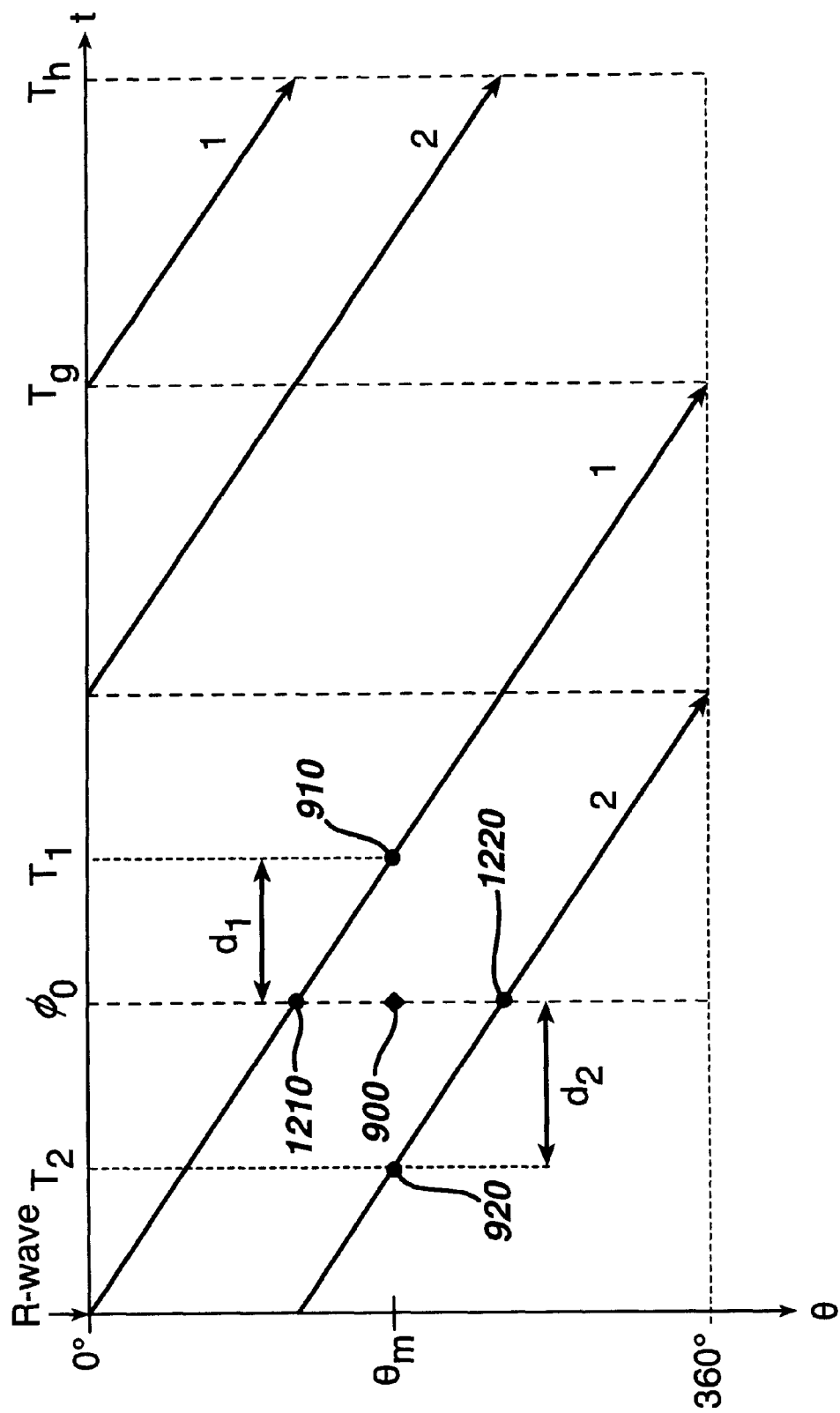

FIGS. 12–13 illustrate the data relationships that may be utilized in a particular embodiment of the invention. In FIG. 12, the initial trajectories 1 and 2 respectively include projection views 1210 and 1220 at the desired phase $\phi_0$ and corresponding view angles. The point 900 again represents a missing projection view for the heart phase $\phi_0$, because neither of the available trajectories includes a projection view at the view angle $\theta_m$. Two nearest neighbor projection views 910 and 920 may be identified from the trajectories 1 and 2, respectively, using the time stamp correlations.

FIG. 13 shows phase differences $d_1$ and $d_2$ (represented as timing differences) respectively associated with the projection views 910 and 920. Using such timing differences, the data values of 910 and 920 may be combined through a predetermined interpolation process (operation 1040 of FIG. 10) such as a weighted linear interpolation process. A data value for view 900 may be determined in such a process from corresponding data values for the views 910 and 920 using an interpolation formula such as $$P = \frac{1}{\Delta T} [d_2 P' + d_1 P''] \qquad (1)$$

$$= \left(\frac{\phi_0 - T_2}{T_1 - T_2}\right) P' + \left(\frac{T_1 - \phi_0}{T_1 - T_2}\right) P''$$

where $\Delta T = T_1 - T_2$, $d_1 = T_1 - \phi_0$, and $d_2 = \phi_0 - T_2$. Here P' and P" are the data values of the views 910 and 920 at respective detector positions in the projection views.

In the foregoing example the differences $d_1$ and $d_2$ may be determined directly from the time stamp data of the projection views 910 and 920, if the heart rate is assumed to be constant. Such an assumption ensures that the difference in the heart configuration at $\phi_0$ and $T_1$, for example, directly corresponds to the time difference $d_1$. On the other hand, as noted above, the present invention also accommodates an irregular heart rate for which the heartbeat period $T_h$ may vary with each trajectory.

Figure 14:
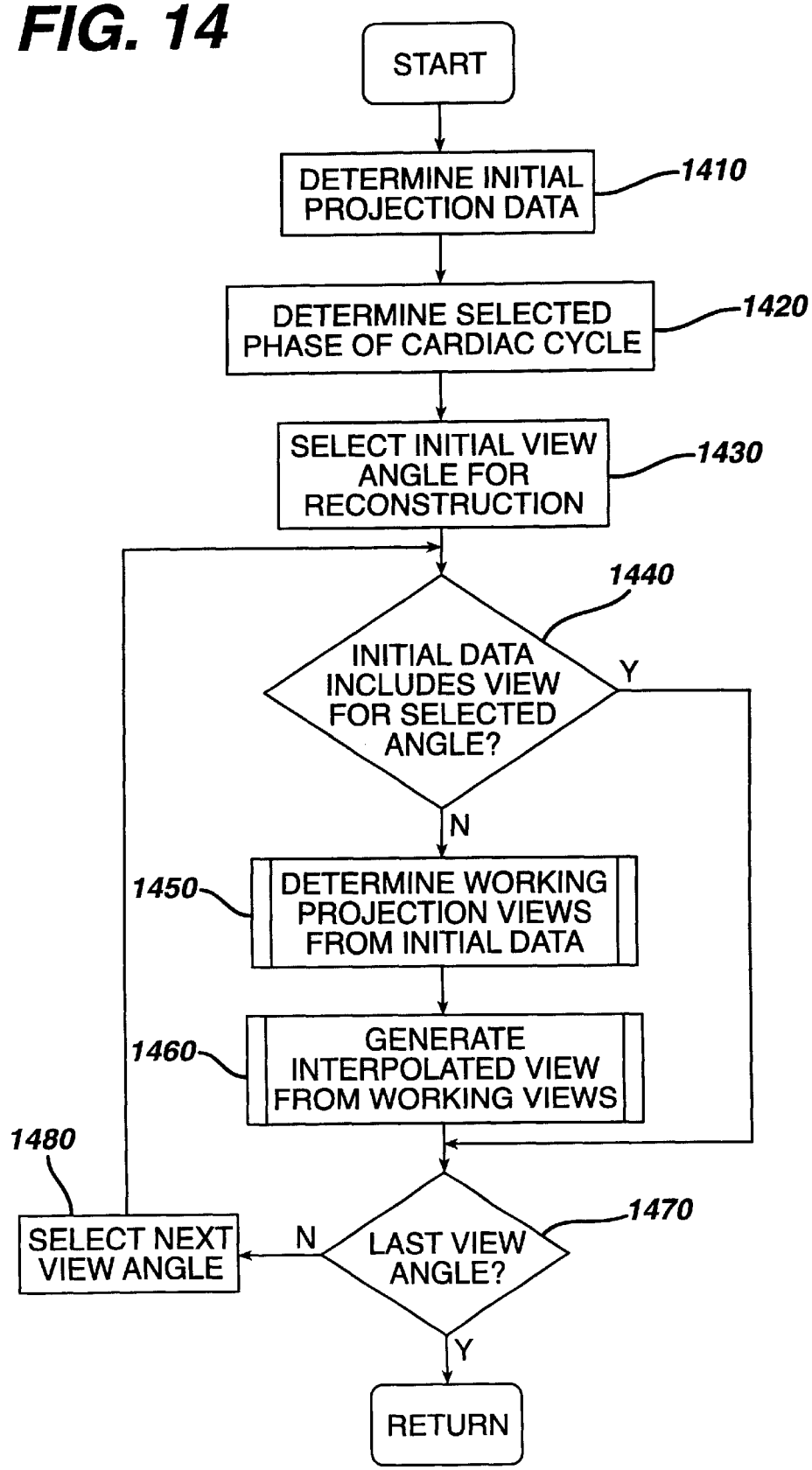
FIGS. 14–16 are flow diagrams illustrating procedures for carrying out operations as illustrated in FIGS. 12–13.

FIG. 14 shows a flow diagram illustrating the main operations of a procedure to implement the invention for generating a projection data set comprising a complete set of projection views for reconstructing a slice image. As in the operation 1010 of FIG. 8, an operation 1410 determines the initial projection data (i.e., the sinogram data for a plurality of scanning rotations). A particular phase of the cardiac cycle, such as $t = \phi_0$, is selected in an operation 1420.

An initial view angle is selected in an operation 1430. Both the initial view angle and the angular interval between projection views typically will depend on the θ discretization (the sampling frequency, such as 240 Hz) of the sinogram data. An initial testing operation 1440 may determine whether the initial projection data includes a projection view for the selected view angle and the selected phase.

If the selected view angle corresponds to a missing projection view at operation 1440, then the procedure determines working projection views at operation 1450. An interpolated projection view is generated at an operation 1460. These operations will be described in detail with reference to FIGS. 15–16. If the sinogram data includes a projection view for the selected phase and view angle, then the desired view angle is not a missing view angle. The procedure of FIG. 14 then skips operations 1450–1460 and advances to an operation 1470, where a determination is made as to whether the selected view angle is the last view angle needed for the desired reconstruction. If not, then a next view angle is selected at operation 1480, and the procedure returns to the testing operation 1440.

Figure 15:
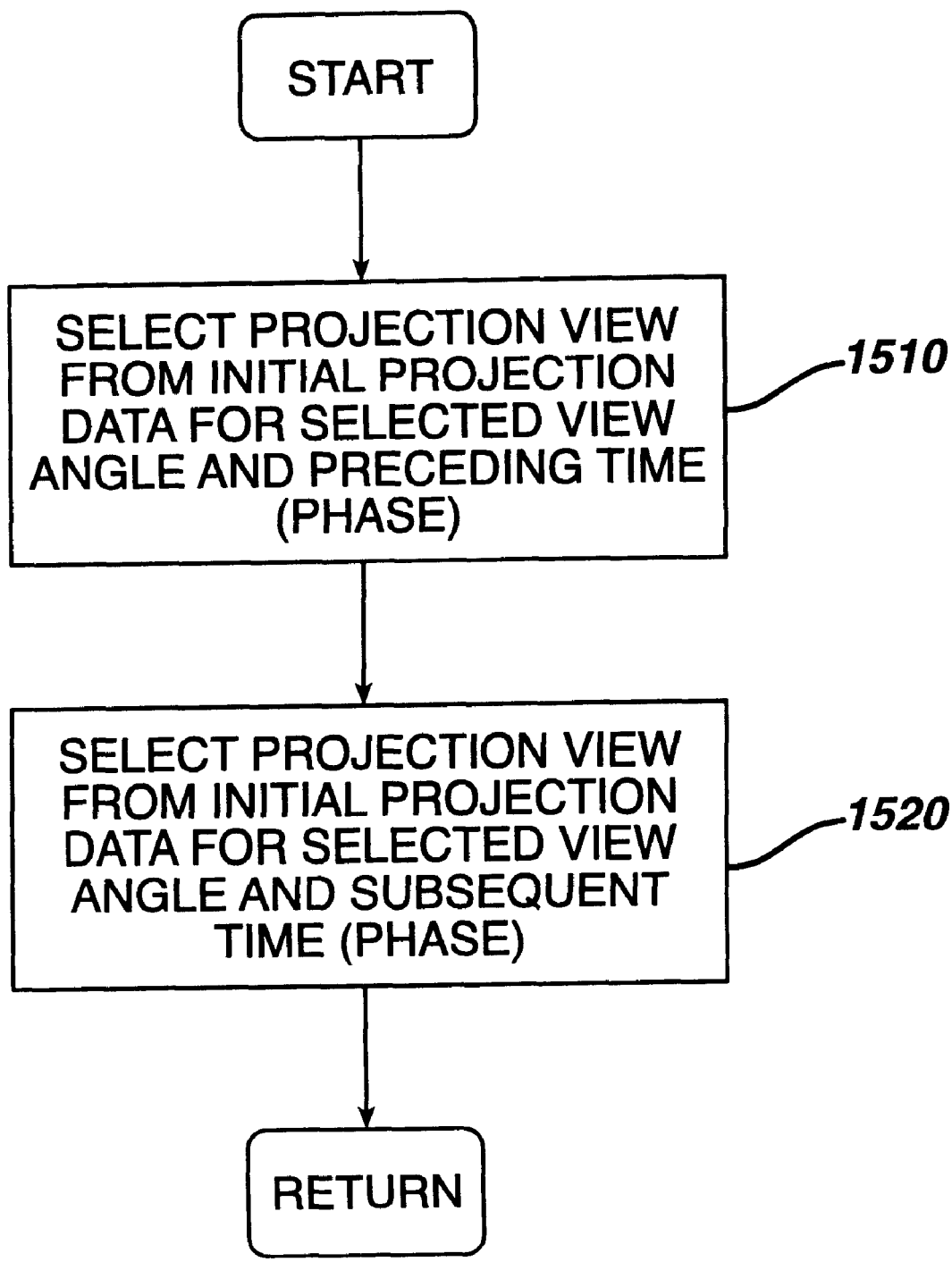

FIG. 15 shows a flow diagram illustrating a version of the determination operation 1450. In an operation 1510, a projection view for the selected view angle is selected from the initial projection data. The particular projection view may be selected based on both the selected view angle and the initial projection data corresponding to phases prior to the selected phase $\phi_0$ in the cardiac R-R cycle.

As has been noted with respect to FIGS. 12–13, the selected view angle occurs in each of the data trajectories of the initial projection data at a specific timing. A preferred embodiment of the invention in this aspect selects the projection view 920 at the selected view angle and occurring in the trajectory 2 closest in time before the timing of the desired cardiac phase $\phi_0$. The term "configuration phase" will be used to mean the phase of the physical configuration of the heart at an associated moment in each beat of the heart.

An operation 1520 produces a similar selection result, but the projection view 910 is selected from projection data subsequent to the selected phase (time). These two operations (1510 and 1520) determine two projection views that may be used as the working projection views in the remainder of the procedure illustrated in FIG. 14.

FIG. 15 illustrates a particular embodiment for selecting working projection views in pairs. It will be apparent to those of skill in the art that the present invention also encompasses other arrangements for selecting the working projection views. Indeed, a significant aspect of the present invention is the discovery that substantive relationships can exist between disparate initial projection views. Such relationships can provide additional information for improving the quality of reconstructed images. Thus, as will be seen, the present invention encompasses a variety of different approaches for identifying initial projection views between which such substantive relationships exist. Various embodiments of the invention are possible for combining the initial projection views to utilize the additional information that may be provided by relationships.

Figure 16:
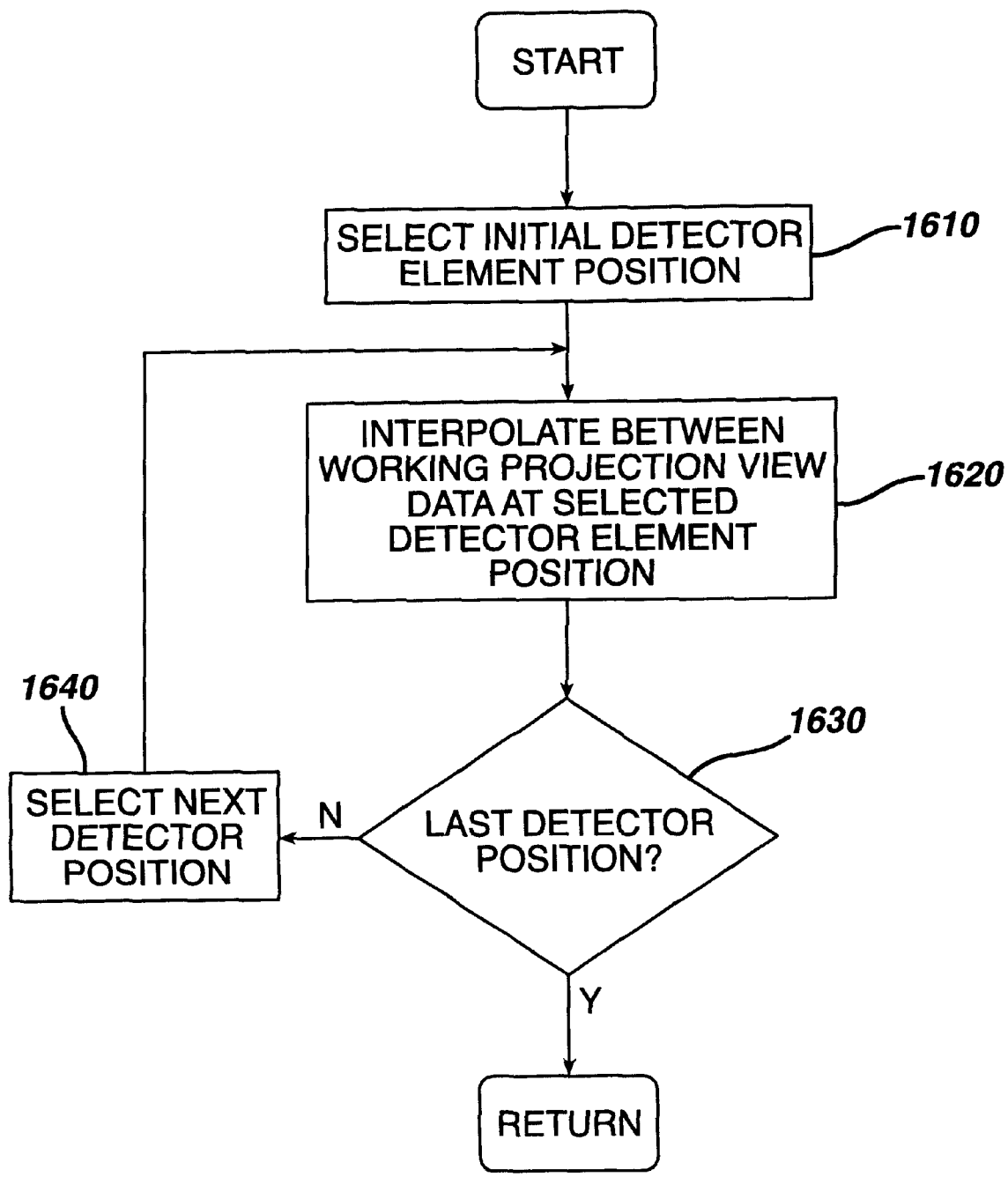

FIG. 16 is a flow diagram illustrating a particular embodiment of the interpolation operation 1460 of FIG. 14. As FIGS. 4–5 indicate, each projection view may comprise, for example, 888 data values each corresponding to an output of a detector element of the detector array (such as array 216 or 316). An operation 1610 selects respective initial data elements from the working projection views. This selection may be based on the position of the detector element from which the data elements are generated. Alternatively, any other commensurate numbering system for identifying the respective data elements in the sinogram rows may be used.

An operation 1620 performs a computational procedure to interpolate between the selected data element values of the working projection views. Any of various interpolation procedures may be used, as discussed below. The result is an interpolated data value corresponding to the selected data element position, the selected phase, and the selected view angle. An operation 1630 determines whether further sets of data elements remain to be interpolated between the working projection views. If so, then the next data element values are selected at an operation 1640 (such as by selecting a next detector element position). The procedure of FIG. 16 then returns to the operation 1620 for another iteration of the interpolation computation.

The approach of the present invention makes the resulting projection data (any initial projection data for the desired phase, in combination with interpolated projection data) more consistent, particularly at view angles near angles at which the sector approach would join different sectors. The results provided by the invention are further improved by the fact that the general profile of motion during the cardiac cycle is known as a function of time. This profile can be used to compute weights to be used in the interpolation operation 1460. In particular, it has been found that careful selection of the interpolation weights based on the motion profile can result in even better image quality.

In a particular implementation of the invention, the weights may be selected to minimize image distortion arising from motion of the heart at the working projection views. In this approach the interpolation method weights the data from a particular working projection view (and trajectory) based on the amount of heart motion at the phase of the cardiac cycle to which the working projection view corresponds. The weighting applied to the other trajectory (or trajectories) used in the interpolation may be changed similarly, based on the relative heart position (or configuration) at the respective phases.

The relative heart position at a given projection view may be determined through off-line analysis of the contemporaneous EKG data. The amounts of heart motion at different configuration phases are well known to those of skill in the art of cardiac physiology and may be correlated to the projection views P' and P" through the EKG data.

Alternatively, any of various other interpolation methods may be used. In another particular implementation, a weighted inverse quadratic interpolation is performed. Here each weight may be computed to be proportional to the square of the time difference between the interpolated time and the time of the weighted projection data value. For example, a data value for the projection view 900 may be computed according to the formula $$P = \frac{1}{d_1^2 + d_2^2} [d_2^2 P' + d_1^2 P''] \quad (2)$$

$$P = \frac{(\phi_0 - T_2)^2}{d_1^2 + d_2^2} P' + \frac{(T_1 - \phi_0)^2}{d_1^2 + d_2^2} P''$$

$$P = \frac{(\phi_0 - T_2)^2}{(T_1 - \phi_0)^2 + (\phi_0 - T_2)^2} P' + \frac{(T_1 - \phi_0)^2}{(T_1 - \phi_0)^2 + (\phi_0 - T_2)^2} P''$$

It is noted that the equations (1) and (2) illustrate this feature of the present embodiment in the simple case where $|T_1-\phi_0|$ and $|\phi_0-T_2|$ are less than $T_h/2$. In many cases this condition may be satisfied automatically by using existing projection views 910 and 920 from consecutive gantry rotations (consecutive data acquisition cycles). However, the present aspect of the invention also applies in many other contexts where one or more of these simplifying assumptions fails to hold. The principles of the present aspect of the invention may also be applied where a direct phase difference (such as $T_1-\phi_0$) actually is greater than $T^h/2$. Such a case may be addressed as described with reference to equation (5) below.

Among its numerous advantages, the present invention enables the times at which to collect the projection data (for reconstructing an image of the heart at a particular configuration phase) to be determined prospectively. A method of the present invention therefore does not require the X-ray tube to be on all the time. Instead, a method of the invention operates with data collected at or near a particular phase of the heart. The time correlation by which such a method is employed can be achieved by prospective gating.

Usually in medical imaging procedures the heart rate is not uniform during the data acquisition process. As in the discussion above with respect to FIG. 10, the preferred procedure here is to collect an electrocardiographic data set along with the projection data. The EKG data set can then be correlated off-line with CT scan data, using the time stamps as noted previously. Thereafter, using the time stamps and the correlations to the EKG data, the particular projection data corresponding to a selected cardiac configuration phase can be identified.

Such an adaptation to heart rate variations is well known in the art and has been used, for example, in the sector approach described above with respect to FIG. 7. Persons skilled in the art will readily appreciate the appropriate measures to be used with the present invention to compensate for the presence of heart rate variability. For example, a compensation model is employed in the technique of U.S. Pat. No. 5,997,883 to Epstein et al. noted previously.

On the other hand, a further embodiment of the present invention is particularly useful in cases where heart rate variability exists. The basic approach described above is employed again, but variations in the heart rate are accommodated in the interpolation process.

Figure 17:
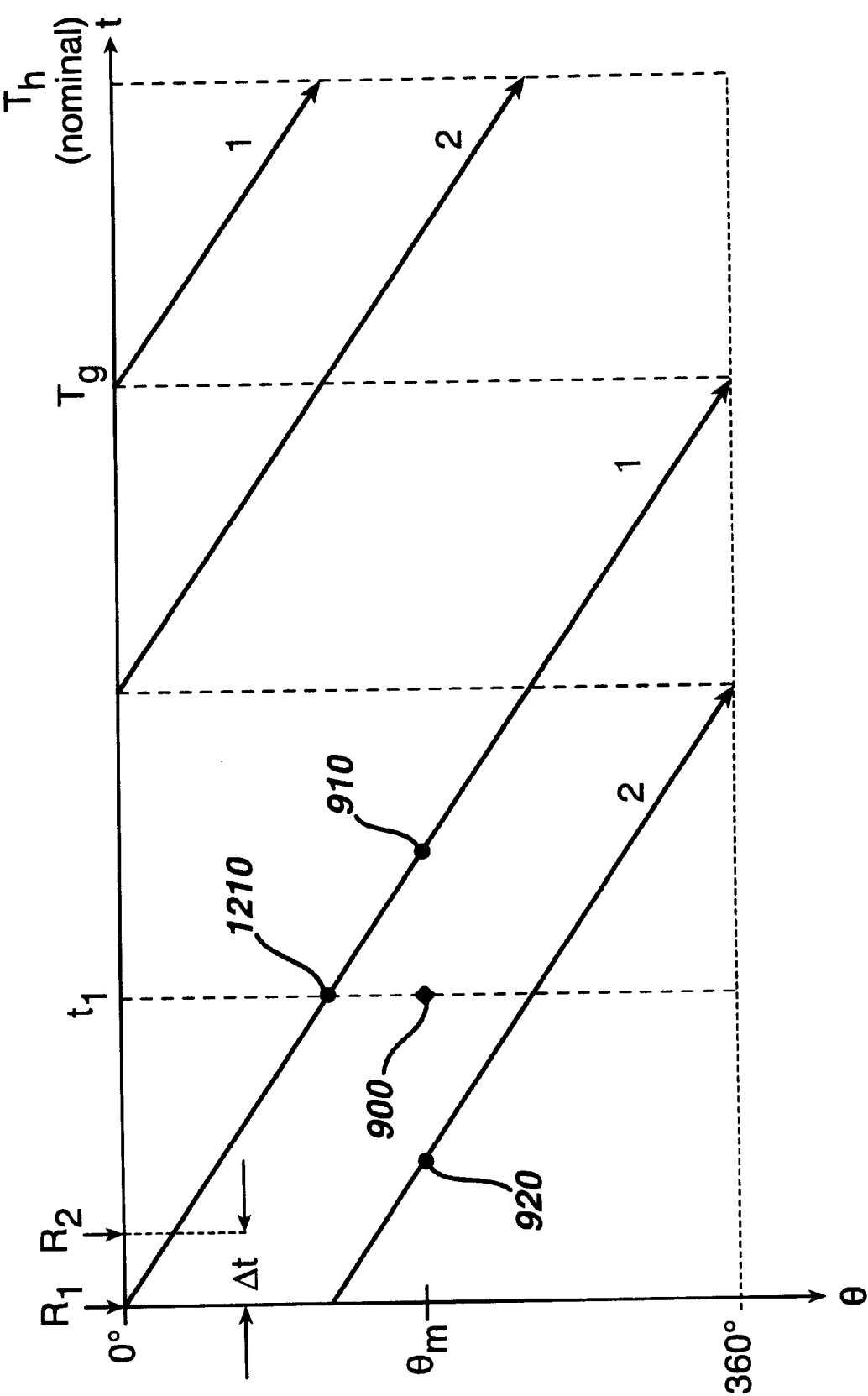
FIGS. 17–19 are diagrams illustrating an application of the present invention in a case of irregular heartbeat.

FIG. 17 illustrates a typical effect on a trajectory when the heart rate varies. Trajectories 1 and 2 again represent successive portions of CT projection data. The scanning rotation also continues to have a fixed period $T_g$. However, unlike in FIGS. 12–13, the heart rate is now variable with a period varying around some nominal period $T_h$. The rightmost extent of the graph in FIG. 17 does not represent successive completions of the R-R cycle of the heart. However, like FIGS. 12–13, the trajectories in FIG. 17 wrap around to t=0 when they reach $t=T_h$.

Unlike FIG. 12, for example, in FIG. 17 the R-waves of different heart cycles occur at different time positions on the graph. An R-wave $R_1$ that begins the R-R cycle of trajectory 1 is illustrated as occurring at temporal position t=0 on the graph. However, an R-wave $R_2$ occurs at a later temporal position t=Δt. The R-wave peak at $R_2$ occurs at a time $T_h+\Delta t$ following $R_1$, while the temporal positions on the graph reflect the fact that the graph wraps around to t=0 at intervals of $T_h$. The time difference Δt can thus be viewed as a phase delay between the cycle beginning with $R_1$ and the cycle beginning with $R_2$.

Figure 18:
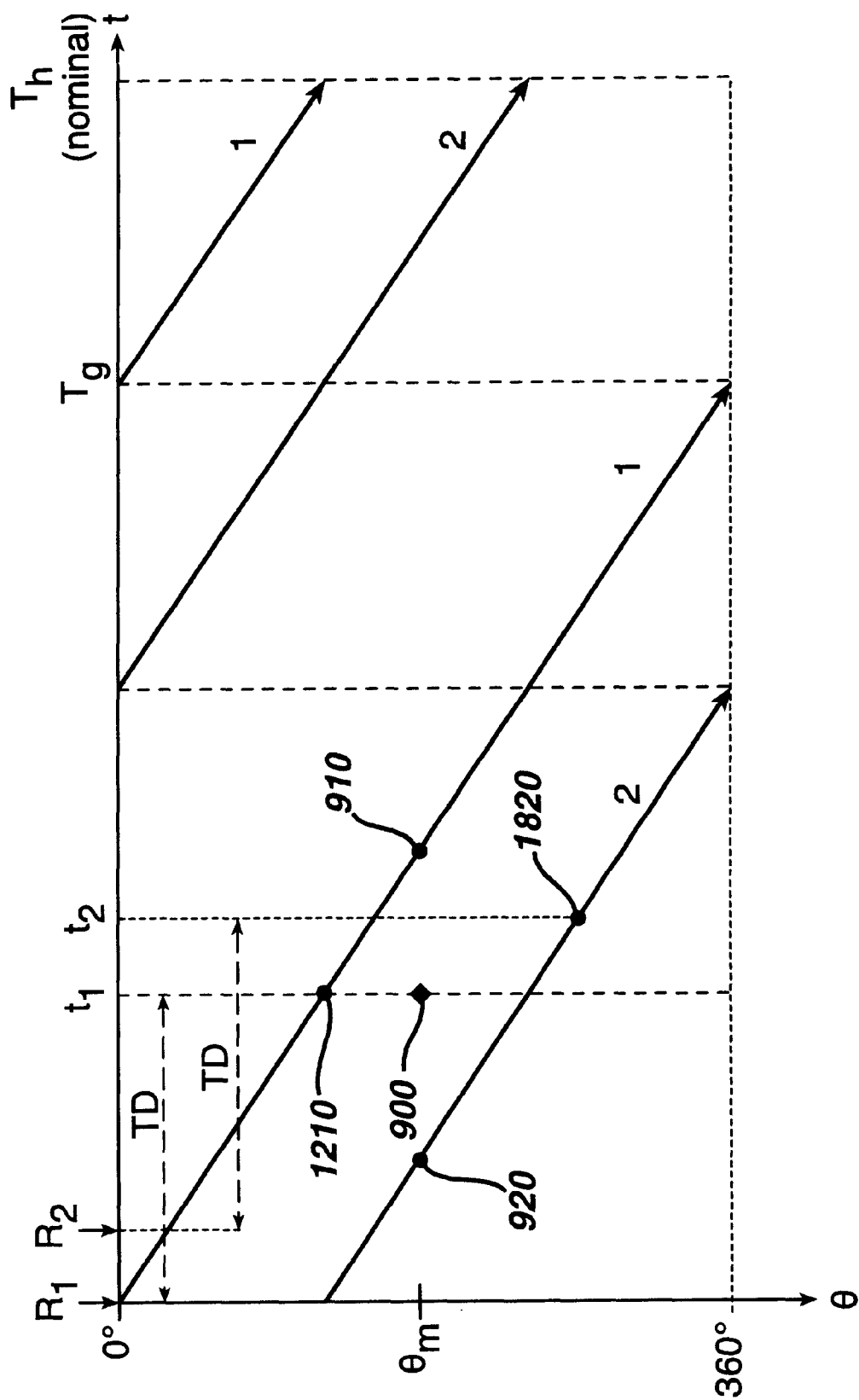

FIG. 18 illustrates the effect of heart rate variability on the time correlations between the CT projection data and the configuration phases of the heart as indicated by contemporaneously collected EKG data. Trajectories 1 and 2 with respective R-waves $R_2$ and $R_1$ are shown as in FIG. 17. Again, a set of projection views is desired for reconstructing a useful image of the heart at a specified configuration phase. In the cardiac cycle of trajectory 1, the specified configuration phase is assumed to occur at temporal position $t_1$. The trajectory 1 again includes the projection view 910 having a time stamp correlated to the temporal position $t_1$. A fixed time delay TD is defined to be numerically equal to the temporal position $t_1$.

The fixed time delay TD will serve a function similar to the fixed heart cycle ratio mentioned above (represented by $\phi_0$ in FIG. 12), but for the ease of varying heart rate. In each successive heart cycle, the timing of the specified configuration phase will occur at the time delay TD after the R-wave of the cycle. FIG. 18 shows that the specified phase therefore occurs in trajectory 2 at a temporal position $t_2$ on the graph.

The trajectory 2 includes a projection view 1820 that is time stamped to correspond to the temporal position $t_2$. The temporal position $t_2$ of view 1820 is commensurately offset (by the phase delay Δt) from the time position $t_2$ corresponding to the projection view 910 from trajectory 1. The view 1820 nevertheless represents the heart at the specified phase, because the cycle of trajectory 2 begins at the R-wave $R_2$. An image reconstruction of the heart in that specified configuration will therefore utilize both the projection view 910 and the projection view 1820.

The embodiment of the invention described with reference to FIGS. 12–13 can provide data for such a missing projection view through gated reconstruction that bins the data into phases. If the heart rate is uniform, as illustrated in FIG. 12, then these phases occur at regular intervals $T_{heart}$ in time. The horizontal axis in FIG. 12 consistently represents both time t and cardiac phase $\Phi_{ij}$. This correspondence allows differences in the phases of the heart at the projection views 900, 910, and 920 to be determined directly from the temporal positions of those views on the graph.

However, heart rate irregularity is particularly common among patients undergoing cardiac care, and this creates a problem for using EKG data for gated reconstruction. As in FIGS. 12–13, this embodiment of the invention provides an additional, synthesized projection view 900 to be combined with the views 910 and 1820 in reconstructing the image.

But when the cardiac cycle is irregular, the direct correspondence between temporal position and cardiac phase is destroyed.

FIG. 18 illustrates that the temporal position $t_2$ of the projection view 1820 is delayed relative to the temporal position of 910. This delay is induced by, and is numerically equal to, the phase delay $\Delta t$: $t_2-t_1=\Delta t$. It follows that when the heart rate is irregular, a given configuration phase will not occur at a regularly repeating temporal position, such as at $\phi_0$. Instead, the desired phase will occur in each cardiac cycle at a time position determined by the R-wave of the cycle and the fixed time delay TD.

Figure 19:
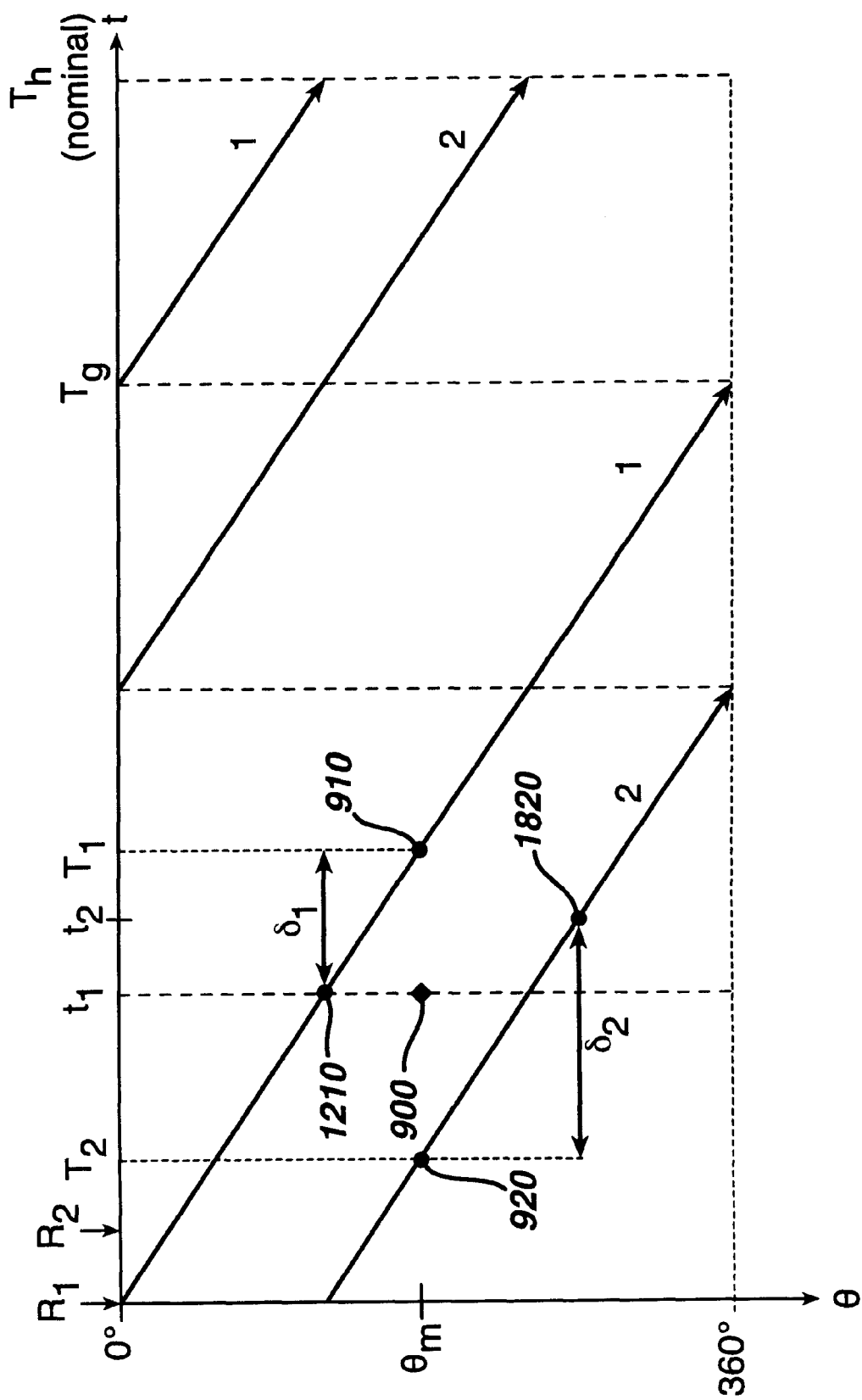

FIG. 19 illustrates an approach to account for the phase delay $\Delta t$ in the determination of the differences between the cardiac phases. This approach enables the present invention to provide consistent projection view interpolation, in the presence of heart rate irregularity. The basic approach is the same as illustrated in FIG. 13: combine the working projection views 910 and 920 by interpolation to generate an interpolated projection view 900. Moreover, as in the case of constant heart rate, the interpolation formula will generally blend corresponding data values from initial projection views 910 and 920 based on differences between the different phases.

The timing differences $\delta_1$ and $\delta_2$ in FIG. 19 correspond to $d_1$ and $d_2$ as in FIG. 13 and are again associated with the projection views 910 and 920. However, because the desired phase occurs in trajectory 2 at temporal position $t_2$, $d_2$ includes the difference between $t_1$ and $t_2$, i.e., $t_2-t_1=\Delta t$. Thus, for an irregular heart rate, the interpolation formula desirably blends the initial projection views 910 and 920 based on $$\delta_1=T_1-t_1,$$

$$\delta_2=t_2-T_2=t_1-T_2+(t_2-t_1)=t_1-T_2+\Delta t. \quad (3)$$

Any of the various interpolation methods known in the art may be used for interpolation between 910 and 920 in FIG. 19, using appropriate measures of phase differences such as $\delta_1$ and $\delta_2$. For example, either of the formulas (1) and (2) above may be used directly by substituting $\delta_1$ and $\delta_2$ for $d_1$ and $d_2$, respectively. The use of a fixed delay TD ensures that the working projection views will correspond to a same phase of the cardiac cycle following the trigger phase. The procedure illustrated in FIGS. 14–16 may then be employed to generate the interpolated projection view 900.

The same delay time TD can be used to generate projection views for image reconstruction at a succession of slice positions $z_0$. A number of slice images can be generated to provide a reconstructed three dimensional image of the heart at the configuration phase specified by the selected delay TD. It is desirable to use a delay time TD corresponding to a cardiac phase at which the heart is nearly still. Alternatively, the approach of the invention may be further extended by performing the aforementioned three dimensional image reconstruction for each of a series of delay times TD. This alternative allows the creation of a time succession of such three dimensional images to provide a dynamic (four-dimensional) model of the heart.

The aspect of the present invention described with reference to FIG. 10 may be implemented in various different embodiments, several of which may have particular application in dynamic imaging contexts such as cardiac imaging. An embodiment suitable for a given imaging context may be selected according to the particular imaging system hardware to be used, characteristics of the object to be imaged, image parameters to be emphasized, and so forth. Two particular embodiments of the invention will now be described in more detail. Those of skill in the art will appreciate details and desirable features of other alternative embodiments, upon considering the foregoing general description together with the particular descriptions to be presented below.

Interpolation Between Several Projection Views

Figure 20:
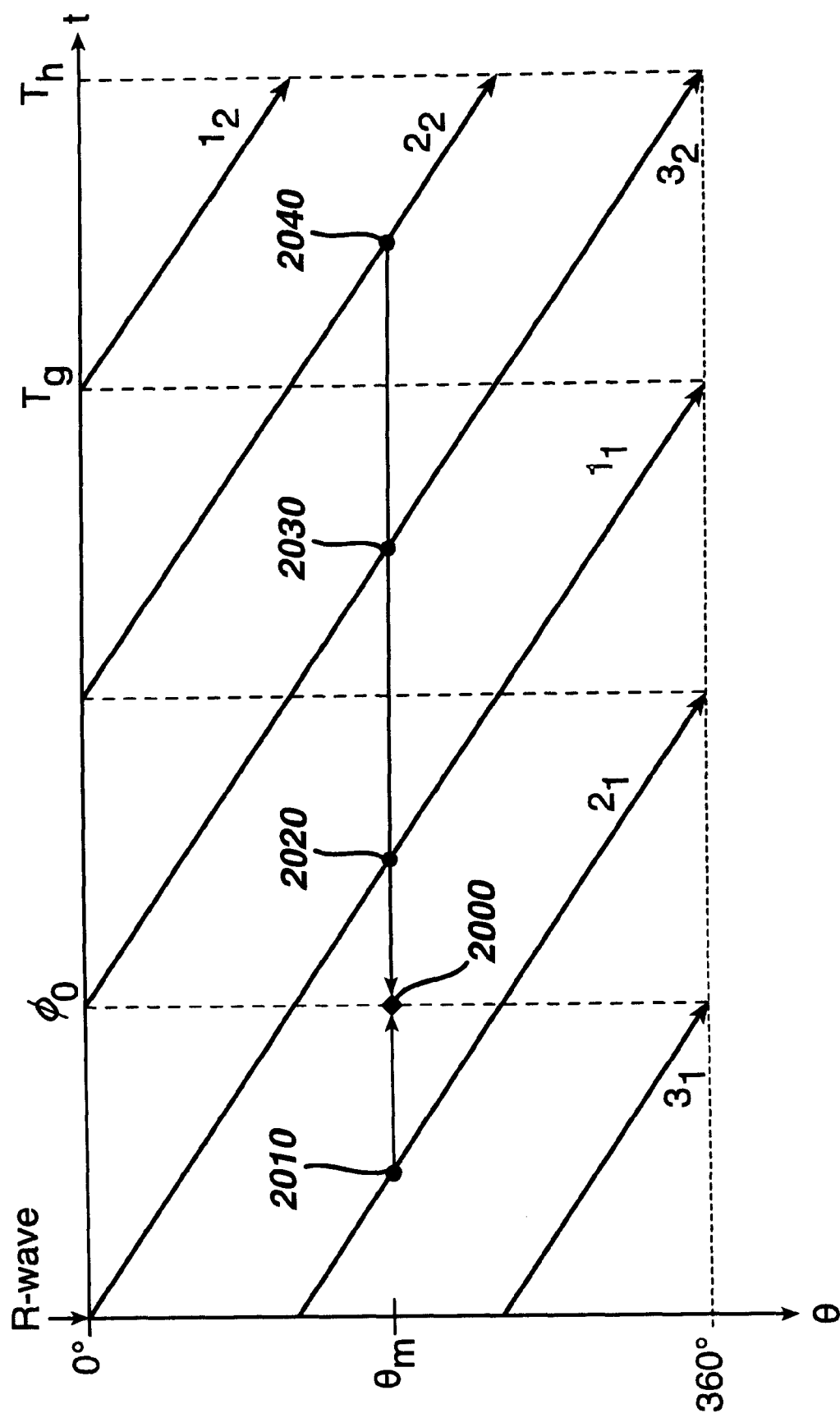
FIG. 20 is a trajectory diagram illustrating another embodiment of the invention for phase interpolation between several projection views.

FIG. 20 is a trajectory graph, similar to the graphs of FIGS. 12–13, but illustrating an alternative aspect of the invention. The embodiment illustrated in FIGS. 12–13 provided phase interpolation between two projection views selected from consecutive different data acquisition cycles, and thus falling on neighboring trajectories in the graphs. Here, for added clarity of illustration, the trajectories are labeled to indicate both their respective gantry rotations and heart cycles. Thus the label "$M_N$" indicates the trajectory represents a sequence of projection views from the M-th heart cycle and the N-th gantry rotation.

The alternative embodiment of FIG. 20 provides for generating an interpolated projection view 2000 by phase interpolation between several working projection views 2010, 2020, 2030, and 2040. While four working projection views 2010–2040 are shown, it will be apparent that this aspect of the invention encompasses other numbers of projection views, both more than four and less than four. Moreover, it may be seen that assignment of zero interpolation weights may effectively exclude some working projection views from the phase interpolation of a particular embodiment. For example, assignment of zero weights to the projection views 2030 and 2040 effectively reduces this alternate aspect of the invention to the previous aspect, in which phase interpolation is applied to two neighboring projection views.

More generally, this alternative aspect may be embodied through phase interpolation between several (e.g., three or more) working projection views. The result is again to obtain an interpolated projection view, now based on the interpolation formula $$P_\phi(\theta) = \sum_{i,j} w_{ij}(\theta, \phi) \cdot P_{ij}(\theta) \quad (4)$$

Here i indexes cardiac cycle and j indexes gantry rotation (i.e., data acquisition cycle). The equation (4) applies fully to the case of axial scanning but is not limited to such contexts, as will be seen below.

The weights $w_{ij}(\theta, \phi)$ in equation (4), some of which may be zero, may be selected based on any of various suitable weighting schemes. For example, the weighting formulas $$w_{ij}(\theta, \phi) = \frac{w'_{ij}(\theta, \phi)}{\sum w'_{ij}(\theta, \phi)}, \quad \text{where} \quad (5)$$

$$w'_{ij}(\theta, \phi) = [\Delta(\Phi_{ij}(\theta) - \phi)]^{-p} \quad \text{and}$$

$$\Delta(\Phi_{ij}(\theta) - \phi) \equiv \begin{cases} |\Phi_{ij}(\theta) - \phi|, & |\Phi_{ij}(\theta) - \phi| \le \frac{T_h}{2} \\ T_h - |\Phi_{ij}(\theta) - \phi|, & \frac{T_h}{2} < |\Phi_{ij}(\theta) - \phi| \le T_h \end{cases}$$

define weights $w_{ij}(\theta, \phi)$ similar to the coefficients of P' and P'' in (1) and (2) above.

The case where the exponent is p=2, for example, achieves rapid decay with increasing phase distance of the working projection view from the desired phase. A rapid decay condition reduces the influence of more distant working projection views, relative to the contribution to the interpolation result from views close to the desired phase.

It is noted that the above definition of $\Delta(\Phi_{ij}(\theta)-\phi)$ accounts for the case when the distance $|\Phi_{ij}(\theta)-\phi|$ is greater than $T_h/2$, one-half the heart cycle period. Such a difference function may be applied (with changes that will be apparent to those of skill in the art) in equations (1) and (2) above, in any case where the difference $\phi_0-T_2$ or the difference $T_1-\phi_0$ exceeds one-half of the heart cycle period $T_h$.

Those of skill in the art will appreciate that the inverse-polynomial weighting $[\cdot]^{-P}$ set forth above is only one example of a weighting function that may be applied for phase interpolation as provided by the present invention. For example, the weights $w_{ij}(\theta, \phi)$ may be defined in terms of any nonnegative monotonically decreasing function of the distance $\Delta(\Phi_{ij}(\theta)-\phi)$ such that the sum of the weights for a given $\theta$ and $\phi$ is unity: $\Sigma w_{ij}(\theta, \phi)=1$. For example, the weighting function $w_{ij}(\theta, \phi)$ may be reduced to a unit step function having value 1 at the nearest-neighbor phase $\Phi_{ij}(\theta, \phi)$ and value 0 at more distant phases. The result of this weighting choice in equation (4) would be to reduce the interpolation approach of the present invention to the nearest-neighbor substitution approach described above.

Another implementation provided by the present invention assigns non-zero weights to working projection views in pairs, with each pair comprising one view before and one view after the desired phase (i.e., the phases of each pair "sandwich" the desired phase). In such an alternative implementation it may be particularly desirable to use sandwiching with working projection views from consecutive trajectories. That is, for each of the sandwich pairs, the projection views of the pair may be chosen from consecutive data acquisition cycles to sandwich the desired phase therebetween.

Helical Scanning

In an implementation for cardiac imaging, as described above, the invention enables reconstruction of a single slice through the heart with high resolution in time. If reconstruction is desired for more than one slice, such as for a volumetric section (for example, a volumetric image of the entire heart), then further processing is performed.

One way to achieve this further goal is to perform the previously described method for each of several slices through the heart. However, collection of the scan data to be used for each slice involves multiple rotations of the gantry. For the example illustrated in FIG. 8, three complete scanning rotations would be needed for each slice.

Such an operation of multiple rotations for multiple slices would require an undesirably long data collection time. In particular, collection of data for all the slices through the heart would be difficult to achieve in one breath hold (20–60 seconds), at least with the current CT technology. Such an approach would also deliver to the patient an undesirably large X-ray dose. Thus, at least for dynamic contexts such as cardiac imaging, the axial scanning arrangements illustrated in FIGS. 2–3 may have disadvantages.

Figure 21:
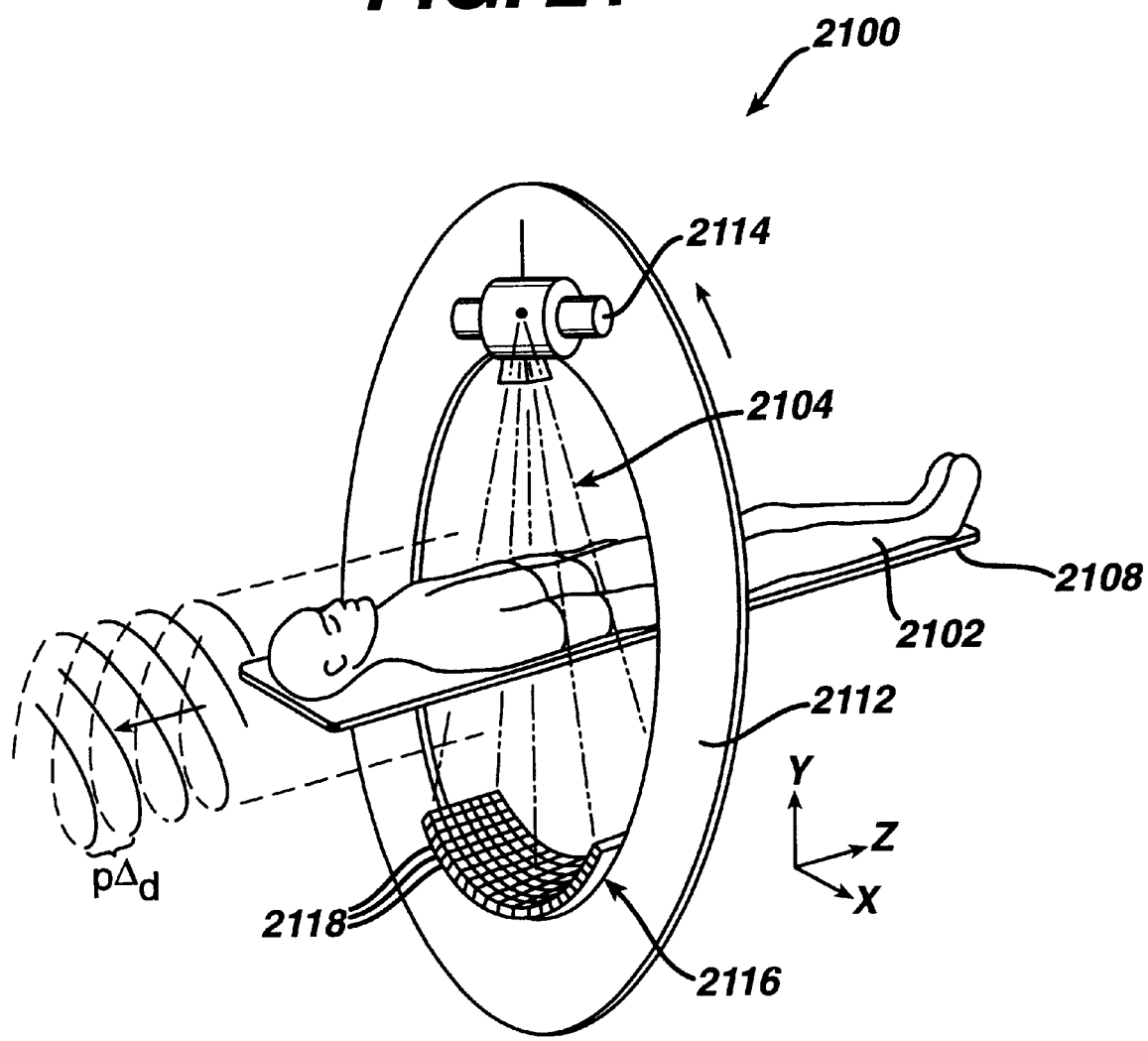
FIG. 21 is a diagram of a source-detector assembly for a helical x-ray CT scanning system using a multi-row detector array.

FIG. 21 illustrates a source-detector assembly 2100 for a desirable alternative to axial scanning, called helical scanning. The principal features of assembly 2100 are analogous to the components of assemblies 200 and 300 in FIGS. 2 and 3, respectively. A subject 2102 (here illustrated as a human patient) is illuminated by an x-ray beam 2104 while disposed on a (possibly movable) table 2108. A gantry 2112 supports an x-ray source 2114 that generates the imaging x-ray beam 2104. However, unlike the fan beams 204 and 304 described previously, beam 2104 is a so-called cone beam that spreads (or "fans") in two generally orthogonal directions as the beam is projected away from the source 2114.

The particular assembly 2100 of FIG. 21 corresponds to the third generation axial assembly 200 of FIG. 2. Specifically, the gantry 2112 also supports a detector array 2116 comprising multiple detector elements 2118, and both the source 2114 and the detector array 2116 are transported around the subject 2102 along respective circular paths as the gantry 2112 rotates. The detector array 2116 and the source 2114 are both fixed to the gantry 2112. The detector 2116 thereby remains opposite the source 2114, relative to the subject 2102, during the rotation.

Unlike detector array 216, however, the array 2116 is a so-called multi-row detector comprising several rows of detector elements. The array 2116 thereby provides a two dimensional detection area, which corresponds to the spread of the cone beam 2104 in two directions. Accordingly, at each (lateral) detector position of a single row detector array (such as array 216 in FIG. 2), the array 2116 comprises an entire set of detector elements arranged in a column generally parallel to the axial direction z.

Figure 22:
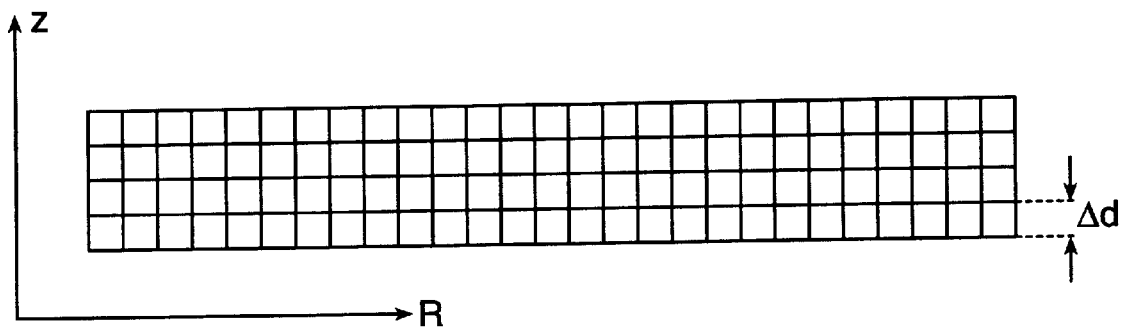
FIG. 22 is a schematic diagram of a multi-row detector array.

FIG. 22 shows a schematic diagram of the detector elements of a multi-row detector such as detector array 2116. In the illustrated example, each column of the array 2116 comprises four detector rows. Each detector has a thickness of $\Delta_d$.

Helical scanning relaxes the requirement of axial scanning systems that the axial position of the gantry is fixed at a single point throughout the data collection cycle. Instead, the entire gantry (source and detector array) translates axially (in the z direction) relative to the patient. This mode of operation allows a single scan to cover the entire organ or structure under study. Thus, the motion of the gantry, as well as the individual detector elements, traces a helix. The extent of translation in the z direction (as a fraction of detector thickness $\Delta_d$) per gantry rotation is called "pitch" and is denoted by "p" in FIG. 21. Thus, the axial position of the k-th detector row can be written as $$z_k(t) = p\Delta_d \frac{\omega t}{2\pi} + k\Delta_d.$$

A helical/cone beam CT scanning system provides advantages for performing a volumetric reconstruction of the heart. For example, a multi-row detector such as detector array 2116 can collect several times more x-ray data from each scanning rotation. The axial position of the cone beam 2104 also advances continuously during the scanning operation, so that each detector element 2118 traces a helical path around the subject 2102. In this manner, the data collection proceeds continuously as the cone beam 2104 advances axially, rather than being repeatedly interrupted for a next translation maneuver.

Figure 23:
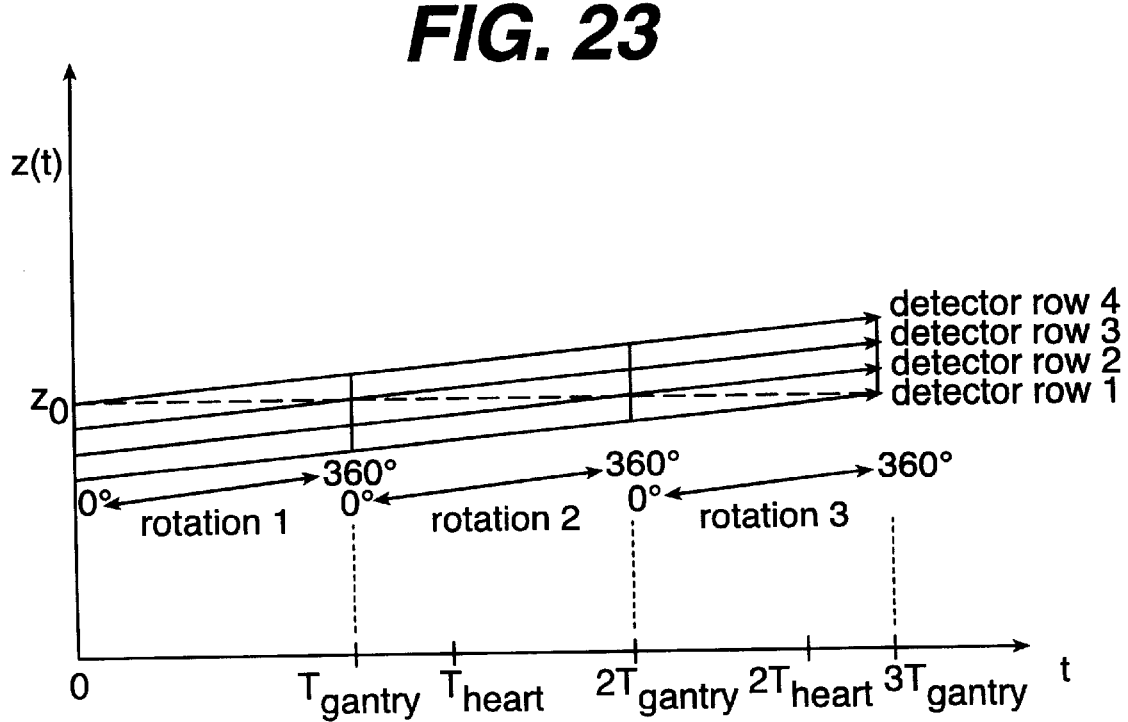
FIG. 23 is a time evolution diagram of detector row positions of a multi-row detector in helical scanning.

FIG. 23 illustrates a complication that arises with helical scanning. The rotations 1, 2, and 3 represent successive loops of the helical advance of a four-row detector array such as array 2116 shown in FIGS. 21–22. As time t evolves, each scanning rotation progresses from a 0° view angle to a 360° view angle. Further, the angle 360° for a given rotation coincides with the view angle 0° of the succeeding rotation.

However, the helical advance of the gantry during the scanning process causes the detector elements of the multi-row detector to be displaced axially during each rotation. The locations of the detector rows of a three-row detector in the z direction are shown in FIG. 23 in the z-t domain. The axial position of each detector row therefore changes, both between rotations and within each rotation. Still, each of the detector rows in the multi-row detector defines data corresponding to a proper projection view, i.e., a projection view representing attenuation data for a single axial position.

The axial displacement of the detector positions in helical scanning entails additional processing (rebinning) of the collected projection data to assemble projection views conformable to the standard image reconstruction methods. One approach is initially to reformat the helically skewed data from the multi-row detector into a sequence of sinograms each corresponding to a single axial position z. This rebinning procedure typically entails an interpolation procedure between detector element values of neighboring detector rows. An additional, phase interpolation procedure of the present invention is also performed to obtain projection data for the missing projection views at each axial position.

Figure 24:
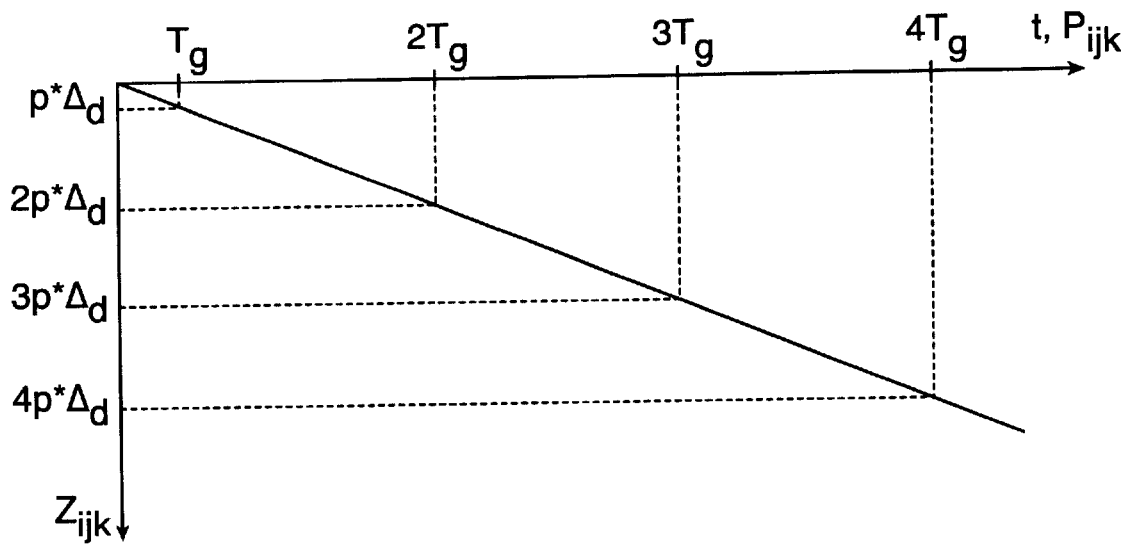
FIG. 24 is a graph illustrating tagging for rows of a multiple-row detector array.

FIG. 24 illustrates an alternative approach in which each data row of the three-dimensional helical projection data is tagged with corresponding phase information. Thus, following FIG. 11, the phase of the projection at view angle θ, cardiac cycle i, gantry rotation j, and detector row k is represented as $\phi_{ijk}$. The projection data may also be tagged with Z-axis position information $Z_{ijk}(\theta)$ based on the geometry of the detector rows, the relative speed of gantry and patient, and the gantry rotation rate. In FIG. 24 the diagonal line represents the common trajectory followed by each detector row in z as time evolves. The values $np^*\Delta_d$ on the vertical axis represent the accumulated number of data rows obtained after the corresponding number of gantry rotation periods ($T_g$, $2T_g$, $3T_g$, etc.). The slope of the diagonal line is determined by the table speed.

Figure 25:
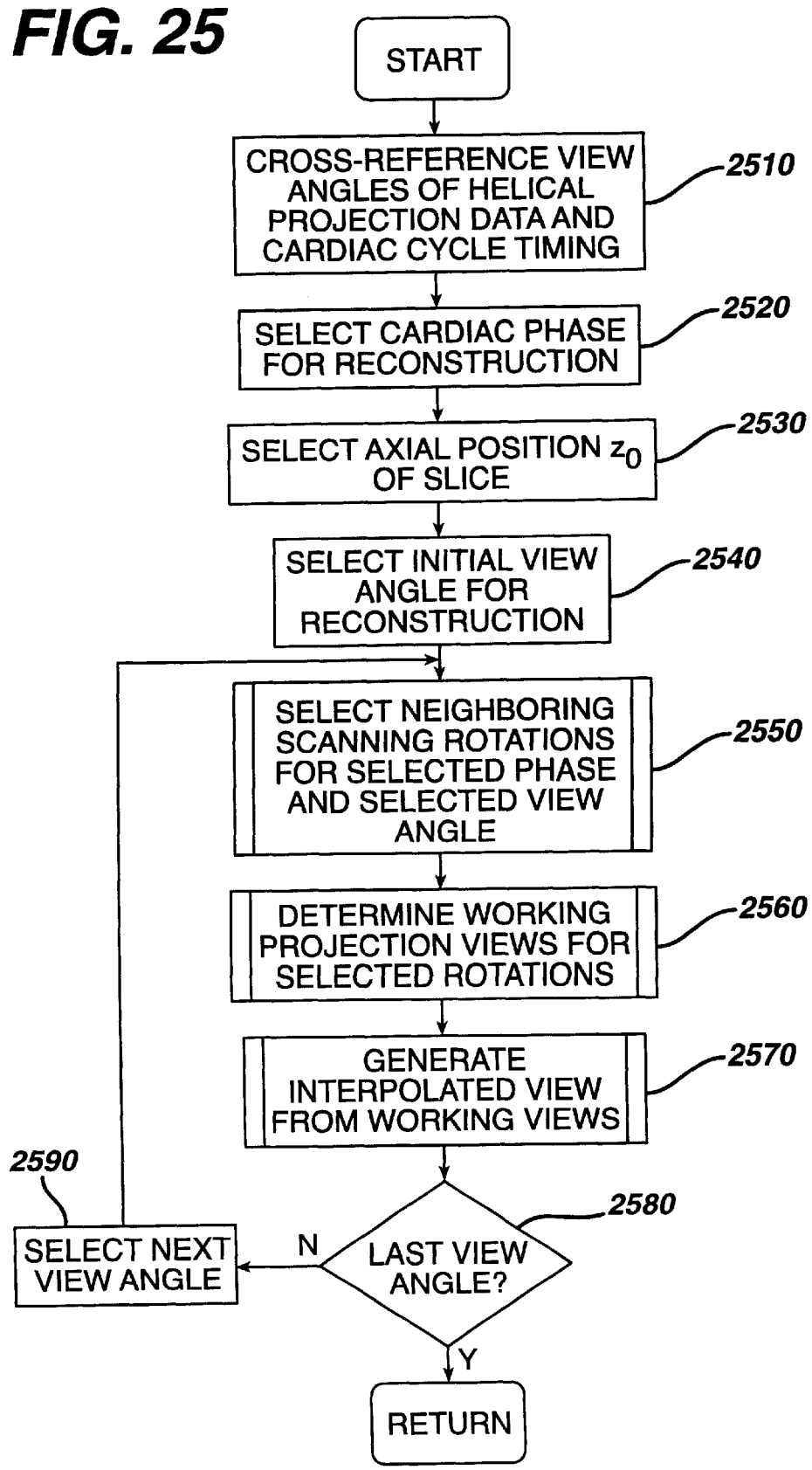
FIG. 25 is a flow diagram illustrating a procedure of an embodiment of the present invention as applied in multi-row helical scanning for cardiac imaging.

FIG. 25 shows a flow diagram illustrating a procedure to implement the present invention in the context of helical scanning. An operation 2510 cross-references the view angles of the helical projection data and the timing of the cardiac cycle. This may entail tagging the set of projection data for each view angle with timing information. The operation 2510 thereby correlates the projection data sets to the cardiac cycle phases to which the respective data sets correspond. In the case of a multi-row detector, each projection data set will comprise several rows of projection data for each view angle.

A particular cardiac phase is selected for reconstruction at an operation 2520. Because the helical scanning process collects scan data over a range of axial positions, an axial position $z_0$ of the slice to be reconstructed is also selected at an operation 2530. An initial view angle is selected at an operation 2540 for processing of the helical data.

An operation 2550 selects a set of neighboring scanning rotations for the selected cardiac phase and the selected view angle. This operation is described in more detail below with reference to FIGS. 26–28. Briefly, operation 2550 relates to the fact that the helical scan data are collected as the axial position of the gantry advances through multiple rotations. A first stage toward determining working projection views is to identify from the helical projection data the scanning rotations for which the projection data are most relevant to the missing projection view.

An operation 2560 determines working projection views for the scanning rotations selected in the operation 2550. This determining operation is described in greater detail below with reference to FIGS. 29–30. Operation 2560 relates to the fact that the helical scan data from a multi-row detector is desirably conformed into projection views for the selected slice position.

When the working projection views have been determined at operation 2560, the procedure of FIG. 25 advances to an operation 2570. In this operation, an interpolated projection view is generated from the working projection views determined in the operation 2560. The operation 2570 may be the same phase interpolation (i.e., interpolation in time) described above with respect to operation 1460 of FIGS. 14 and 16. An operation 2580 determines whether the current view angle is the last view angle for which a projection view is needed for reconstruction of the selected slice. If more view angles remain, the procedure advances to an operation 2590 where the next view angle is selected. The procedure then returns to operation 2550.

Figure 26:
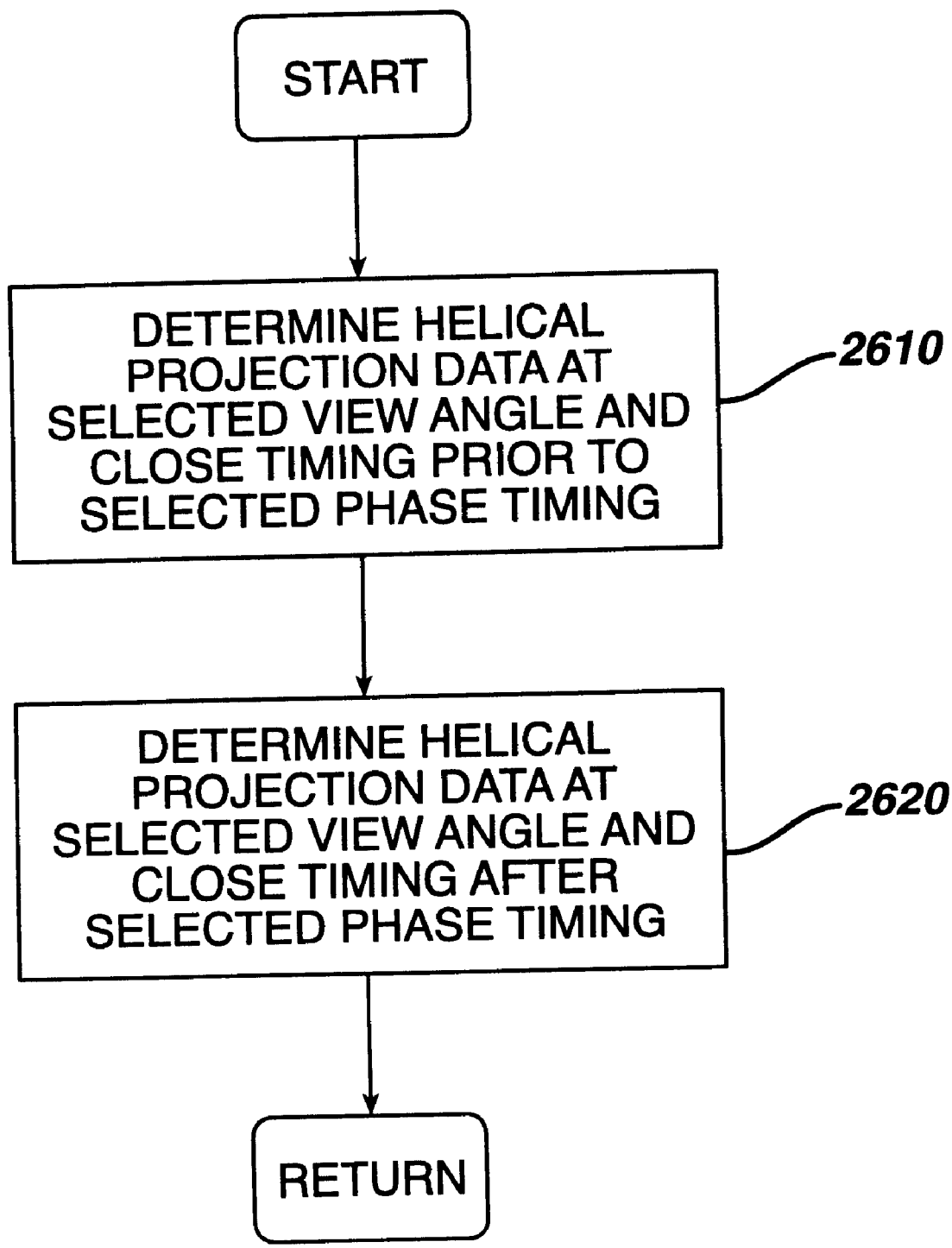
FIG. 26 is a flow diagram illustrating details of an operation for selecting neighboring scanning rotations as shown in FIG. 25.

FIG. 26 shows a flow diagram illustrating an exemplary sequence of operations for performing the operation 2550 of FIG. 25. The context for this procedure is that the helical projection data comprise data for a succession of scanning rotations each including the selected view angle. However, because the cardiac cycle will not be synchronized with the scanning rotations, the data for the selected view angle from different scanning rotations generally will represent the heart at different cardiac phases.

Operations 2610 and 2620 determine particular helical projection data (such as by selecting particular scanning rotations) for which the selected view angle corresponds to respective cardiac phases near the selected phase. The operation 2610 determines such data for a nearby phase timing prior to the timing of the selected phase, and the operation 2620 determines data for a nearby phase subsequent to the selected phase.

For example, with reference to the trajectories of FIG. 8, the trajectories 3 and 2 would be selected as neighbors for (i.e., before and after) the selected phase $t_o$, for all view angles θ between 0° and 60°. For θ between 60° and 180°, trajectories 1 and 3 would be selected; for θ between 180° and 300°, trajectories 2 and 1 would be selected; and for θ between 300° and 360°, trajectories 3 and 2 would be selected. It is desirable for the procedure to select those scanning rotations for which the selected view angle occurs at a cardiac phase closest to the selected cardiac phase.

Figure 27:
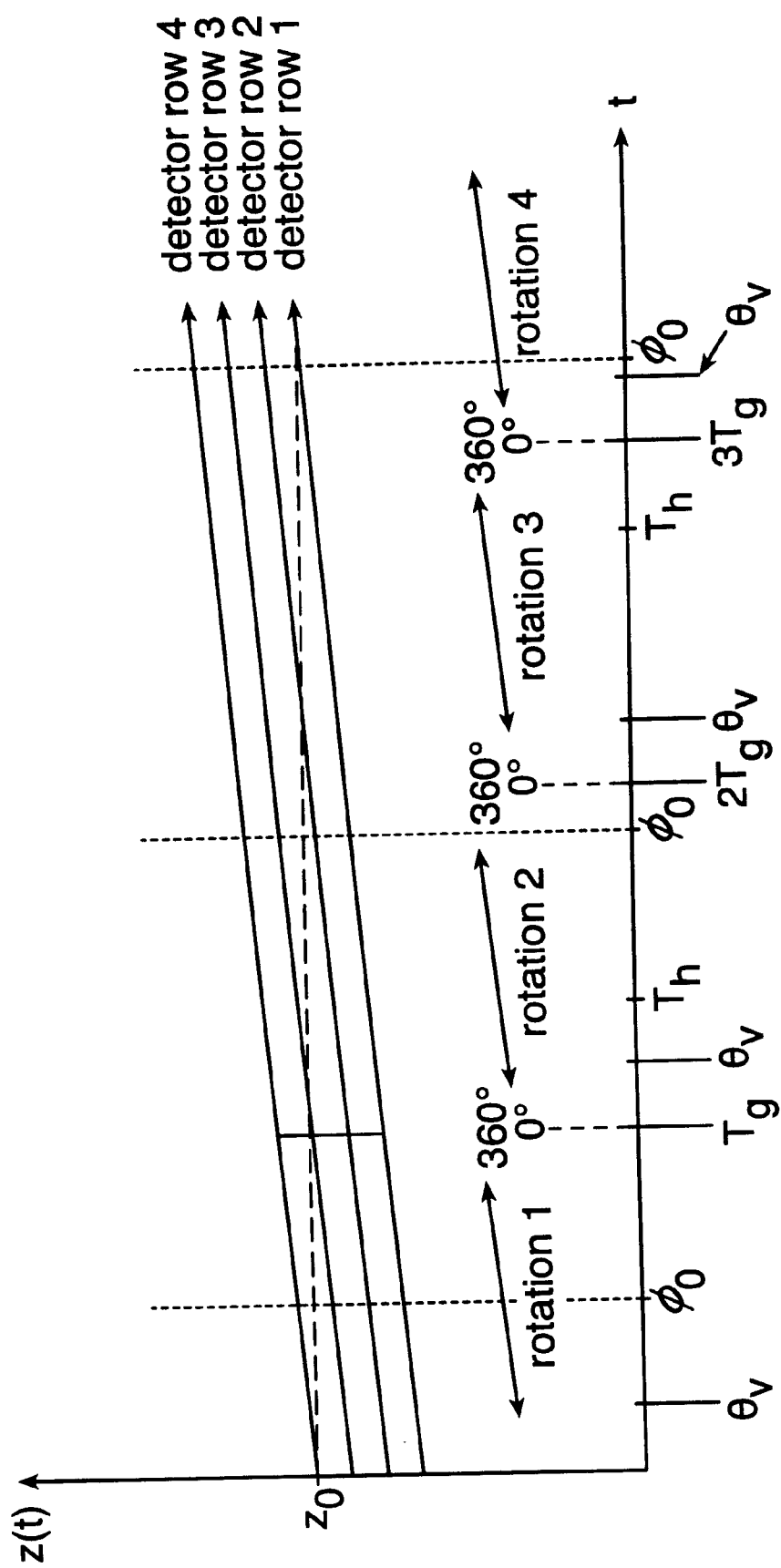
FIGS. 27–28 are diagrams illustrating operations of the procedure shown in FIG. 26.
Figure 28:
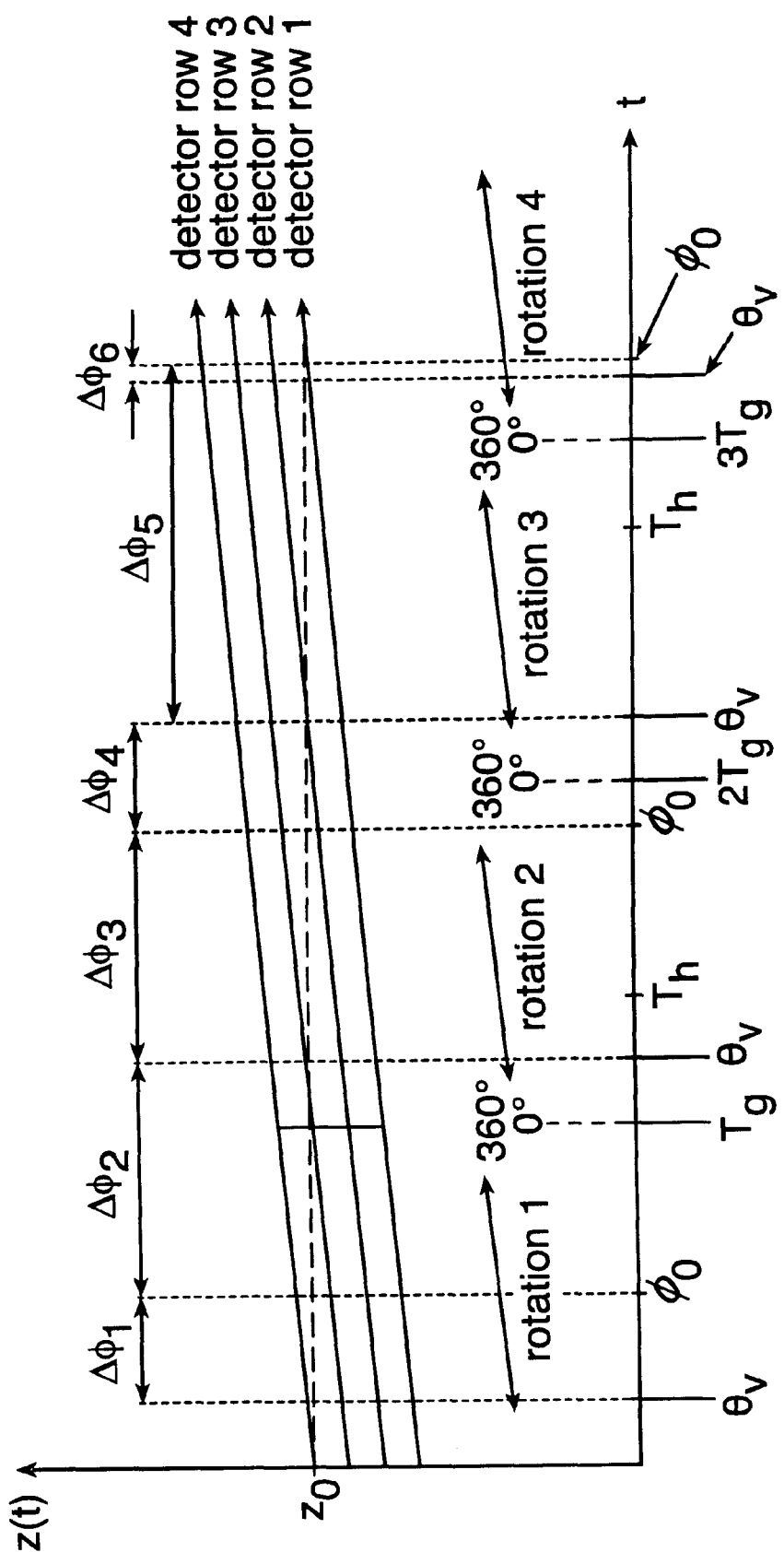

FIGS. 27–28 illustrate the determinations of operations 2610 and 2620. In FIG. 27, each of scanning rotations 1, 2, and 4, the timing of the selected phase is denoted as $\phi_0$. The scanning rotation 3 lacks an occurrence of the selected phase, reflecting the fact that in the illustrated example the cardiac cycle period $T_h$ is longer that the scanning rotation period $T_g$. The selected view angle is denoted $\theta_v$ and occurs in every rotation, including rotation 3.

FIG. 28 illustrates determination of scanning rotation sets for operations 2610 and 2620. In a preferred embodiment, the rotations are ones in which the selected view angle occurs at a cardiac phase close to an occurrence of the selected phase. FIG. 28 shows that the phase differences between the phase at the selected view angle $\theta_v$ and the selected phase $\phi_0$ are represented as phase differences $\Delta\phi$.

The designation of phase differences $\Delta\phi$ emphasizes that the present invention may determine a working projection view based on the difference between the phase of the heart at the working view and the desired phase An interpolation rule used in the present invention may account for the relative phase differences of two working projection views and may give greater weight to a working view that is closer in phase than a working view that is farther away. As indicated above with reference to FIGS. 17–19, the actual phase difference may be better determined by a delay following a most recent trigger wave in the EKG (such as an R-wave), rather than a uniform phase timing such as timing $\phi_0$ in FIG. 12.

Returning to FIG. 28, the view angle $\theta_v$ in rotation 1 occurs at a phase delay $\Delta\phi_1$ a way from the occurrence of the phase $\phi_0$. In rotation 2, view angle $\theta_v$ occurs $\Delta\phi_2$ away from $\phi_0$ in rotation 1 and $\Delta\phi_3$ away from $\phi_0$ in rotation 2. Similarly, in rotation 3 $\theta_v$ occurs $\Delta\phi_4$ away from $\phi_0$ in rotation 2 and $\Delta\phi_5$ away from $\phi_0$ in rotation 4. $\theta_\nu$ in rotation 4 occurs $\Delta\phi_6$ away from $\phi_0$ in the same scanning rotation. Of course, additional scanning rotations will generally provide additional occurrences of $\theta_\nu$ at corresponding phase differences $\Delta\phi$ away from $\phi_0$.

The selection of neighboring scanning rotations in operation 2550 (see FIG. 25), performed in operations 2610 and 2620 of FIG. 26, may select a pair of rotations for which the selected view angle $\theta_\nu$ occurs at a timing close in phase to the desired phase $\phi_0$. In a particular case, $\theta_\nu$ may occur in the selected rotations at the closest phases before and after phase $\phi_0$, respectively, among the collected projection data. Thus, rotation 4 will be selected because $\theta_\nu$ occurs closest in phase to $\phi_0$ of the available rotations. The occurrence of $\theta_\nu$ in rotation 3 is the closest occurrence after an occurrence of $\phi_0$, among the available rotations. It should be observed at this point that the selected rotations 3 and 4 are temporally consecutive data acquisition cycles, a natural consequence of selecting the closest trajectories before and after the desired phase.

It follows that the exemplary embodiment illustrated in FIG. 28 determines the helical projection data in operation 2610 as the data at $\theta_\nu$ in rotation 4. The data determined in operation 2620 are, in like manner, the data at $\theta_\nu$ in rotation 3.

In summary, the illustrated embodiment of the procedure selects the nearest neighbor scanning rotations before and after the selected phase. The possibility exists to interpolate between view angles corresponding to other scanning rotations, as well, as noted above with reference to FIG. 20. Such alternatives will be described in more detail below with reference to FIGS. 31–36.

Figure 29:
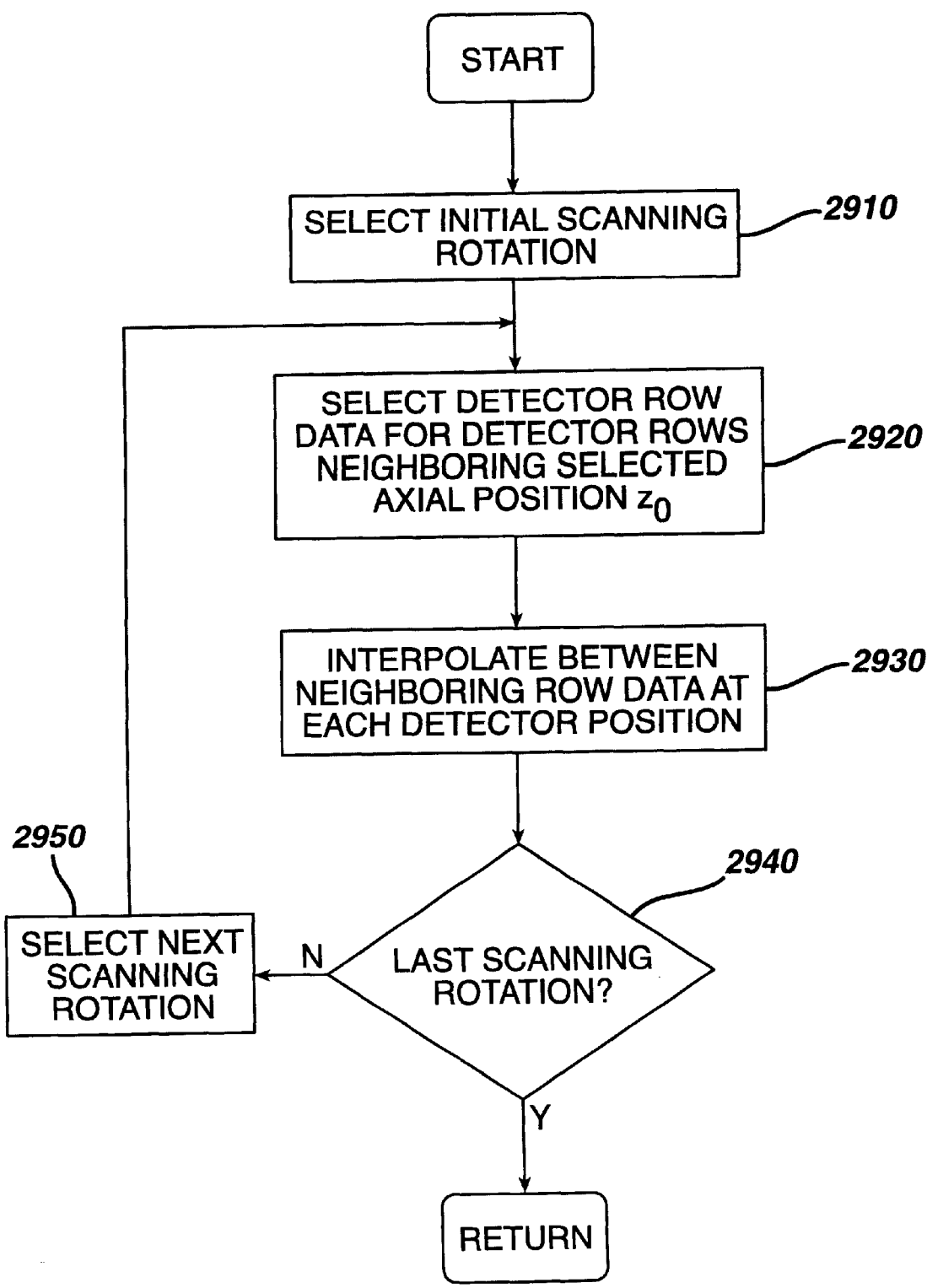
FIG. 29 is a flow diagram illustration details of an operation for determining working projection views as shown in FIG. 25.

FIG. 29 shows a flow diagram illustrating an exemplary sequence of operations for performing the operation 2560 of FIG. 25. The result of these operations is to determine for each selected scanning rotation a projection view representing the subject at the selected axial position. As noted above, the helical scan data is usually collected with a multi-row detector and cone beam.

An operation 2910 selects an initial scanning rotation from the selected scanning rotations for which working projection views are to be determined. The selected axial position will generally fall between the axial positions for two detector rows of the selected scanning rotation at the selected view angle. FIG. 27 shows that the axial position of each detector row advances as the view angle of the rotation increments from 0° to 360°. For the selected view angle, operation 2920 determines from the selected scanning rotation the two rows closest to the selected position $z_0$.

Figure 30:
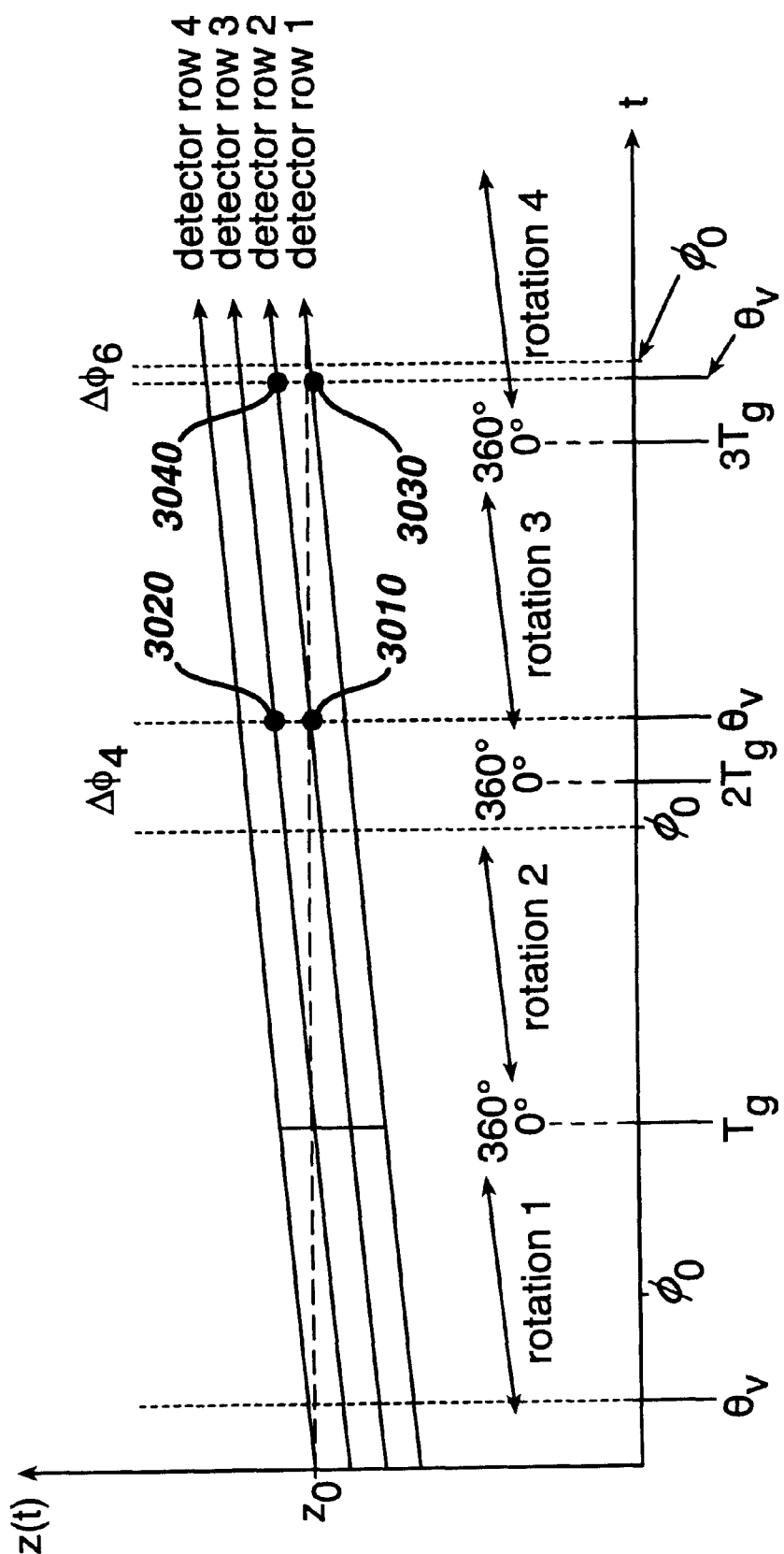
FIG. 30 is a diagram illustrating application of the procedure of FIG. 29.

FIG. 30 is a time evolution diagram, similar to FIGS. 27–28, showing the helical projection data determined in the procedure of FIG. 26. As seen in FIG. 30, the helical projection data will usually comprise several rows of data corresponding to the rows of detector elements arranged successively in the axial direction. In the typical case, as illustrated in FIG. 30, none of the selected data rows will provide a projection view at the selected axial position $z_0$. This is a common occurrence with helical scanning data and arises because of the axial translation of the detector array during the scanning rotation. A projection view for the selected position $z_0$ will therefore be constructed from the existing helical projection data.

FIG. 30 also illustrates the scanning rotations and data rows that may be selected in operations 2910 and 2920. For the purposes of this illustration, it is assumed that the scanning rotation 3 is the selected initial scanning rotation. The two data rows 3010 and 3020, respectively below and above $z_0$ in the axial direction Z, comprise the neighboring detector row data selected in the operation 2920.

Returning to FIG. 29, projection data for an interpolated projection view at the selected position $z_0$ are then computed at an operation 2930. Here the interpolated projection data are generated by interpolating in z (the axial direction) between the neighboring row data at each detector position along the selected rows. In some respects this computation resembles a grid transformation operation, whereby the available data are converted to projection data for a different grid. Such transformations are well known in the art, and the various available alternatives for carrying out the corresponding computations will not be detailed here. In a typical such alternative, the data values of the z-interpolated projection view are obtained according to a formula such as $$P_{ij}(\theta, z_0) = \sum_{\substack{k \\ ijk \ni |Z_{ijk}(\theta) - z_0| \leq \Delta_d}} \omega_k(z_0) \cdot P_{ijk}(\theta), \quad \text{where} \quad (6)$$

$$\omega_k(z_0) = G(|Z_{ijk}(\theta) - z_0|), \quad \sum_k \omega_k(z_0) = 1.$$

Here k indexes the rows of the multi-row detector array, $Z_{ijk}(\theta)$ is the z-location of the projection view $P_{ijk}(\theta)$, and $\Delta_d$ is the collimation (which, as noted previously, is the inter-row distance). It is also noted that the projection views $P_{ijk}(\theta)$ for given $\theta$, i and j have the same phase $\Phi_{ij}(\theta)$ for all rows k. This commonality arises because in such a case the projections of all the rows are collected at the same moment in time.

The weights $\omega_k(z_0)$ may be defined in terms of a function $G(\cdot)$ of the distance $|Z_{ijk}(\theta) - z_0|$, where G is a non-negative monotonically decreasing function of its argument. For example, G may be a linear function of the distance $|Z_{ijk}(\theta) - z_0|$. The idea behind this z-interpolation, like the phase interpolation described previously, is that the closer a projection view is to $z_0$ (or $\phi_\theta$), the more that projection view contributes to the interpolated projection view. As with the previous discussion of weights for phase interpolation, those of skill in the art will appreciate that many weighting schemes may be employed to carry out z-interpolation with the present invention.

An operation 2940 determines whether working projection views are to be determined for more scanning rotations. If so, then the procedure advances to an operation 2950 where the next of the selected scanning rotations is selected for interpolation. For example, in FIG. 30 the next scanning rotation would be scanning rotation 4. The procedure of FIG. 29 then returns to operation 2920. The two data rows 3030 and 3040, respectively below and above $z_0$, comprise the neighboring detector row data selected in the operation 2920. The operation 2930 then interpolates between rows 3030 and 3040 to generate the second working projection view at the selected axial position $z_0$.

In the procedure of FIG. 26 the operations 2610 and 2620 will be performed twice. At the completion of the procedure illustrated in FIG. 29, there will have been determined two (or more) separate working projection views each computed by interpolation in z between neighboring detector rows of the respective scanning rotation data. At this point the procedure of FIG. 25 continues as described above.

Flexible Projection Data Processing

A further alternative embodiment of the invention will now be described with reference to FIGS. 31–35. A procedure of this alternative bears some similarities to the procedure of FIG. 14 above. The result to be obtained may be a 3-D image of the patient's heart at a desired cardiac phase $\phi_0$. A three-dimensional image (a volumetric representation based on several slice images) of the subject's heart may be obtained through this alternative embodiment by reconstructing 2-D slices for a range of z-locations ($z_0$). For each two-dimensional slice, the system may obtain a slice image corresponding to the given phase $\phi_0$, as well as the axial position of the slice.

Figure 31:
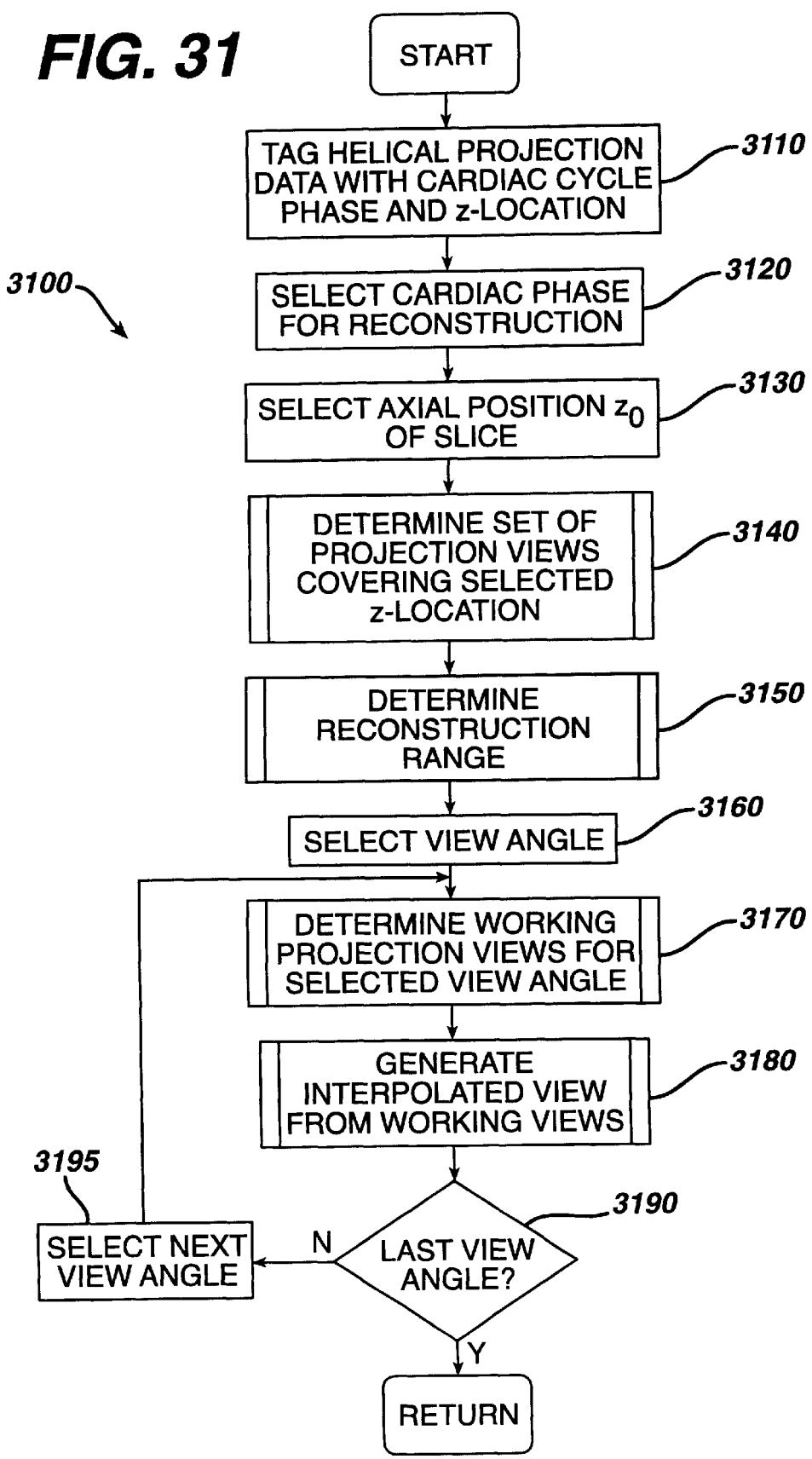
FIG. 31 is a flow diagram illustrating a procedure of another aspect of the present invention as applied to the particular context of multiple-row helical scanning for cardiac imaging.

FIG. 31 is a flow diagram illustrating a procedure 3100 of this alternative embodiment of the invention for the case of helical scan data. In an operation 3110 the three-dimensional projection data are tagged with phase and z-location information. Based on the temporal location of the identified R-wave peaks, as described above with reference to FIG. 11, each projection view is assigned a cardiac phase $\Phi_{ijk}$. In this operation the gantry period $T_g$ is also used to determine the gantry rotation of the projection view. Similarly, the z-locations of the projection views are determined based on the relationship between the gantry period $T_g$ and the table speed, as indicated above with reference to FIG. 24. The phase and z-location tags are used in the subsequent operations of the procedure 3100.

An operation 3120 selects a cardiac phase at which a slice image of the patient's heart is to be reconstructed. A corresponding axial position $z_0$ for the slice image is selected in an operation 3130. These operations specify the slice image and enable the appropriate projection data to be identified by reference to the phase and location tags.

An operation 3140 determines, from among the helical projection data, the set of projection views from which an interpolated projection view for the slice image may be generated. Given the selected z-location $z_0$, the projection views that possibly could contribute to the interpolation result of equation (4). As noted above, for a given axial position either one or two data rows of the helical projection data correspond to row positions that are closest to the selected axial position $z_0$. The projection data were tagged with location information in the operation 3110, and therefore the data rows can be searched for the one or two nearest neighbors to $z_0$.

Operation 3150 determines a reconstruction range in which to obtain a complete set of projection views for the selected slice image. The operation 3170 determines working projection views for the selected view angle by interpolating in the z-direction between the neighboring projection views as determined by the location tags $Z_{ijk}(\theta)$. This operation determines a reconstruction range, i.e., a range of view angles (the range having extent (180°+ fan angle) from among the full range [0°, 360°]. Here a "reconstruction range" comprises a plurality of discrete view angles, because the projection data are sampled in discrete sampling intervals. A set of projection data is said to "cover" a given reconstruction range if the set of projection data comprises a projection view at each of the discrete view angles of the reconstruction range.

The reconstruction range is selected as a subset of the projection views covering the selected axial position (see operation 3140) for which the total phase distance from the selected phase $\phi_0$ is a minimum. The operation 3150 will be described in more detail with reference to FIG. 33. An operation 3160 selects an initial view angle at which an interpolated projection view will be generated.

Operations 3170 and 3180 are repeated for each view angle in the selected reconstruction range. This interpolation may be carried out substantially as described above with reference to FIG. 29.

The operation 3180 performs phase interpolation between the z-interpolated projection views obtained from the operation 3170, using the selected interpolation rule of the form (4) above. Alternatively, the interpolations of operations 3170 and 3180 may be performed in an integrated computation, using an interpolation rule such as $$P_\phi(\theta) = \sum_{i,j,k} w_{ij}\omega_k P_{ijk}(\theta). \quad (7)$$

It is further noted that the separated weight $w_{ij}\omega_k$ may be replaced with an integrated weight $\Omega_{ijk}$.

The procedure 3100 advances from the operation 3170 to an operation 3180 that determines whether more view angles in the selected reconstruction range remain for interpolated projection views to be generated. If so, then an operation 3190 selects the next view angle and the procedure loops back to the operation 3150. If not, the procedure 3100 returns.

Figure 32:
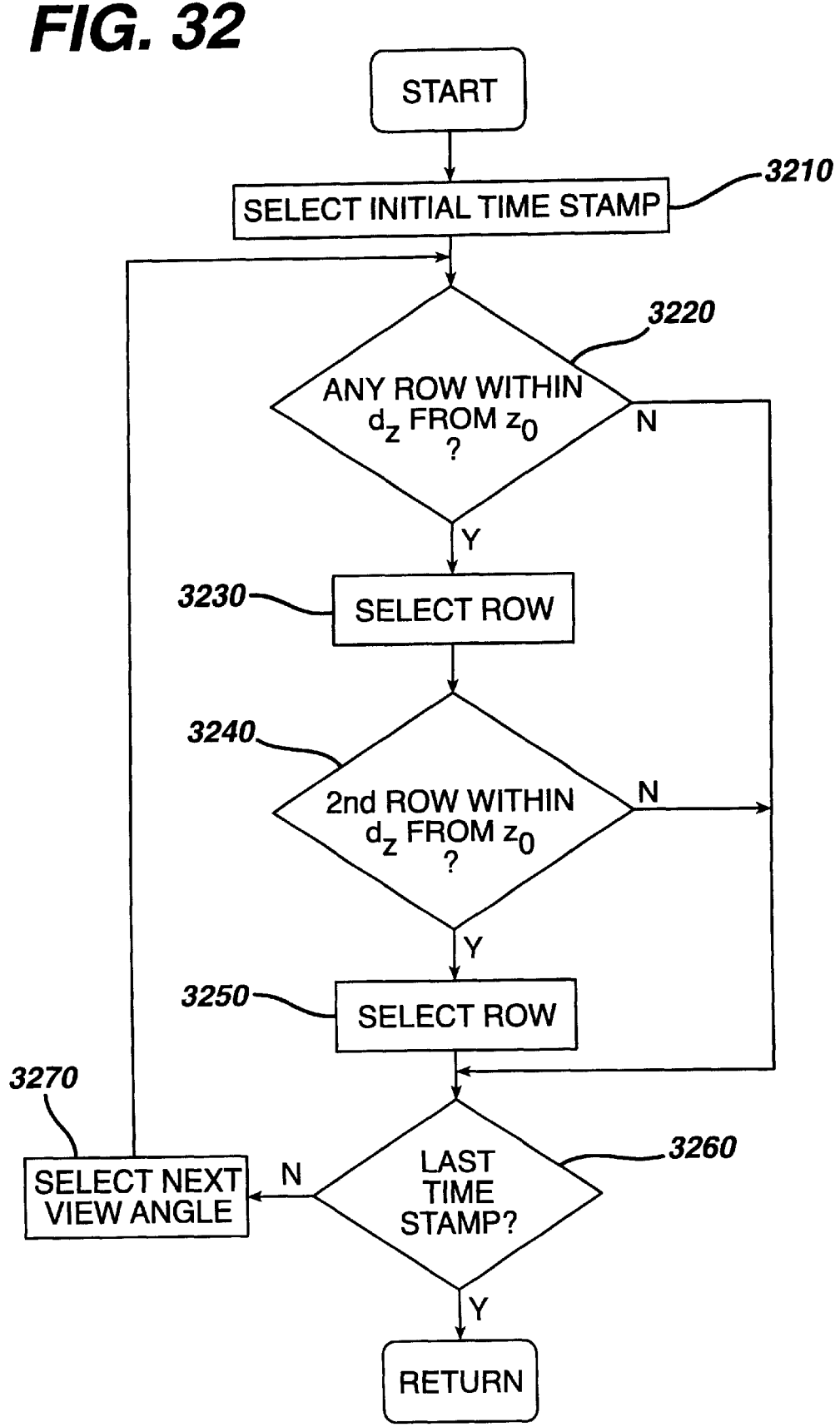
FIG. 32 is a flow diagram illustrating a procedure for determining a set of projection views for a selected axial position.

FIG. 32 is a flow diagram illustrating details of an exemplary procedure for carrying out the operation 3140 of FIG. 31. An operation 3210 selects an initial time stamp corresponding to an initial sampling interval of the (three-dimensional) helical projection data. This identifies the projection data rows generated first in time among the helical data.

From the operation 3210 the procedure of FIG. 32 enters an iterative loop in which rows of data are examined for possible inclusion in the set of selected projection views. An operation 3220 determines whether any data row corresponding to the current time stamp is tagged with a z-location within the collimation distance $\Delta_d$ from the selected axial position $z_0$. If such a row is identified, the row is selected for the set of projection views in an operation 3230.

The procedure of FIG. 32 advances from the selection operation 3230 to an operation 3240 in which it is determined whether the projection data comprise a second row within the collimation distance $\Delta_d$ from the z-position $z_0$. If so, the second row is selected for the set of projection views. As noted above, for any given data sampling interval (i.e., any given time stamp) will correspond to at most two data rows tagged with z-locations within the collimation distance from a selected axial position.

If the determination at either the operation 3220 or the operation 3240 is negative, then the procedure advances directly to an operation 3260. The operation 3260 determines whether all the time stamps for the collected projection data have been considered. If not, then the procedure advances to an operation 3270 where a next time stamp is selected. From the operation 3270 the procedure loops back to the determination at the operation 3220. If the determination at the operation 3260 is affirmative, then the procedure returns. Alternatively, instead of looping back based on the determination of operation 3260, the procedure of FIG. 32 may instead continue until a row of data has been selected at a time stamp and no row of data is selected at a subsequent time stamp, or until all of the time stamps have been considered, whichever occurs first. This alternative may be more efficient because a final block of rows that comprises no selectable rows will not be searched.

Figure 33:
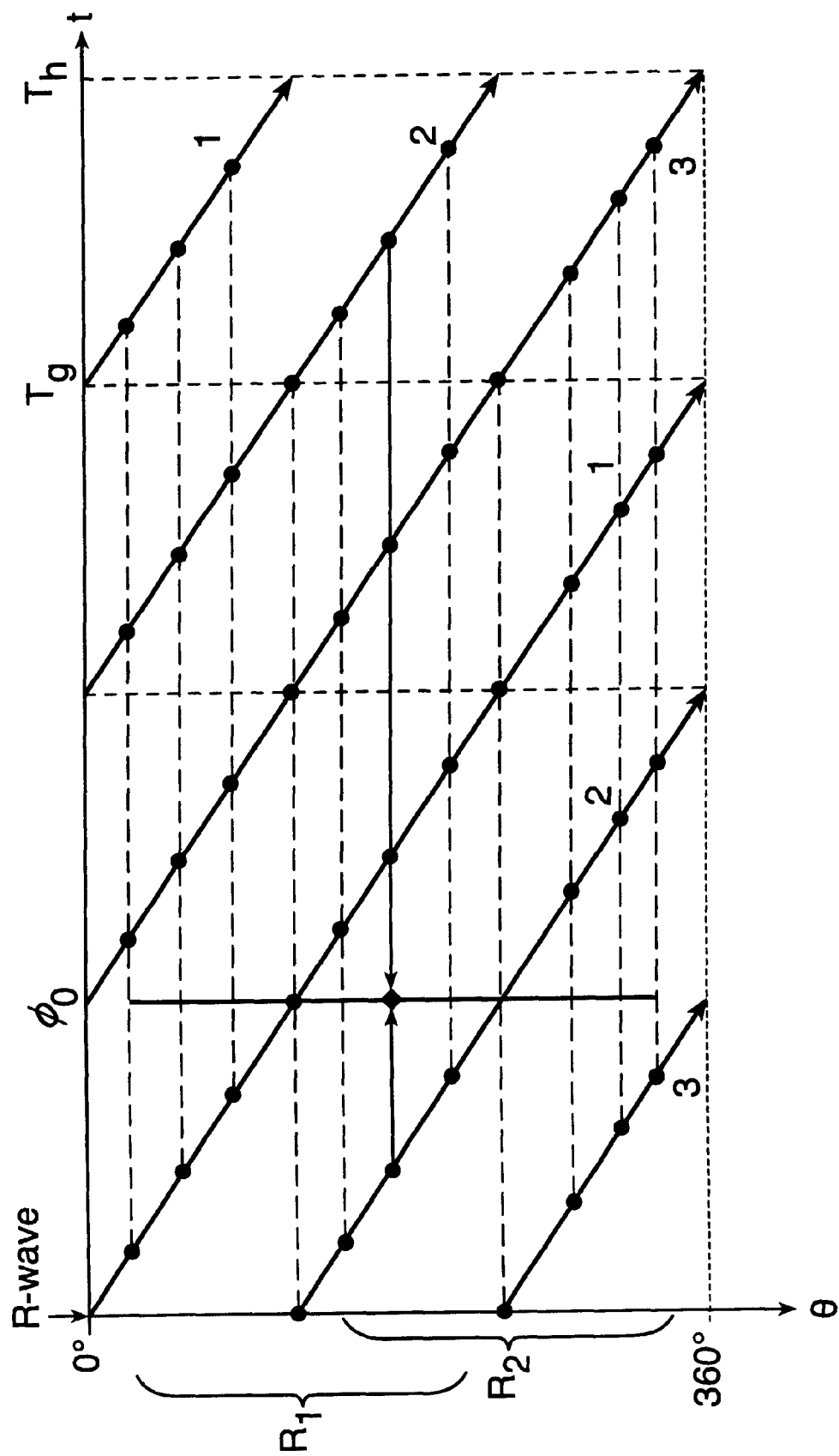
FIG. 33 is a trajectory diagram illustrating multiple reconstruction ranges in a set of projection views for a selected axial position.

FIG. 33 is a trajectory graph, similar to the graph of FIG. 20, for illustrating the operation 3150 of FIG. 31. The filled circles 3310 each represent projection data corresponding to a respective data sampling interval. The data acquisition cycles of the imaging system 100 provide several trajectories 1, 2, 3 of projection data. Each trajectory, although discretized in time and hence also in view angle, nevertheless covers the full range [0°, 360°] of view angles.

Moreover, for each discrete view angle in the range [0°, 360°], the projection data comprise several sets 3310 of projection data having time stamps corresponding to the given view angle. Thus, as in FIG. 20, an interpolated projection view could be generated for each discrete view angle from the existing sets of projection data at that view angle.

On the other hand, as noted above, current reconstruction algorithms generally can produce high quality image reconstructions with projection data covering less than the full range [0°, 360°]. The projection views should cover an angular sector of at least 180° plus the fan angle. FIG. 33 illustrates that this condition may be satisfied by several different sets of projection views covering different sectors of view angles. The several trajectories 1, 2, 3, etc., therefore comprise more projection data than is necessary for the desired image reconstruction.

This surplus of projection data presents a potential opportunity for optimizing the image quality by carefully selecting the reconstruction range for the desired image. Here a reconstruction range $\Theta_r$ is simply the range of view angles of the projection views from which the slice image will be reconstructed. The perspective of the projection data afforded by the trajectory graph of FIG. 33 raises the possibility that different reconstruction ranges may provide reconstructed images with different features.

Yet another aspect of the present invention provides an approach for determining a reconstruction range that will optimize some data parameter having an influence on image quality. In one implementation of this aspect of the invention, a reconstruction range is selected that has a minimum total phase distance from the desired phase. Here, "minimum total phase distance" means the smallest distance value defined by the following formula:

$$D(\theta_1, \theta_2) = \sum_{\theta \in K_r = [\theta_1, \theta_2]} d(\theta, \phi) \qquad (8)$$

where the reconstruction range $R_r$ extends between beginning and ending view angles $\theta_1$ and $\theta_2$, respectively. The total phase distance is a "separation measure" for the reconstruction range, because the total phase distance measures a separation (in phase) between the existing projection views of the reconstruction range and an ideal set of projection views (e.g., all at the desired phase). The value $d(\theta, \phi)$ is selected as the minimum phase distance between the phase of the current projection view and the desired phase, as follows:

$$d(\theta, \phi) = \arg \min_{i,j} |\Phi_{ij}(\theta) - \phi|. \qquad (9)$$

Those of skill in the art will appreciate that the reconstruction range $R_r$ may begin at an angle $\theta_1$ that is actually larger than the ending angle $\theta_2$, due to the periodicity of $\theta_1$. In such a case the representation $[\theta_1, \theta_2]$ for the reconstruction range $R_r$ in equation (2) above may be replaced by the corresponding representation $R_r = [\theta_1, 2\pi) \cup [0, \theta_2]$.

In the foregoing particular example the detector array has four rows of detectors. In this exemplary case it follows from simple geometry that the number of gantry rotations contributing projection views for a given z-location is determined by 4/p, where p is again the pitch of the helical scan. The pitch p may be selected to be small enough that multiple projection views are generated for the same view angle, although from different gantry rotations and cardiac cycles. Depending on the heart rate, these projection views will represent the heart in a distribution of cardiac phases.

Therefore, in a first procedure, the temporal (phase) distance $d_{ij}$ of each projection to the reconstruction (target) phase $\phi_0$ will be determined. Each of these phase distances indicates a separation (in phase) between the projection view and an ideal projection view (at the desired phase), and thus each is a "separation value" for the respective projection view. Then, for each view angle, the minimum temporal distance is found and used with equations (8) and (9) to determine the start angle $\theta_s$ and the end angle $\theta_e$ of the least-distance reconstruction range. The result is a reconstruction range with a subset of projection views that are closest in phase to the reconstruction phase $\phi_0$.

Figure 34:
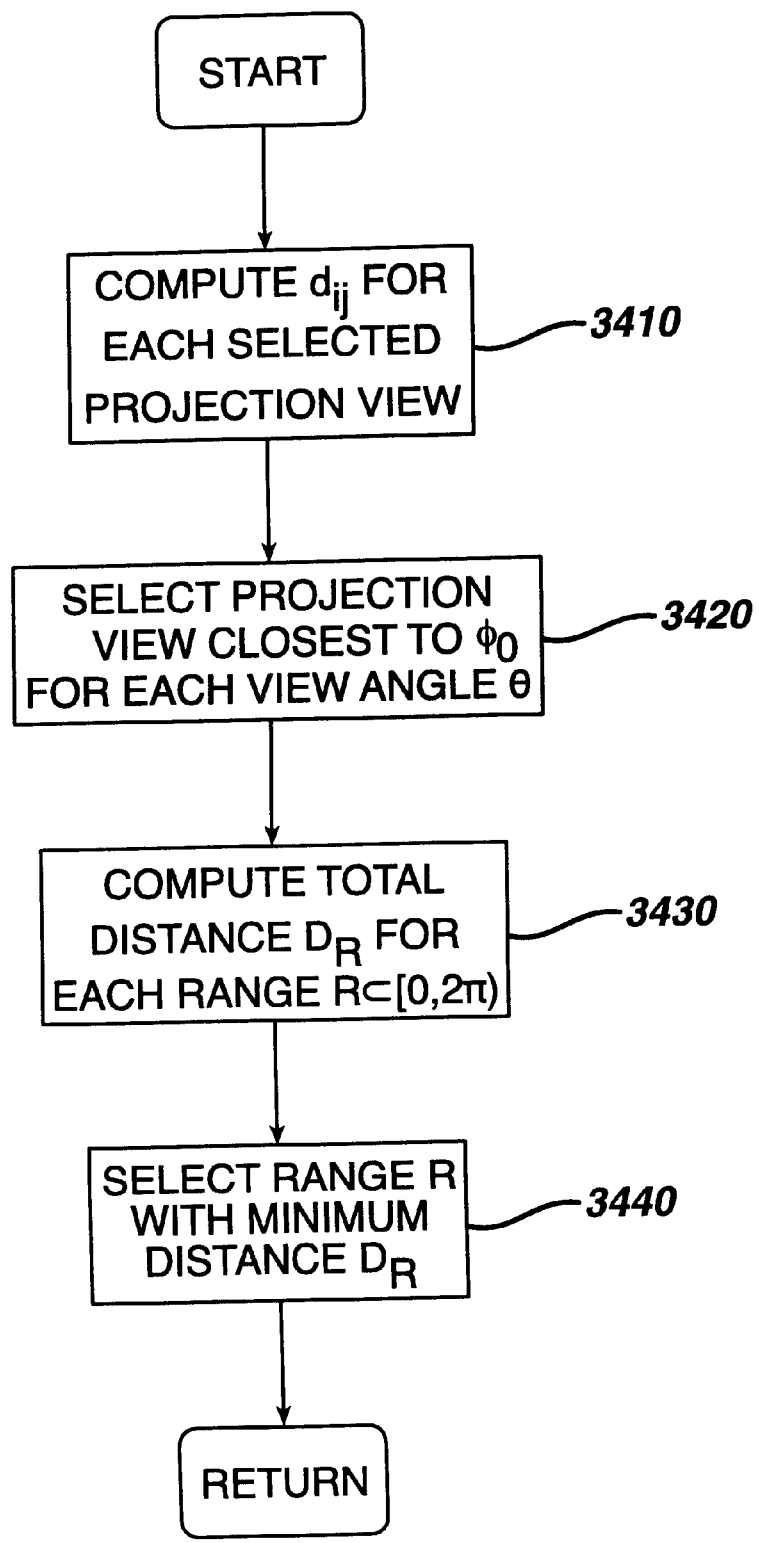
FIG. 34 is a flow diagram illustrating a procedure for selection of a particular reconstruction range in which to perform phase interpolation between projection views.

FIG. 34 is a flow diagram illustrating a procedure of this further aspect of the invention for determining such a reconstruction range. An operation 3410 computes the phase difference $d_{ij}$ for each projection view in the selected set of projection data. An operation 3420 then selects a projection view closest in phase to the desired phase $\phi_0$, for each view angle. A total $D_R$ of these minimum distances is computed at an operation 3430 for each potential reconstruction range in the full sector [0°, 360°). A particular reconstruction range whose total distance $D_R$ is a minimum relative to the other reconstruction ranges is selected in an operation 3440, and the procedure of FIG. 34 returns.

Figure 35:
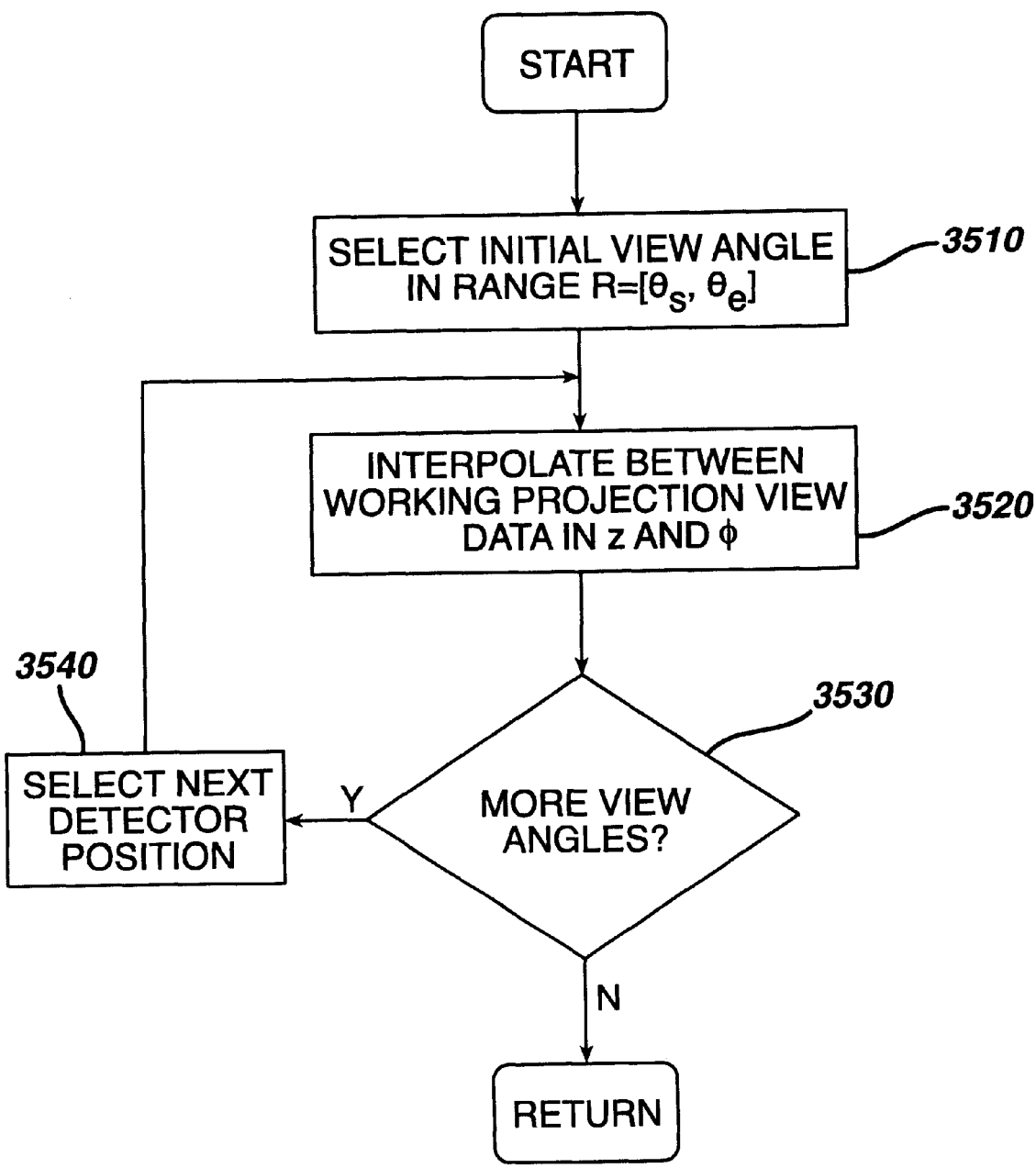
FIG. 35 is a flow diagram illustrating phase interpolation between projection views for view angles in a selected reconstruction range.

FIG. 35 is a flow diagram illustrating an exemplary procedure of the invention for determining the interpolated projection views for a selected reconstruction range. An operation 3510 selects an initial view angle in the selected range. It is noted that the reconstruction range may be represented by an angular interval $[\theta_s, \theta_e]$, so that the initial view angle may be $\theta_s$. An operation 3520 interpolates between the row data of the projection views selected for the view angle. An operation 3530 determines whether more view angles remain at which to generate interpolated projection views. If more view angles remain, an operation 3540 selects the next view angle, and the procedure loops back to the operation 3520.

Figure 36:
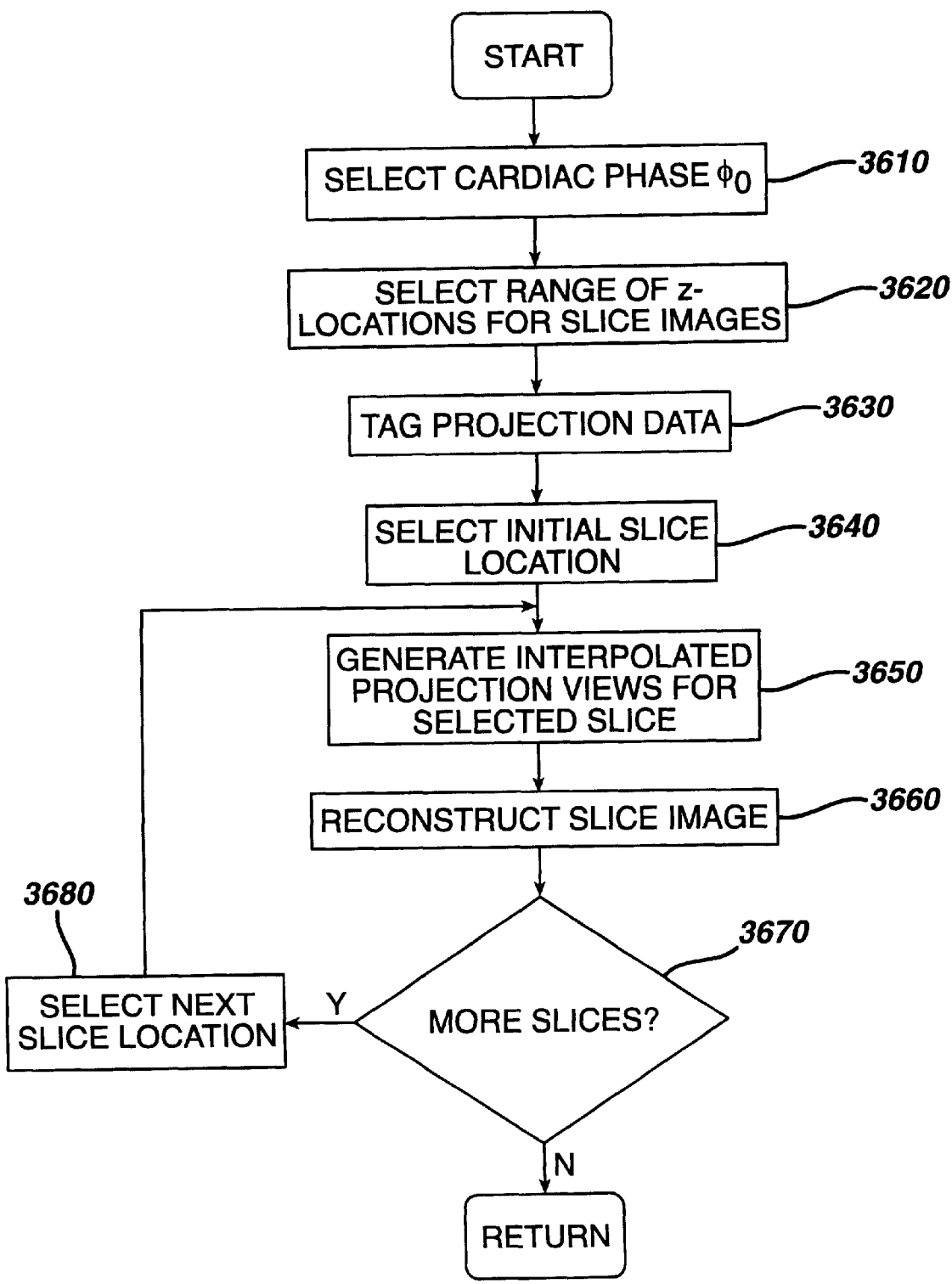
FIG. 36 is a flow diagram illustrating a procedure for generating a set of tomographic slice images using phase interpolation between projection views.

FIG. 36 is a flow diagram outlining an overall procedure of the invention for generating a set of slice images for a corresponding range of axial positions z. Where the set of slice images comprises a plurality of images, this procedure effectively provides for generating a volumetric image of the object of interest. The direct result of the particular procedure as illustrated is a three-dimensional representation of the patient's heart at a selected phase of the cardiac cycle. Persons of skill in the art will appreciate that this basic procedure may be employed for a range of selected phases to generate a dynamic model of the patient's heart, for purposes such as dynamic functional assessment.

An operation 3610 selects the desired cardiac phase $\phi_0$. An operation 3620 similarly selects a range of axial (z-axis) locations for the slice images to be generated. An operation 3630 tags the projection data with phase identification information and z-location information, as described previously with reference to FIGS. 11 and 24. An operation 3640 selects an initial slice location ($z_0$).

Operation 3650 generates interpolated projection views for the selected slice by phase interpolation, as provided by the various aspects of the present invention. A complete set of projection views is thereby generated for the selected slice, perhaps with supplementation from the existing views of the projection data. Operation 3660 performs reconstruction on the complete set of projection views, using any of various well-known methods for tomographic image reconstruction. An operation 3670 determines whether more slice images remain to be generated. If so, the procedure advances to operation 3680 where the next slice position is selected, and the procedure then returns to the operations 3650 and 3660.

A Technique for Re-ordering Data in the Phase Domain

The foregoing exemplary embodiments illustrate an aspect of the invention that provides advantages for tomographic imaging of objects in motion. This aspect of the invention provides for reconstruction of a tomographic image from projection views that have been processed to account for dynamic behavior of the imaged object during collection of the projection data [θ(n), Z(m)].

The examples described above further illustrate that such processing to account for dynamic behavior may be carried out in various alternative ways. For example, the adaptive processing approach of the first embodiment described above is oriented toward independent sets of projection data where each set corresponds to a single axial position z. In this sense, the first embodiment may be described as "position driven." When the raw data [θ(n), Z(m)] are obtained by helical/cone beam scanning, further processing (rebinning) may be carried out to assemble the helically skewed data into a sequence of such independent sets for successive axial positions. This rebinning procedure typically entails an interpolation procedure between detector element values of neighboring detector rows, such as z-interpolation as described above.

An additional technique for preprocessing the raw projection data will now be described. Such preprocessing may be used with the present invention and particularly with "position driven" embodiments as noted above.

This additional technique proceeds from the further observation that useful information potentially exists in relationships between helical scan data in both space and time. The rebinning procedure noted above illustrates that the spatial proximity of adjacent detector rows has been used to synthesize projection data corresponding to a particular axial position. The technique to be described uses the further discovery that the selection of appropriate subsets of the three-dimensional projection data can allow additional information to be extracted from relationships between the raw data collected in different gantry rotations.

One source of this additional information may be the potential for overlap between the helical scan paths of various detector elements in a multi-row detector array. However, it has been recognized also that other relationships may exist between the raw data of different gantry rotations. A particular instance of such relationships will now be described in conjunction with an exemplary embodiment of the present additional technique in the particular context of volumetric cardiac imaging.

Figure 37:
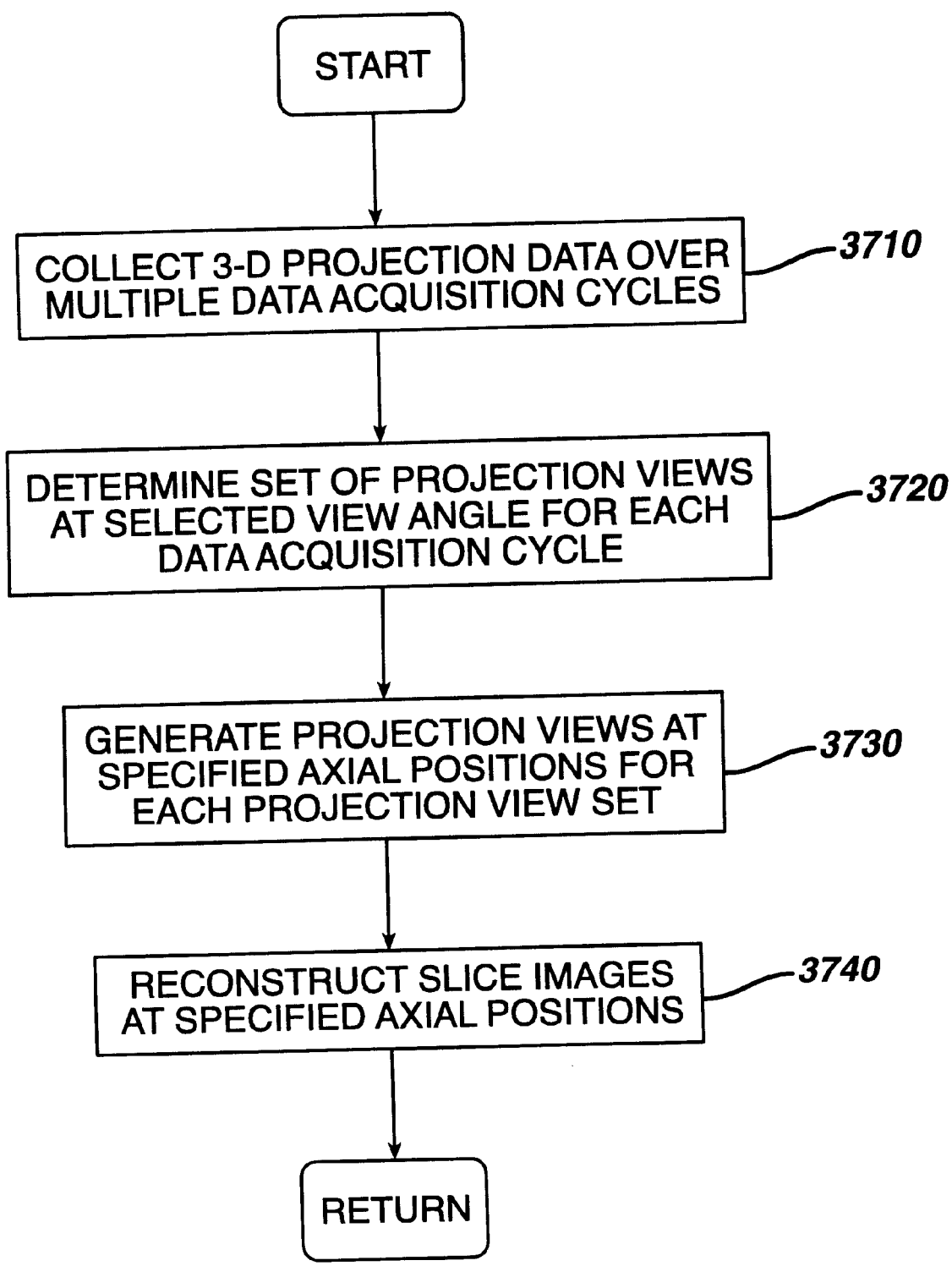
FIG. 37 is a flow diagram of generating reconstructive images in accordance with one embodiment of the present invention.

FIG. 37 is a flow diagram illustrating a general procedure provided by the present additional technique. An operation 3710 is the basic data collection operation for obtaining three-dimensional projection data. If the projection data are generated with a helical scanning system comprising or having a source-detector assembly such as the assembly 2100, then the operation may comprise several rotations of the gantry 2112 to execute multiple data acquisition cycles. In any case, the operation 3710 obtains volumetric projection data representing the imaged object over a plurality of data acquisition cycles.

In an operation 3720, the three-dimensional projection data are analyzed to determine (for example, to select) a particular set of projection views at a selected view angle for each data acquisition cycle. It is desirable to select the view angles for this operation 3720 according to a time dependent feature (i.e., a "dynamic behavior") of the object being imaged. The particular sets of projection views may then be selected to satisfy a predetermined relationship for the time dependent feature between the different sets. A particular case of this determining operation will be described below with reference to FIGS. 40–42.

An operation 3730 provides a reconciliation between the axial positions at which the projection views of a given set represent the object and the axial positions at which the stacked slice images are to represent the object. This reconciliation is typically helpful because the helical projection data are axially skewed within each rotation data set. Thus, with reference to FIG. 23, it will be likely that none of the detector rows will coincide in axial position with a specified position, at least when the view angle θ is chosen according to some other criterion. Thus, to generate projection views representing the object at the specified axial position, a spatial interpolation (such as the z-interpolation described above) is typically carried out in the operation 3730.

An operation 3740 generally completes the procedure by reconstructing a number of slice images (usually several, but possibly only one or two) at the respective specified axial positions. For each slice image, this operation entails selecting projection views from respective ones of the sets of projection views (or from the reconciled sets of projection views). In this way, each slice image may be reconstructed from several projection views representing the object at different view angles but at the same specified axial position.

A particular embodiment of the present additional technique will now be described in the context of cardiac imaging. Persons of skill in the art will appreciate, however, that this technique can also be applied in other medical and non-medical imaging contexts where a time dependent feature of the three dimensional projection data implicitly carries additional information about the imaged object.

As noted above, in the simplest case of cardiac imaging, it may be assumed that the heart rate is constant while the scan data are collected. The desired phase of the heart's cycle of configurations then occurs in each cardiac cycle at a fixed fraction of the heart period $T_h$ following the preceding R-wave. For a given cardiac cycle, a projection view corresponding to the desired heart phase may be identified by reference to the fixed fraction and the time stamps correlating to the cardiac R-wave that begins the cardiac cycle.

The assumption of regular heartbeat simplifies the process of cross-referencing the projection data and the EKG data. In particular, for each R-R heart cycle the desired phase of the heart occurs at the same time $t_0$ after the R-wave of the cycle. The simplifying assumption of regular heart rate thus creates an assumed correlation between the time stamps of the row data and the respective phases of the cardiac cycle.

However, usually the heart rate is not uniform during the data acquisition process. The preferred procedure is then to collect an electrocardiogram (EKG) data set along with the helical scan data. The EKG data set can then be correlated off-line with CT scan data, using the time stamps associated with the raw volumetric projection data. Thereafter, using the time stamps and the correlations to the EKG data, the particular projection data corresponding to a selected cardiac configuration phase can be identified, as in the embodiments described above.

Such an adaptation to heart rate variations is well known in the art and has been used, for example, in the sector approach described above with respect to FIG. 6. Persons skilled in the art will readily appreciate the appropriate measures to be used with the present additional technique to compensate for the presence of heart rate variability. For example, a compensation model is employed in the technique of U.S. Pat. No. 5,997,883 to Epstein et al. noted previously.

On the other hand, an embodiment of the present additional technique is particularly useful in cases where heart rate variability exists. It is known that in most cases where the heart cycle duration varies, the systole period of the cardiac cycle is relatively stable. In other words, the portion of the cardiac cycle that changes in duration most commonly is the diastole period, when the heart is in a relaxed state. This fact can be used to develop a selection criterion for selecting sets of projection views, as in the operation 3720 of FIG. 37.

Figure 38:
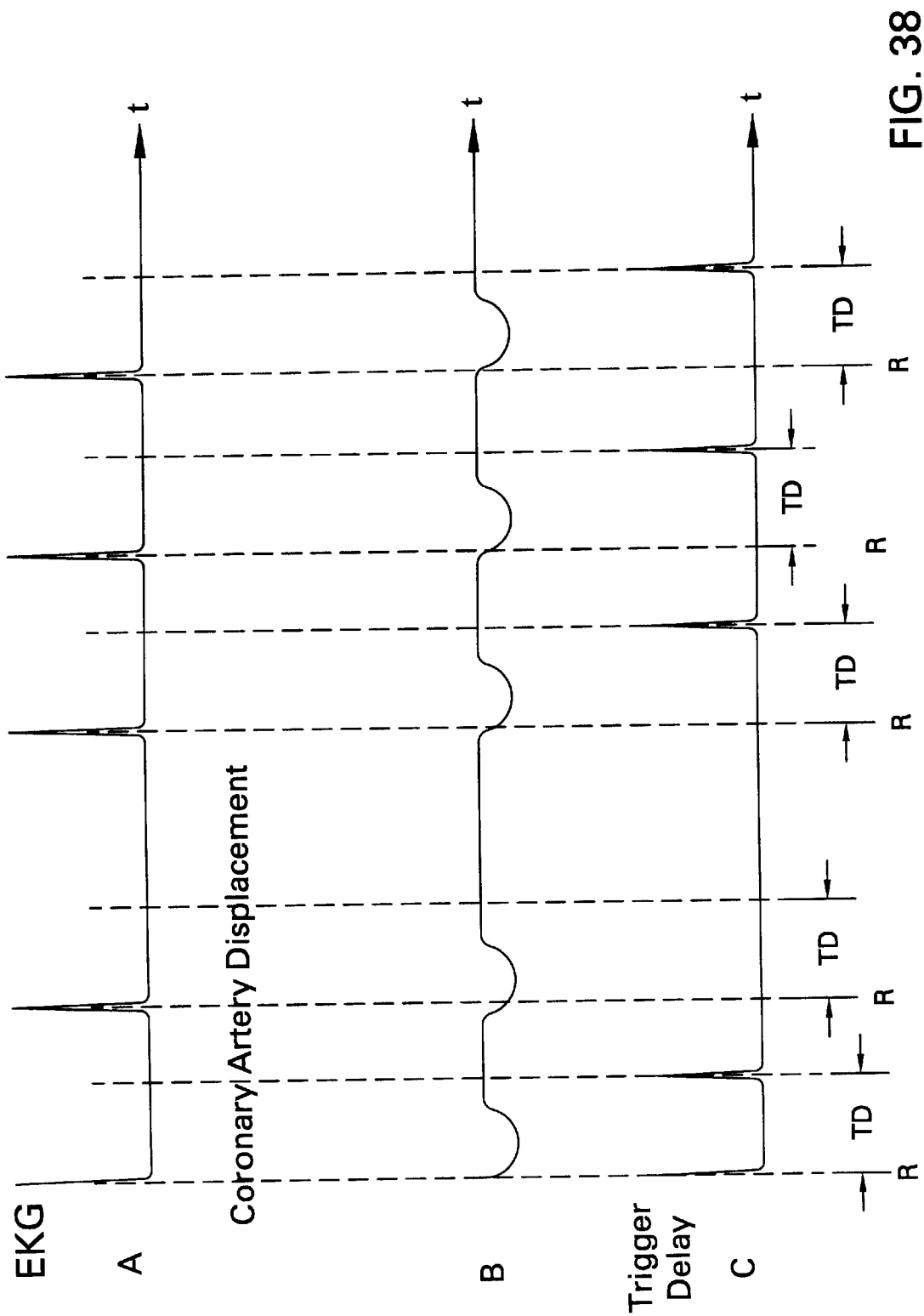
FIG. 38 depicts cardiac timing diagrams with associated trigger delays in accordance with one embodiment of the present invention.

FIG. 38 depicts timing diagrams that illustrate the determination of a trigger delay TD with which to select the projection data sets. In trace A of FIG. 38, the R waves of successive cardiac cycles occur at irregular times, due to the heart rate variability. Trace B of FIG. 38 shows the corresponding displacement of a coronary artery to be imaged.

During the systole period, the displacement is substantial and will tend to create motion inconsistencies in the projection data. However, if a fixed time TD is measured after each R wave, it can be seen that the heart has entered the quiescent diastole period. As trace B of FIG. 38 illustrates, the duration of the diastole period may vary substantially from cardiac cycle to cardiac cycle. However, the entering portion of the diastole occurs reliably at the delay time TD after the R wave.

Trace C of FIG. 38 illustrates the timing of trigger signals by which to select the sets of projection views from the three-dimensional projection data. By generating a trigger signal at a fixed trigger delay TD after each R wave, sets of projection views can be selected from the volumetric data to represent the heart in a same phase of the cardiac cycle. The trigger delay can be chosen so that the particular phase is a phase at which the heart is nearly still, thereby enhancing the consistency of the selected projection data sets.

Different trigger delays can be used to generate a four-dimensional model of the heart. The foregoing aspects of the present invention, such as the first embodiment described above, may be employed to generate interpolated projection views for this purpose. For a given phase of the desired four-dimensional model, a projection view at a selected view angle and a selected axial position may be synthesized by interpolating between projection views at nearby phases.

Figure 39:
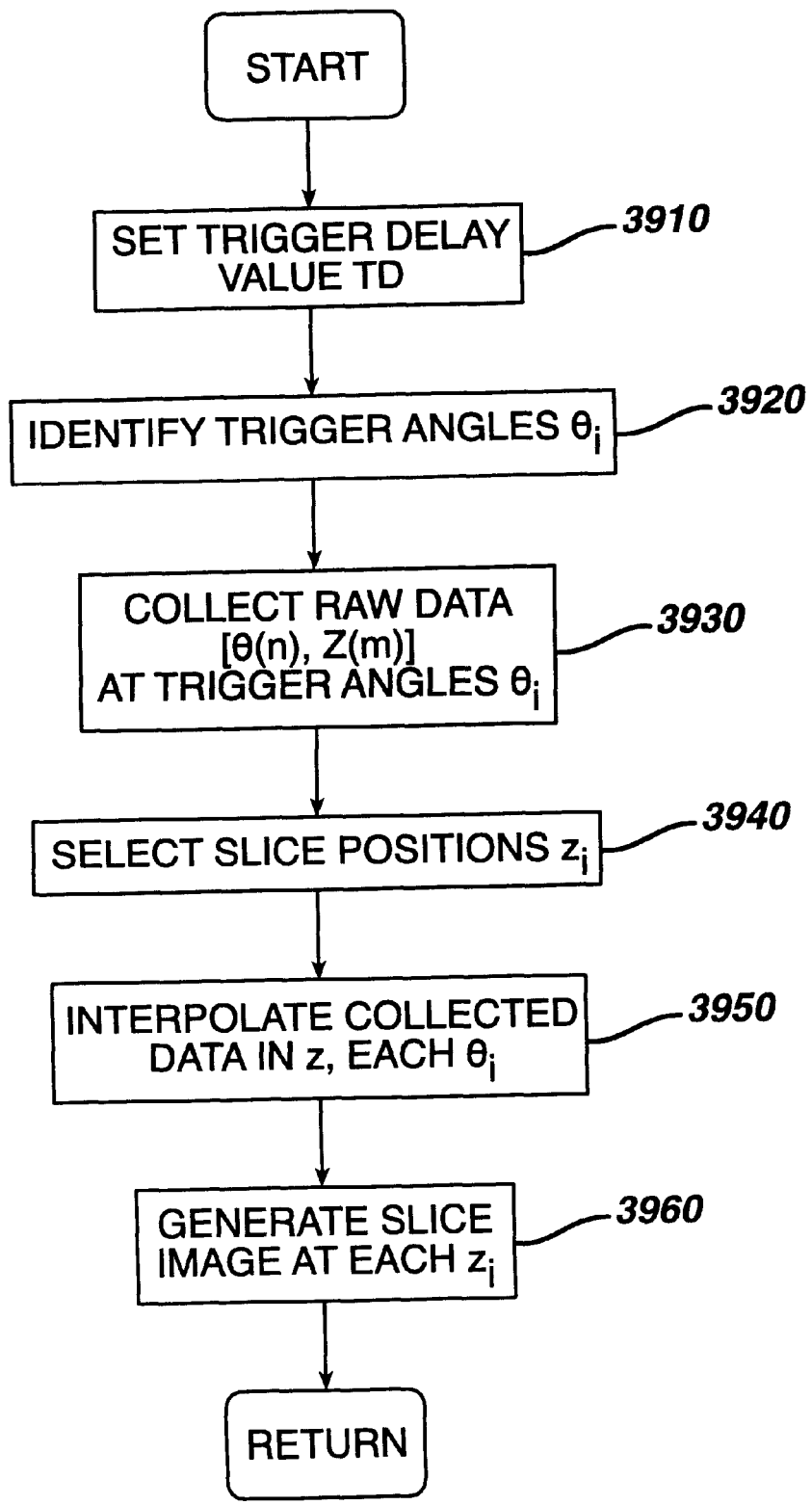
FIG. 39 is a flow diagram for generating a slice image in accordance with one embodiment of the present invention.

FIG. 39 is a flow diagram illustrating a procedure of the present technique as applied in the foregoing context of cardiac imaging. A trigger delay TD is set to a specific value in an operation 3910, thereby determining the particular phase of the heart for the three-dimensional image reconstruction.

As can be seen from FIG. 23, the trigger delay TD will typically correspond to a different view angle θ for each of the scanning rotations (data acquisition cycles ROTATION 1, ROTATION 2, etc.). An operation 3920 therefore identifies the trigger angles $\theta_i$ for the corresponding rotational data sets. An operation 3930 collects the raw data [θ(n), Z(m)] at the corresponding trigger angles $\theta_i$, using the time stamp correlations between the EKG data and the projection data.

An operation 3940 selects the axial positions $z_i$ at which the one or more slice images are to be reconstructed. The positions $z_i$ may be chosen to coincide with the successive axial positions of one of the selected projection data sets, although the helical skew of the volumetric projection data will generally prevent such coincidence for the other sets. An operation 3950 then completes the reconciliation of the axial positions of the selected projection data sets with the specified axial positions for the slice images, by interpolating the collected projection data sets in z. The reconciled projection data sets can then be input to the reconstruction process to generate the desired slice images.

Figure 40:
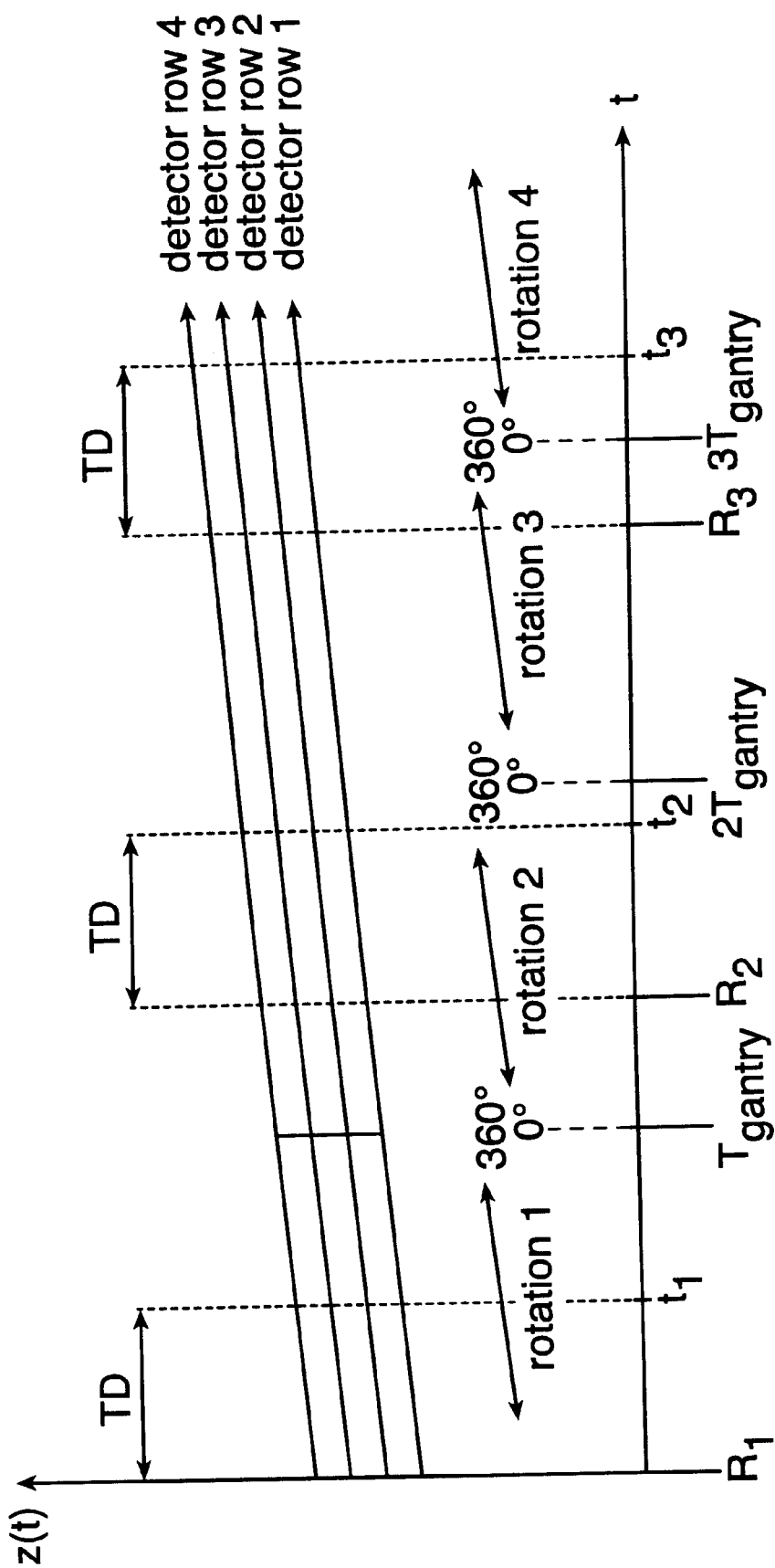
FIG. 40 is a time evolution diagram illustrating rotation cycles in accordance with the present invention.

FIG. 40 shows a time evolution diagram similar to the diagram of FIG. 23, but with the trigger delay TD indicated after the R waves $R_1$, $R_2$, and $R_3$. In the illustrated example, the gantry rotation period $T_{gantry}$ is less than the nominal period of the cardiac cycle. Therefore, triggers $t_1$ and $t_2$ occur in rotations 1 and 2, respectively, but trigger $t_3$ does not occur until rotation 4. A different choice for TD would result in different locations of the triggers $t_i$.

Figure 41:
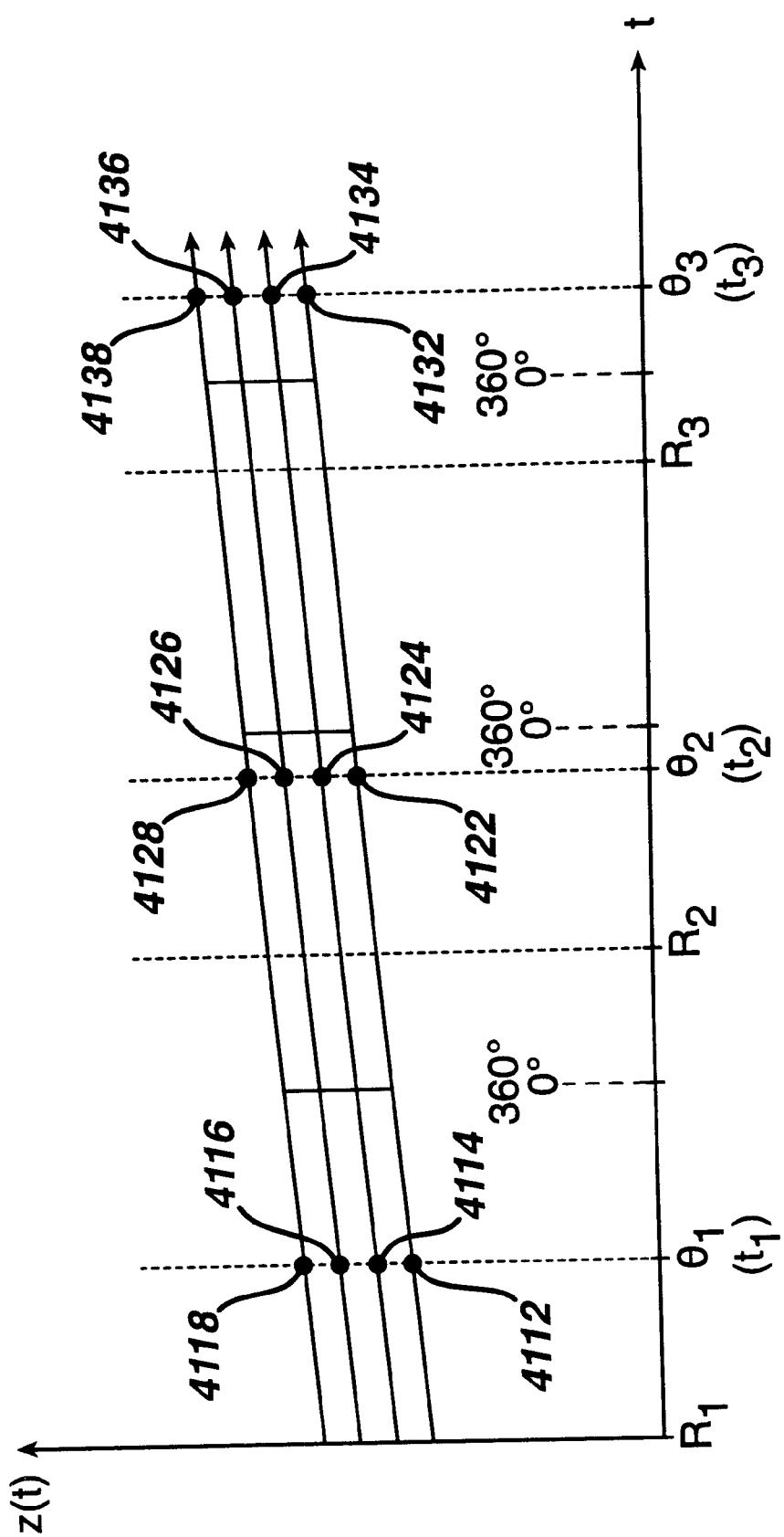
FIG. 41 illustrates trigger angles with corresponding projection views in accordance with the present invention.

FIG. 41 shows that the triggers $t_i$ determine trigger angles $\theta_i$ in the rotations 1, 2, and 4. Each selected trigger angle $\theta_i$ determines a corresponding set of projection views in the time stamped projection data. For example, $\theta_1$ determines the projection views 4112, 4114, 4116, and 4118, which happen to correspond to the first through fourth detector rows of the multi-row detector array. The trigger angle $\theta_2$ determines the projection views 4122, 4124, 4126, and 4128 from rotation 2. The trigger angle $\theta_3$ determines the projection views 4132, 4134, 4136, and 4138 from rotation 4.

A notable point is that all of the projection views 4112 through 4138 represent the imaged heart in the same phase of the cardiac cycle. This is achieved by determining the sets of projection views from the raw data, rather than selecting a specified axial position for the desired image and then searching for suitable projection views in the raw data.

Figure 42:
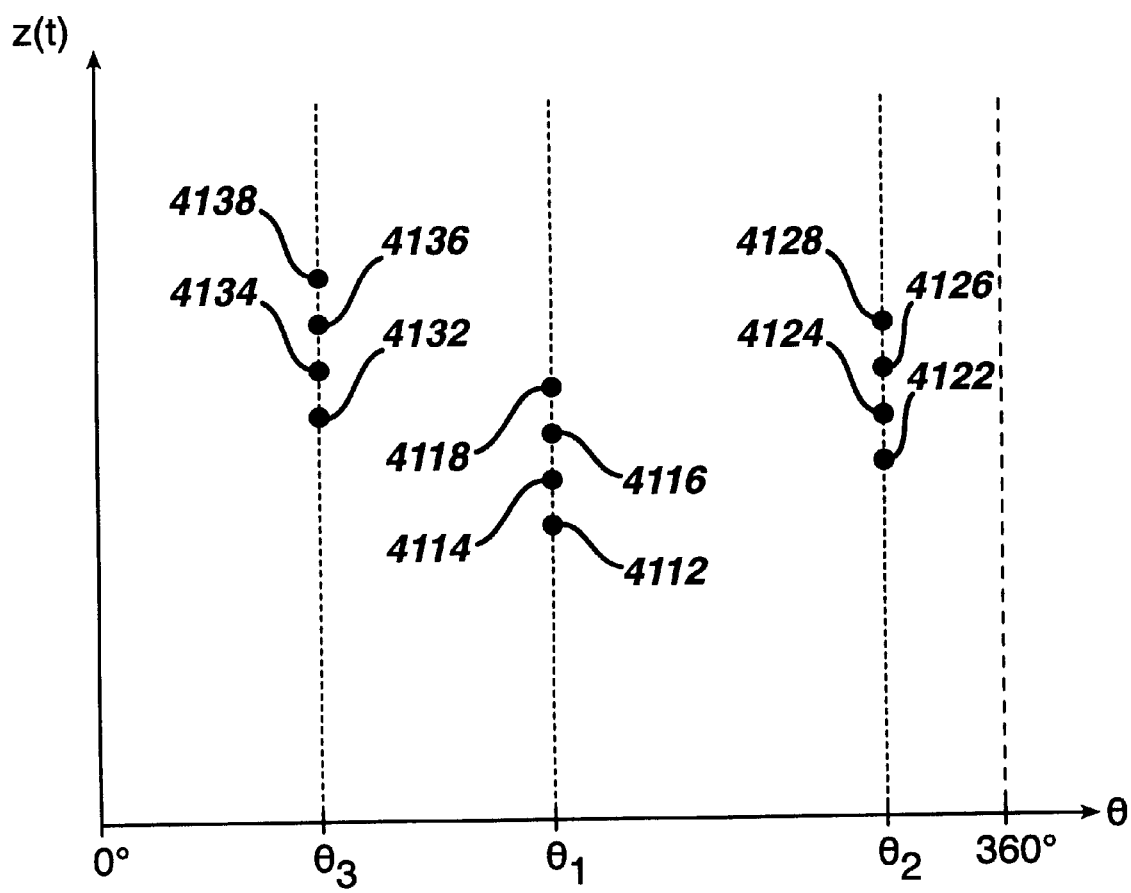
FIG. 42 illustrates projection views and correlated view angles in accordance with the present invention.

FIG. 42 shows the selected sets of projection views at their respective view angles relative to a single cycle of view angles θ. Due to the axial skewing of the raw projection data, the several projection views 4112 through 4138 correspond to different axial positions z. Reconstruction of a slice image at a specified axial position therefore will typically entail reconciliation of the selected projection view sets. A reconciled set of projection views is thereby selected to representing the heart at the same view angles $\theta_1$ through $\theta_3$, but at a single specified axial position z.

Various implementations of the invention described herein above have been tested with clinical cardiac data. These results demonstrate that the invention can noticeably reduce the streaks and other artifacts that occur when the sector approach is applied.

As this invention may be embodied in several forms without departing from the spirit or principal characteristics thereof, the present embodiments are therefore illustrative and not restrictive. Those skilled in the art will appreciate that changes may be made to these embodiments without departing from the principles and spirit of the invention. Accordingly, the scope of the invention is defined by the appended claims rather than by the description preceding them, and all changes that fall within the metes and bounds of the claims, or equivalents of such metes and bounds thereof, are therefore intended to be embraced by the claims.

What is claimed is:

1. A tomographic image generation method, comprising:
   determining a plurality of working projection views of an object at a selected view angle based on initial projection data collected in respective different data acquisition cycles; and
   interpolating between the working projection views to generate an interpolated projection view of the object at the selected view angle.

2. A method according to claim 1, wherein the plurality of working projection views comprises three projection views.

3. A method according to claim 2, wherein the three projection views are respectively based on initial projection data collected in consecutive data acquisition cycles.

4. A method according to claim 1, wherein the plurality of working projection views comprises four projection views.

5. A method according to claim 1, wherein the plurality of working projection views consists of two projection views.

6. A method according to claim 1, wherein the object is in motion during collection of the initial projection data.

7. A method according to claim 6, wherein the motion of the object is cyclical motion.

8. A method according to claim 7, wherein successive cycles of the cyclical motion have a same cycle period.

9. A method according to claim 7, wherein successive cycles of the cyclical motion each has a cycle duration within a range of variation away from a nominal cycle period.

10. A method according to claim 1, wherein:
the object is in cyclical motion during collection of the initial projection data; and
the determining operation comprises selecting the working projection views from projection views of the initial projection data based on the selected view angle and a specified phase of the cyclical motion, whereby the interpolated projection view represents the object at the selected view angle and in the specified phase of the cyclical motion.

11. A method according to claim 10, wherein:
the cyclical motion comprises successive cycles of at least one of translation, rotation, and elastic deformation of the object; and
the specified phase corresponds to a selected translation, rotation, or elastic deformation state assumed by the object in each of the successive cycles.

12. A method according to claim 1, wherein the plurality of working projection views consists of two projection views respectively based on initial projection data collected in two consecutive data acquisition cycles.

13. A method according to claim 12, wherein the specified phase is determined by a selected shape configuration repeatedly assumed by the object during the cyclical change in shape configuration.

14. A method according to claim 1, wherein the initial projection data represent intensities of energetic rays transmitted through the object.

15. A method according to claim 14, wherein the energetic rays comprise x-rays.

16. A method according to claim 14, wherein:
the detector array is a multi-row detector array; and
a cone beam impinges on a side of the object opposite the detector array and the energetic rays comprise rays of the cone beam transmitted through the object to the detector array.

17. A method according to claim 14, wherein the energetic rays are attenuated by the object and the initial projection data represent intensities of the energetic rays subsequent to the attenuation.

18. A method according to claim 1, wherein the working projection views comprise projection views selected from the initial projection data based on contemporaneously collected timing data.

19. A method according to claim 1, wherein:
the initial projection data are collected by the detector array in a cyclical scan comprising a plurality of scanning rotations; and
the initial projection data comprise initial projection views of the object collected in plural successive scanning rotations.

20. A method according to claim 19, wherein:
the object is in cyclical motion during collection of the initial projection data; and
a rotation period of the plurality of scanning rotations is different from a cycle duration of successive cycles of the cyclical motion.

21. A method according to claim 1, wherein the object is an organ of a subject.

22. A method according to claim 21, wherein the organ is a heart.

23. A method according to claim 12, wherein the object is a human heart.

24. A method according to claim 1, wherein the interpolating operation comprises performing weighted linear interpolation between respective projection data of first and second ones of the working projection views.

25. A method according to claim 1, wherein the interpolating operation comprises performing weighted nonlinear interpolation between respective projection data of first and second ones of the working projection views.

26. A method according to claim 25, wherein the weighted nonlinear interpolation is weighted quadratic interpolation.

27. A method according to claim 12 wherein:
the determining operation comprises selecting first and second projection views from the initial projection data as the working projection views, the first projection view comprising projection data collected in a first data acquisition cycle and the second projection view comprising projection data collected in a second data acquisition cycle subsequent to the first data acquisition cycle; and
the interpolating operation comprises performing weighted quadratic interpolation between respective projection data of the first and second projection views.

28. A computer readable medium encoded with a program for tomographic image generation, said program comprising instructions for:
determining a plurality of working projection views of an object at a selected view angle based on initial projection data collected in respective different data acquisition cycles; and
interpolating between the working projection views to generate an interpolated projection view of the object at a selected view angle.

29. A computer readable medium according to claim 28, wherein:
the object is in cyclical motion during collection of the initial projection data; and
the instructions for the determining procedure comprise instructions for selecting each working projection view from projection views of the initial projection data based on the selected view angle and a specified phase of the cyclical motion, whereby the interpolated projection view represents the object at the selected view angle and in the specified phase of the cyclical motion.

30. A computer readable medium according to claim 28, wherein the plurality of working projection views consists of two projection views respectively based on initial projection data collected in two consecutive data acquisition cycles.

31. A computer readable medium according to claim 28, wherein the initial projection data represent intensities of energetic rays transmitted through the object.

32. A computer readable medium according to claim 28, wherein the working projection views comprise projection views selected from the initial projection data based on contemporaneously collected timing data.

33. A tomographic image generation device, comprising:

a storage storing initial projection data collected from an object by a detector array; and a processor determining a plurality of working projection views of an object at a selected view angle based on initial projection data collected in respective different data acquisition cycles, and interpolating between the working projection views to generate an interpolated projection view of the object at the selected view angle.

34. A device according to claim 33, wherein:

the object is in cyclical motion during collection of the initial projection data; and said processor determines the working projection views by selecting each working projection view from projection views of the initial projection data based on the selected view angle and a specified phase of the cyclical motion, whereby the interpolated projection view represents the object at the selected view angle and in the specified phase of the cyclical motion.

35. A device according to claim 33, wherein:

the object is in cyclical motion during collection of the initial projection data; and the plurality of working projection views consists of two projection views respectively based on initial projection data collected in two consecutive data acquisition cycles.

36. A device according to claim 33, wherein the projection data are collected from energetic rays transmitted through the object.

37. A device according to claim 33, wherein the working projection views comprise projection views selected from the initial projection data based on contemporaneously collected timing data.

38. A tomographic image generation system, comprising:

a detector array generating initial projection data for an object; and a computer comprising a processor determining a plurality of working projection views of an object at a selected view angle based on initial projection data collected in respective different data acquisition cycles, and interpolating between the working projection views to generate an interpolated projection view of the object at the selected view angle.

39. A system according to claim 38, wherein:

the object is in cyclical motion during collection of the initial projection data; and the processor determines the working projection views by selecting each working projection view from projection views of the initial projection data based on the selected view angle and a specified phase of the cyclical motion, whereby the interpolated projection view represents the object at the selected view angle and in the specified phase of the cyclical motion.

40. A system according to claim 38, wherein the plurality of working projection views consists of two projection views respectively based on initial projection data collected in two consecutive data acquisition cycles.

41. A system according to claim 38, wherein the initial projection data represent intensities of energetic rays transmitted through the object.

42. A system according to claim 38, wherein the working projection views comprise projection views selected from the initial projection data based on contemporaneously collected timing data.

43. A projection data processing method, comprising:

tagging projection views representing an object in motion with tags indicating respective phases of the motion and respective axial locations for the projection views;

determining the tagged projection views representing the object at respective axial locations within a collimation distance from a selected axial location;

determining separation values representing phase separations between the phases of the determined projection views and a selected phase of the motion;

determining projection view subsets from the determined projection views, each projection view subset comprising plural projection views tagged with respective different phases of the motion at each of plural view angles covering a corresponding reconstruction range;

determining for each view angle of each projection view subset a minimum of the separation values of the projection views of the subset at the view angle;

computing a separation measure for each projection view subset by summing the minimum separation values of the projection view subset;

selecting from the determined projection view subsets a subset having a minimum separation measure of the computed separation measures;

successively selecting the view angles of the selected projection view subset; and interpolating between the plural projection views of the selected projection view subset at each selected view angle to generate an interpolated projection view of the object at the selected axial position and the selected view angle.

44. A method according to claim 43, wherein the motion of the object is cyclical motion.

45. A method according to claim 43, wherein the selected projection view subset comprises for each view angle thereof at least three projection views at respective different phases of the motion.

46. A method according to claim 44, wherein:

the selected projection view subset comprises for each view angle thereof and each of a predetermined number of different phases of the motion a plurality of projection views representing the object at respective axial positions within the collimation distance from the selected axial position; and the interpolating operation comprises, for each of the view angles and each of the predetermined number of different phases, interpolating between the plurality of projection views representing the object at respective axial locations.

47. A tomographic image generation method, comprising:

determining a plurality of working projection views of an object in cyclical motion based on initial projection data collected from the object, the working projection views being based on selected initial projection data collected in respective different data acquisition cycles; and interpolating between the working projection views to generate an interpolated projection view representing the object at the selected view angle and at a specified phase of the cyclical motion.

48. A method according to claim 47, wherein the plurality of working projection views consists of two projection views.

49. A method according to claim 47, wherein the cyclical motion comprises successive cycles of motion each having a cycle duration within a range of variation away from a nominal cycle duration.

50. A method according to claim 47, wherein the cyclical motion comprises successive cycles of periodic motion.

51. A method according to claim 47, wherein the object is a heart within a living subject.

52. A method according to claim 51, wherein the cyclical motion consists of successive repetitions of a cardiac cycle of the heart and the specified phase is a specified phase of the cardiac cycle.

53. A method according to claim 47, wherein the working projection views comprise projection views selected from the initial projection data based on contemporaneously collected timing data.

54. A method according to claim 47, wherein:
the cyclical motion comprises cyclical elastic deformation of the object; and
the specified phase corresponds to a selected shape repeatedly assumed by the object during the cyclical elastic deformation.

55. A method according to claim 47, further comprising collecting quantitative data over plural successive cycles of the cyclical motion, the quantitative data representing a physical property of the object varying synchronously in time with the cyclical motion of the object.

56. A method according to claim 55, wherein:
the object is a heart within a living subject and the cyclical motion comprises successive repetitions of a cardiac cycle of the heart; and
the quantitative data comprises electrocardiogram data representing an electrical cycle of the heart and the specified phase of the cyclical motion coincides with a selected wave of the electrical cycle.

57. A method according to claim 56, wherein the selected wave is an R-wave of the electrocardiogram data and the specified phase occurs at a selected time delay after the R-wave.

58. A method according to claim 47, wherein the initial projection data are determined from energetic rays transmitted through the object.

59. A method according to claim 58, wherein the initial projection data represent attenuation of the energetic rays by the object.

60. A method according to claim 47, wherein the determining operation comprises selecting the working projection views from a plurality of first projection views of the initial projection data.

61. A method according to claim 47, wherein:
the initial projection data are collected in a helical tomographic scan of the object by a multi-row detector array and comprise plural rows of projection data for each of plural rotational data acquisition cycles of the helical tomographic scan; and
the determining operation comprises computing working projection data for each working projection view based on the initial projection data.

62. A method according to claim 61, further comprising selecting an axial position of the helical scan for the interpolated projection view, and wherein for each working projection view, the determining operation comprises:
selecting a rotational data acquisition cycle of the helical tomographic scan corresponding to the specified phase of the cyclical motion,
selecting from the plural rows of projection data for the selected rotation first and second rows of data corresponding to first and second rows of the multi-row detector array nearest to the selected axial position during the selected rotational data acquisition cycle, and
interpolating between the respective projection data of the first and second rows of data to generate the working projection data for the working projection view.

63. A method according to claim 47, wherein:
the initial projection data are collected for the object over a plurality of rotational data acquisition cycles using a rotation period different from a cycle duration for a cycle of the cyclical motion; and
first and second ones of the working projection views represent the object in two consecutive rotational data acquisition cycles.

64. A method according to claim 63, wherein the object is an organ of a living subject.

65. A method according to claim 47, further comprising:
performing the determining operation successively to determine a succession of pluralities of working projection views; and
performing the interpolating operation successively for the succession of pluralities of working projection views to generate a succession of interpolated projection views; and
generating a tomographic image of the object by image reconstruction using the projection views of the succession of pluralities of working projection views and the projection views of the succession of interpolated projection views.

66. A tomographic image generation apparatus, comprising:
a storage storing initial projection data for an object in cyclical motion, the initial projection data relating to a specified phase of the cyclical motion and a selected view angle; and
a processor determining a plurality of working projection views of an object in cyclical motion based on initial projection data collected from the object, the working projection views being based on selected initial projection data collected in respective different data acquisition cycles, and interpolating between the working projection views to generate an interpolated projection view representing the object at the selected view angle and at a specified phase of the cyclical motion.

67. A tomographic image generation system, comprising:
an x-ray source generating a cone beam of x-rays to impinge upon a subject;
a multi-row detector array receiving x-rays transmitted through the subject from said x-ray source and generating initial projection data from the received x-rays, at least a portion of the subject being in cyclical motion and the initial projection data relating to a specified phase of the cyclical motion and a selected view angle; and
a computer determining a plurality of working projection views of the at least a portion in cyclical motion based on initial projection data collected from the subject, the working projection views being based on selected initial projection data collected in respective different data acquisition cycles, said computer interpolating between the working projection views to generate an interpolated projection view representing the at least a portion of the subject at the selected view angle and at a specified phase of the cyclical motion.

68. A tomographic image generation method, comprising:

determining separation measures for projection data covering corresponding reconstruction ranges and representing an imaged object over plural data acquisition cycles; and reconstructing a tomographic image of the object based on a portion of the projection data covering a reconstruction range selected responsive to a determination that the corresponding separation measure satisfies a predetermined selection criterion.

69. A method according to claim 68, wherein determining the separation measures comprises:

calculating a separation value for each projection view comprised in the projection data; and calculating each separation measure based on the separation values of the projection views having view angles in the corresponding reconstruction range.

70. A method according to claim 68, further comprising:

determining a minimum separation measure from the separation measures of the reconstruction ranges; and selecting the reconstruction range corresponding to the minimum separation measure as the selected reconstruction range.

71. A method according to claim 68, further comprising:

collecting the projection data over the plural data acquisition cycles; and collecting timing information contemporaneously with collecting the projection data, the timing information representing a time sequence of a dynamic behavior of the object during collection of the projection data;

and wherein the separation measures are determined based on the contemporaneous timing information.

\* \* \* \* \*